(12) United States Patent
Ging et al.

(10) Patent No.: US 8,371,302 B2
(45) Date of Patent: *Feb. 12, 2013

(54) ERGONOMIC AND ADJUSTABLE RESPIRATORY MASK ASSEMBLY WITH FRAME

(75) Inventors: Anthony Michael Ging, Christchurch (NZ); Saad Nasr, Oatley (AU); Philip Rodney Kwok, Chatswood (AU); Rachael Elizabeth Moore, North Bondi (AU); Andrew Martin Price, Baulkham Hills (AU)

(73) Assignee: Resmed Limited, Bella Vista (AU)

( * ) Notice: Subject to any disclaimer, the term of this patent is extended or adjusted under 35 U.S.C. 154(b) by 73 days.

This patent is subject to a terminal disclaimer.

(21) Appl. No.: 12/787,751

(22) Filed: May 26, 2010

(65) Prior Publication Data

US 2010/0229869 A1    Sep. 16, 2010

Related U.S. Application Data

(63) Continuation of application No. 10/391,440, filed on Mar. 19, 2003, now Pat. No. 7,743,767.

(60) Provisional application No. 60/377,254, filed on May 3, 2002, provisional application No. 60/397,195, filed on Jul. 22, 2002, provisional application No. 60/402,509, filed on Aug. 12, 2002.

(30) Foreign Application Priority Data

Apr. 23, 2002  (AU) .................................... PS 1926

(51) Int. Cl.
*A62B 18/08* (2006.01)
*A62B 18/02* (2006.01)

(52) U.S. Cl. ......... 128/206.24; 128/206.21; 128/205.25; 128/200.24

(58) Field of Classification Search ............. 128/200.24, 128/205.25, 206.21, 206.24, 206.27, 207.13
See application file for complete search history.

(56) References Cited

U.S. PATENT DOCUMENTS

| 1,081,745 A | 12/1913 | Johnston et al. |
| 1,192,186 A | 7/1916 | Greene |
| 1,610,793 A | 12/1926 | Kaufman |
| 1,706,601 A | 3/1929 | Dräger |

(Continued)

FOREIGN PATENT DOCUMENTS

| DE | 956 195 | 1/1957 |
| DE | 17 08 110 | 4/1971 |

(Continued)

OTHER PUBLICATIONS

Examiner's Report mailed Mar. 26, 2007 for co-pending AU application No. 2007100138, 2 pages.

(Continued)

*Primary Examiner* — Annette Dixon
(74) *Attorney, Agent, or Firm* — Nixon & Vanderhye P.C.

(57) ABSTRACT

A respiratory mask assembly for delivering breathable gas to a patient includes a frame having a front surface and a rear surface, opposite the front surface, and adapted in use to face the patient. The frame defines an inner wall and an outer wall extending from the rear surface, the inner and outer walls being spaced to define a channel therebetween. A cushion is removably attachable to the frame such that the cushion and frame are repeatably engagable with and disengagable from one another. The cushion includes a side wall to be inserted into the channel of the frame, the side wall having a first interlocking surface that engages a second interlocking surface provided in the channel when the cushion and frame are engaged with one another. The first and second interlocking surfaces interlock with one another to removably attach the cushion to the frame.

97 Claims, 56 Drawing Sheets

U.S. PATENT DOCUMENTS

| | | | |
|---|---|---|---|
| 2,837,090 | A | 6/1958 | Bloom et al. |
| 2,931,356 | A | 4/1960 | Schwarz |
| 2,939,458 | A | 6/1960 | Lundquist |
| 3,056,402 | A | 10/1962 | Dickinson |
| 3,234,940 | A | 2/1966 | Morton, Jr. |
| 3,752,157 | A | 8/1973 | Malmin |
| 3,990,727 | A | 11/1976 | Gallagher |
| 4,274,406 | A | 6/1981 | Bartholomew |
| 4,405,212 | A * | 9/1983 | Cooper ................... 351/43 |
| 4,414,973 | A | 11/1983 | Matheson et al. |
| 4,454,880 | A | 6/1984 | Muto et al. |
| 4,782,832 | A | 11/1988 | Trimble et al. |
| 4,907,584 | A | 3/1990 | McGinnis |
| 4,919,128 | A | 4/1990 | Kopala et al. |
| 4,944,310 | A | 7/1990 | Sullivan |
| 4,960,121 | A | 10/1990 | Nelson |
| 5,069,205 | A | 12/1991 | Urso |
| 5,243,971 | A | 9/1993 | Sullivan et al. |
| 5,245,995 | A | 9/1993 | Sullivan et al. |
| 5,349,949 | A | 9/1994 | Schegerin |
| 5,441,046 | A | 8/1995 | Starr et al. |
| 5,481,763 | A | 1/1996 | Brostrom et al. |
| 5,533,506 | A | 7/1996 | Wood |
| 5,535,739 | A | 7/1996 | Rapoport et al. |
| 5,647,357 | A | 7/1997 | Barnett et al. |
| 5,697,363 | A | 12/1997 | Hart |
| 5,704,345 | A | 1/1998 | Berthon-Jones |
| 5,724,965 | A | 3/1998 | Handke et al. |
| 5,884,624 | A | 3/1999 | Barnett et al. |
| 5,921,239 | A | 7/1999 | McCall et al. |
| 5,937,851 | A | 8/1999 | Serowski et al. |
| 6,012,455 | A | 1/2000 | Goldstein |
| 6,112,746 | A | 9/2000 | Kwok et al. |
| 6,119,693 | A | 9/2000 | Kwok et al. |
| 6,119,694 | A | 9/2000 | Correa et al. |
| 6,192,886 | B1 | 2/2001 | Rudolph |
| 6,196,223 | B1 | 3/2001 | Belfer |
| 6,269,814 | B1 | 8/2001 | Blaszczykiewicz et al. |
| D448,473 | S | 9/2001 | Barnett et al. |
| 6,338,342 | B1 | 1/2002 | Fecteau et al. |
| 6,347,631 | B1 | 2/2002 | Hansen et al. |
| 6,357,441 | B1 | 3/2002 | Kwok et al. |
| 6,374,826 | B1 | 4/2002 | Gunaratnam et al. |
| 6,397,847 | B1 * | 6/2002 | Scarberry et al. ........ 128/206.24 |
| 6,412,487 | B1 | 7/2002 | Gunaratnam et al. |
| 6,412,488 | B1 | 7/2002 | Barnett et al. |
| 6,422,238 | B1 | 7/2002 | Lithgow |
| 6,439,230 | B1 | 8/2002 | Gunaratnam et al. |
| D464,133 | S | 10/2002 | Barnett et al. |
| D464,428 | S | 10/2002 | Barnett et al. |
| 6,478,026 | B1 | 11/2002 | Wood |
| 6,490,737 | B1 | 12/2002 | Mazzei et al. |
| 6,491,034 | B1 | 12/2002 | Gunaratnam et al. |
| 6,516,802 | B2 | 2/2003 | Hansen et al. |
| 6,532,961 | B1 | 3/2003 | Kwok et al. |
| 6,550,070 | B2 | 4/2003 | Weigand |
| 6,561,190 | B1 | 5/2003 | Kwok |
| 6,595,215 | B2 | 7/2003 | Wood |
| 6,619,288 | B2 | 9/2003 | Demers et al. |
| D486,907 | S | 2/2004 | Guney et al. |
| 6,691,314 | B1 | 2/2004 | Grilliot et al. |
| 6,691,707 | B1 | 2/2004 | Gunaratnam et al. |
| D493,523 | S | 7/2004 | Barnett et al. |
| 6,776,162 | B2 | 8/2004 | Wood |
| 6,796,308 | B2 | 9/2004 | Gunaratnam et al. |
| 6,807,967 | B2 | 10/2004 | Wood |
| 6,895,965 | B2 * | 5/2005 | Scarberry et al. ........ 128/206.24 |
| 6,907,882 | B2 | 6/2005 | Ging et al. |
| 6,997,187 | B2 | 2/2006 | Wood et al. |
| 7,000,613 | B2 | 2/2006 | Wood et al. |
| 7,047,972 | B2 | 5/2006 | Ging et al. |
| 7,152,599 | B2 | 12/2006 | Thomas |
| 7,210,481 | B1 | 5/2007 | Lovell et al. |
| 7,290,546 | B2 | 11/2007 | Sprinkle et al. |
| 8,096,301 | B2 | 1/2012 | Smith et al. |
| 2001/0020474 | A1 | 9/2001 | Hecker et al. |
| 2001/0032648 | A1 | 10/2001 | Jestrabek-Hart |
| 2002/0005198 | A1 | 1/2002 | Kwok et al. |
| 2002/0023649 | A1 | 2/2002 | Gunaratnam et al. |
| 2002/0023650 | A1 | 2/2002 | Gunaratnam et al. |
| 2002/0043265 | A1 | 4/2002 | Barnett et al. |
| 2002/0096176 | A1 | 7/2002 | Gunaratnam et al. |
| 2002/0108613 | A1 | 8/2002 | Gunaratnam et al. |
| 2002/0144684 | A1 | 10/2002 | Moone |
| 2003/0075182 | A1 | 4/2003 | Heidmann et al. |
| 2003/0145859 | A1 | 8/2003 | Bohn et al. |
| 2003/0196656 | A1 | 10/2003 | Moore et al. |
| 2003/0196657 | A1 | 10/2003 | Ging et al. |
| 2003/0196658 | A1 | 10/2003 | Ging et al. |
| 2003/0196662 | A1 | 10/2003 | Ging et al. |
| 2004/0025882 | A1 | 2/2004 | Madaus et al. |
| 2004/0045551 | A1 | 3/2004 | Eaton et al. |
| 2004/0067333 | A1 | 4/2004 | Amarasinghe |
| 2004/0182397 | A1 | 9/2004 | Wood |
| 2005/0028821 | A1 | 2/2005 | Wood et al. |
| 2005/0028822 | A1 | 2/2005 | Sleeper et al. |
| 2005/0076913 | A1 | 4/2005 | Ho et al. |
| 2005/0199239 | A1 | 9/2005 | Lang et al. |
| 2005/0199241 | A1 | 9/2005 | Ging et al. |
| 2006/0081250 | A1 | 4/2006 | Bordewick et al. |
| 2006/0150982 | A1 | 7/2006 | Wood |
| 2006/0162729 | A1 | 7/2006 | Ging et al. |

FOREIGN PATENT DOCUMENTS

| | | |
|---|---|---|
| DE | 199 62 515 | 7/2001 |
| DE | 10035946 | 2/2002 |
| EP | 1 027 905 | 8/2000 |
| EP | 1 099 452 | 5/2001 |
| EP | 1 099 452 A2 | 5/2001 |
| EP | 1258266 | 11/2002 |
| EP | 1 334 742 A2 | 8/2003 |
| FR | 2618340 | 1/1989 |
| FR | 2720280 | 12/1995 |
| FR | 2735030 | 12/1996 |
| GB | 792 377 | 3/1958 |
| GB | 792 377 A | 3/1958 |
| GB | 799225 | 8/1958 |
| GB | 880 942 | 10/1961 |
| GB | 880942 | 10/1961 |
| GB | 2264646 | 9/1993 |
| GB | 2379886 | 3/2003 |
| JP | 11-151297 A | 6/1999 |
| JP | 11-508159 A | 7/1999 |
| WO | WO 87/01950 | 4/1987 |
| WO | WO 97/00092 A1 | 1/1997 |
| WO | WO 98/04310 | 2/1998 |
| WO | WO 98/12965 | 4/1998 |
| WO | WO 98/48878 A2 | 11/1998 |
| WO | WO 99/04842 | 2/1999 |
| WO | WO 99/06116 | 2/1999 |
| WO | WO 99/06116 A | 2/1999 |
| WO | WO 99/61088 | 12/1999 |
| WO | WO 99/61088 A1 | 12/1999 |
| WO | WO 00/69521 | 11/2000 |
| WO | WO 00/78381 | 12/2000 |
| WO | WO 00/78383 | 12/2000 |
| WO | WO 00/78384 | 12/2000 |
| WO | WO 01/32250 | 5/2001 |
| WO | WO 01/62326 | 8/2001 |
| WO | WO 01/95965 | 12/2001 |
| WO | WO 01/97892 | 12/2001 |
| WO | WO 02/07806 | 1/2002 |
| WO | WO 02/11804 | 2/2002 |
| WO | WO 02/47749 | 6/2002 |
| WO | PCT/AU03/00458 | 4/2003 |
| WO | WO 03/082406 | 10/2003 |
| WO | WO 03/090827 | 11/2003 |
| WO | WO 2004/041341 | 5/2004 |
| WO | WO 2004/073777 | 9/2004 |
| WO | WO 2004/073778 | 9/2004 |
| WO | WO 2005/014080 | 2/2005 |
| WO | WO 2005/016402 | 2/2005 |
| WO | WO 2005/016407 | 2/2005 |
| WO | WO 2005/018523 | 3/2005 |
| WO | WO 2005/063328 | 7/2005 |
| WO | WO 2005/079726 | 9/2005 |
| WO | WO 2005/097247 | 10/2005 |

| WO | WO 2006/044118 | 4/2006 |
| WO | WO 2006/044120 | 4/2006 |
| WO | WO 2006/130903 | 12/2006 |

OTHER PUBLICATIONS

Brochure for Adam® CPAP Circuits, Airway Delivery and Management, Puritan Bennett, Apr. 1993, 1 page.
Brochure for ComfortLite™ Nasal Mask, Part Number and Order Guide, Respironics®, Feb. 2004, 2 pages.
Specification Sheet for Infinity™ 481 Direct Nasal Mask, Fisher & Paykel Healthcare, 2004, 2 pages.
Specification Sheet for Opus Nasal Pillows Mask, Fisher & Paykel Healthcare, 2007, 2 pages.
U.S. Appl. No. 60/424,694, filed Nov. 8, 2002, Amarasinghe et al.
U.S. Appl. No. 60/488,810, filed Jul. 22, 2003, Gunaratnam et al.
U.S. Appl. No. 60/492,282, filed Aug. 5, 2003, Wood.
U.S. Appl. No. 60/493,325, filed Aug. 8, 2003, Wood.
U.S. Appl. No. 60/494,119, filed Aug. 12, 2003, Gunaratnam et al.
U.S. Appl. No. 60/496,059, filed Aug. 18, 2003, Ho.
U.S. Appl. No. 60/501,028, filed Sep. 9, 2003, Wood.
U.S. Appl. No. 60/529,696, filed Dec. 16, 2003, Lithgow et al.
U.S. Appl. No. 60/533,214, filed Dec. 31, 2003, Drew.
U.S. Appl. No. 60/560,610, filed Apr. 9, 2004, Gunaratnam.
U.S. Appl. No. 60/619,426, filed Oct. 15, 2004, Bordewick.
U.S. Appl. No. 60/632,193, filed Jun. 6, 2005, Lubke et al.
U.S. Appl. No. 60/687,453, filed Jun. 6, 2005, Lubke et al.
U.S. Appl. No. 60/702,581, filed Jul. 27, 2005, Lubke et al.
U.S. Appl. No. 60/795,562, filed Apr. 28, 2006, Lubke et al.
U.S. Appl. No. 11/698,066, filed Jan. 26, 2007, Ging et al.
European Search Report for EP 03252555.2, dated Jan. 13, 2004, 5 pages.
Partial European Search Report for EP 06 01 8065, mailed Oct. 11, 2006, 5 pages.
European Search Report from EP Appln. No. 03 25 2554, dated Sep. 22, 2003, 3 pages.
*Gray's Anatomy*, pp. 546, 547, 550, and 1631 (3 pages) (1995).
European Search Report dated Mar. 16, 2007 issued in corresponding EP Application No. 06 01 8065.
Respironics, The Comfort Series™, "The Bridge of the Nose. Okay, Enough of That Sore Subject.," Dec. 2004, 2 pages.
Respironics, Simplicity™, Nasal Mask Instructions, Feb. 2006, 2 pages.
Invacare Corporation, Assembly, Installation, and Operating Instructions, Invacare® Twilight™ Nasal Mask and Headgear, Model No. ISP2000 Standard, Oct. 2003, 12 pages.
Decision of Rejection delivered Sep. 1, 2009 in corresponding Japanese Application No. 2003-117861, together with English translation.
Notice of Reasons for Rejection and English Translation for corresponding Japanese Application No. 2010-117836, dated May 15, 2012 (5 pages).
Notice of Reasons for Rejection and English Translation in corresponding Japanese Application No. 2010-131741, mailed Jun. 26, 2012, 4 pages.
European Search Report for corresponding EP Application No. 10184921, mailed Jul. 6, 2012, 12 pages.
European Search Report for corresponding EP Application No. 10184931, mailed Jul. 6, 2012, 12 pages.
Examination Report for corresponding New Zealand Application No. 600484, mailed Jun. 15, 2012, 2 pages.

* cited by examiner

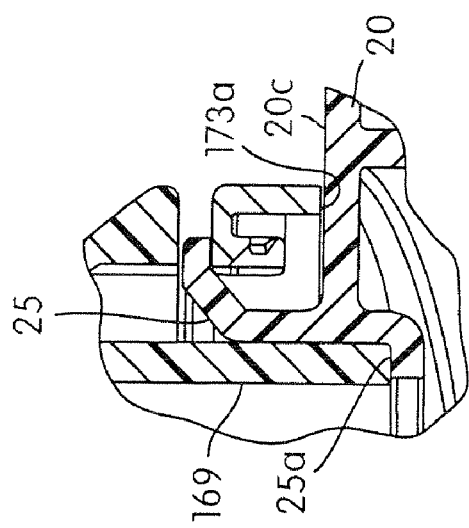
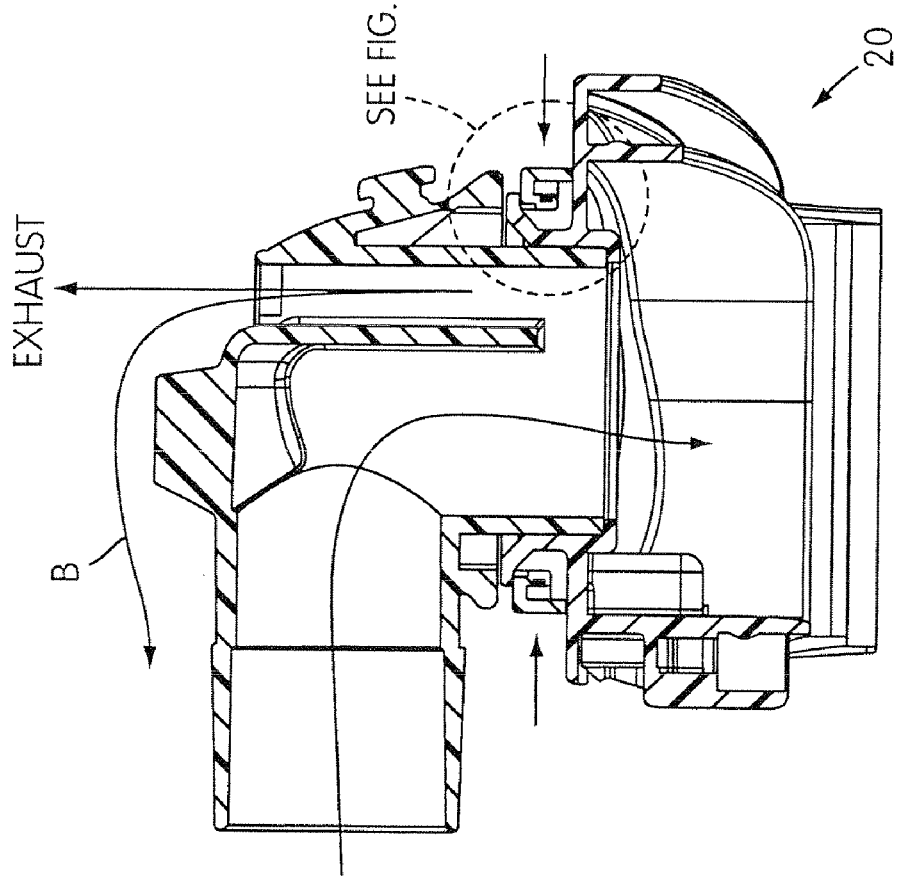
FIG. 19c-2
FIG. 19c-1

1. Nasal Root Width
2. Nasal Bridge Width
3. Nose Width
4. Mouth Width

5. Nose Height
6. Nose Bridge Length
7. Nose Tip Protrusion
8. Nasal Root Depth

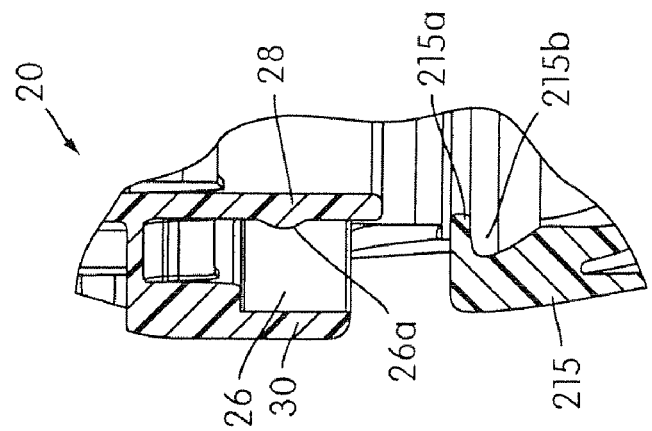
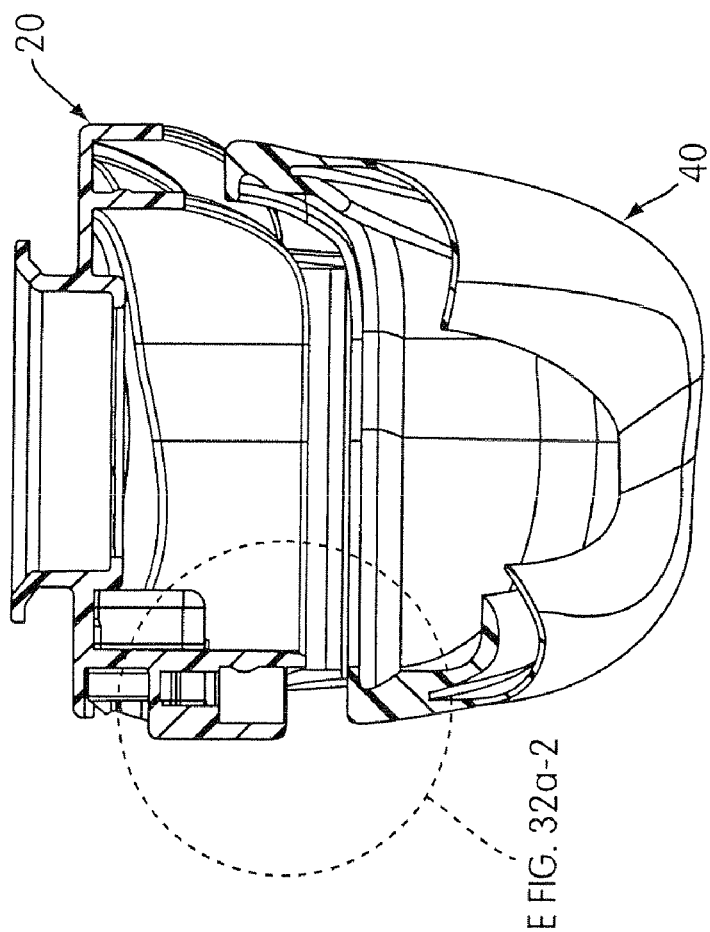
FIG. 32a-2
FIG. 32a-1

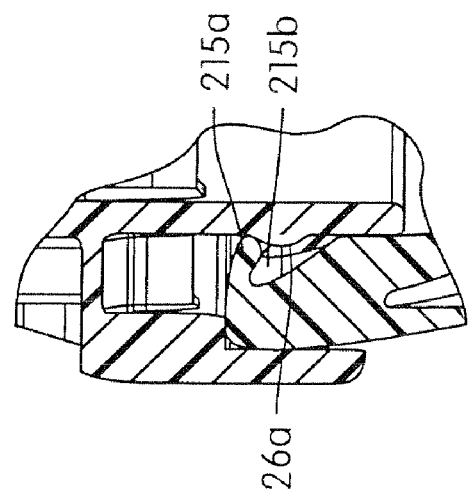
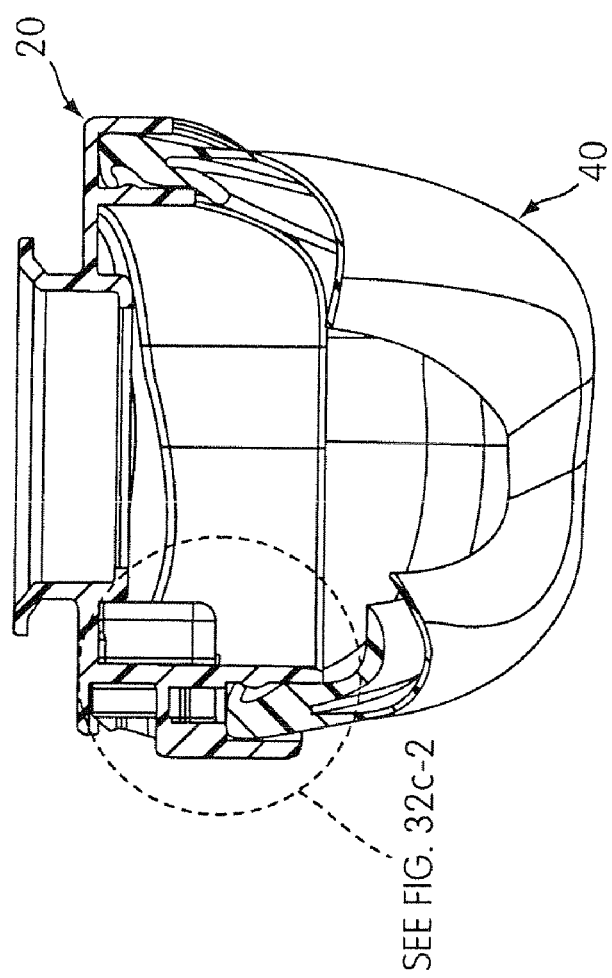
FIG. 32c-2
FIG. 32c-1

ERGONOMIC AND ADJUSTABLE RESPIRATORY MASK ASSEMBLY WITH FRAME

CROSS-REFERENCE TO RELATED APPLICATIONS

This application is a continuation of Ser. No. 10/391,440, filed Mar. 19, 2003, allowed, which claims the benefit of U.S. Provisional Applications of Moore et al., Ser. Nos. 60/377,254, 60/397,195, and 60/402,509, as well as Australian Application PS 1926, filed Apr. 23, 2002, each incorporated into the present application by reference in its entirety.

FIELD OF THE INVENTION

The invention relates to a nasal mask for use in the delivery of Non-invasive Positive Pressure Ventilation (NPPV) and for nasal continuous positive airway pressure (nasal CPAP) therapy of sleep disordered breathing (SDB) conditions such as obstructive sleep apnea (OSA).

BACKGROUND OF THE INVENTION

The application of nCPAP for treatment of OSA was taught by Sullivan in U.S. Pat. No. 4,944,310, incorporated herein by reference in its entirety. In nCPAP treatment of OSA, pressurized air or other breathable gas is provided to the entrance of a patient's airways at a pressure elevated above atmospheric pressure, typically in the range 4 to 20 cm H2O to "splint" open the patient's upper airways and prevent apneas.

Apparatus to deliver nasal CPAP and NPPV therapy typically comprises a blower, an air delivery conduit and a patient interface. The blower may be programmed to deliver a range of different forms of therapy. In one form, a constant pressure of air or breathable gas is provided to the patient. It is also known for the level of treatment pressure to vary from breath to breath in accordance with patient need, that form of treatment being known as automatically adjusting nasal CPAP treatment as described in U.S. Pat. No. 5,245,995 (Sullivan and Lynch), incorporated herein by reference in its entirety. NPPV is another form of treatment for breathing disorders. In its most basic form, a relatively higher pressure of gas may be provided in the patient mask during the inspiratory phase of respiration and a relatively lower pressure or atmospheric pressure being provided in the patient mask during the expiratory phase of respiration. In other modes, the pressure can be made to vary in a complex manner throughout the respiratory cycle. For example, the pressure at the mask during inspiration or expiration can be varied through the period of treatment. See, for example, U.S. Pat. No. 5,704,345 and International Patent Publication Nos. WO98/12965 and WO99/61088, all of which are incorporated by reference herein in their entireties. In this specification, the term NPPV therapy will be used to describe all these forms of NPPV and nasal CPAP therapy.

The patient interface for NPPV therapy may take many forms, such as a nasal mask assembly, a nose and mouth mask assembly, nasal cushions or a nasal prongs or pillows assembly. A mask assembly typically includes a rigid shell, a soft face-contacting cushion, a forehead support and headgear for securing the mask to the head.

In one known mask assembly, the headgear includes a cap portion with four straps. In use, the cap portion engages the occipital portion of the patient. Furthermore, in use, the two lower straps extend between the cap portion and a nasal mask while the two upper straps extend between the cap portion and a forehead support. See, for example, U.S. Pat. No. 6,119,693 (Kwok, Matchett and Grant), incorporated herein by reference in its entirety.

Some patient interfaces include quick or convenient release mechanisms for enabling a patient and/or clinician to disengage from the blower, blower tube and/or the mask/headgear assembly. Quick or convenient release mechanisms are useful where NPPV therapy needs to be temporarily interrupted or where a system failure causes a cessation of gas flow to the patient interface. For example, as disclosed in U.S. Pat. No. 6,422,238, incorporated herein by reference in its entirety, the headgear and mask can be removed from the patient by pulling a conveniently located cord to decouple hook and loop fasteners between engaging headstraps that are positioned, for example, at the rear of the headgear assembly. In another example, as disclosed in U.S. Pat. No. 6,374,826, incorporated herein by reference in its entirety, the headgear/mask assembly can be removed from the patient by detaching a connector member for the headstrap, which connector member is connected directly to the frame of the mask. See also U.S. Pat. No. 3,990,727, which discloses a quick detachable coupler that appears to be employed by the SleepNet™ IQ™ mask.

Since the patient must be able to sleep while wearing the patient interface, it is desirable that it be comfortable. In addition, the patient interface should provide a good seal to prevent or reduce leaks, or to better control any leak that occurs and to maintain efficacy of treatment. Since the shape of people's noses, faces and heads vary widely, from a commercial perspective, it is important to be able to manufacture patient interfaces which can accommodate this range of facial shapes without having to carry excessive inventory through a large number of sizes. A number of patient interfaces have been designed with the goals of patient comfort, ease of use, adjustability and the ability to accommodate a wide range of patient face and head shapes in mind.

U.S. Pat. No. 5,243,971 (Sullivan and Bruderer) provides a patient interface (both nasal and full-face masks) that is suitable for use in NPPV therapy. The mask has a face contacting portion mounted to a shell which is sized and shaped to overfit the nose region of an intended wearer, and the face contacting portion is in the form of a distendable membrane which is molded from an elastic material. U.S. Pat. No. 5,243,971 is hereby incorporated by reference in its entirety.

U.S. Pat. Nos. 6,357,441 and 6,112,746 (Kwok and Styles) each describe a nasal cushion which comprises a substantially triangularly shaped frame from which extends a membrane. These patents are hereby incorporated by reference in their entirety.

Other nasal masks are disclosed in U.S. Pat. Nos. 5,724,965 and 6,119,694, incorporated by reference in their entirety. Each describes a nasal cushion that engages with the tip of the nose or that portion of the nose in the horizontal plane just above the upper lip of the patient. In PCT/US00/11329 (WO 00/69521), incorporated by reference in its entirety, a triangular-shaped nasal cushion includes a tapered profile that narrows towards the face of the patient. Some of these prior art masks/cushions has experienced significant challenges from the perspective of patient comfort, potential nasal vent occlusion, stability and/or sealing (especially at the nasal bridge and cheek regions).

A number of adjustable forehead supports have been developed with the aim of achieving a serviceable seal while increasing patient comfort and accommodating the greatest number of patients in the population. For example, U.S. Pat. No. 6,119,693 (Kwok, Matchett and Grant) describes an adjustable forehead support for a nasal mask or full-face mask. The forehead support may be adjusted for the different shapes and sizes of a facial profile. The angle of the seal relative to the face may be adjusted with this invention. U.S. Pat. No. 6,119,693 is hereby incorporated by cross-reference in their entirety. In International Patent Application PCT/AU00/00097 (WO 00/78384), a forehead support is disclosed that is adapted to be secured to a respiratory mask. International Patent Application PCT/AU00/00097 (WO 00/78384) is hereby incorporated by cross-reference in its entirety.

Accordingly, a need has developed in the art to provide a mask assembly that is capable of overcoming the drawbacks or limitations of the prior art.

BRIEF SUMMARY OF THE INVENTION

One aspect of the present invention is directed towards a comfortable patient interface for delivering NPPV therapy.

Another aspect of the invention is to provide a patient interface that will result in improved patient compliance with NPPV therapy.

It is another aspect of the present invention to create a cushion that is capable of sealing on a smaller area of the nose as compared to known masks, while retaining or exceeding the comfort level of the ResMed Mirage® and Ultra Mirage® cushions.

It is a further aspect of the present invention to reduce the perceived and/or actual size and/or weight of a nasal mask and provide a less intrusive mask for the user.

Another aspect of the present invention is to provide a mask assembly in which the mask and headgear have a reduced amount of connections that are provided in a convenient and intuitive location for quick attachment and/or detachment by the patient, while not being easily detached accidentally.

Another aspect of the invention is to provide a mask assembly in which it is not necessary to provide a forehead support or an adjustment mechanism for the forehead support, while maintaining stability of the mask in use.

Another aspect is to provide a nasal mask capable of fitting a wide range of patients, so as to decrease or minimize inventory requirements and the number of differently sized masks/cushions that are required for production.

Yet another aspect of the present invention is to provide a nasal mask that offers more comfort to the patient, e.g., by better avoiding the application of unwanted localized pressure points in the facial contacting regions especially to the sensitive nasal bridge region of the patient, while maintaining a good seal, with or without the assistance of positive pressure to form or maintain the seal. Another aspect of the present invention is to avoid contact with the upper nasal bridge region, while avoiding localized pressure points along the lower nasal bridge region where the bony portion transitions into a portion of the nose containing more cartilage.

Another aspect of the present invention is to avoid application of unwanted localized contact pressure or forces that may increase undesirably the impedance of airflow through the patient's nares/naris and nasal passages, especially through the nasal vent.

Still another aspect is to provide a headgear assembly which can provide added stability to the mask/cushion assembly. In embodiments, the headgear may be made of or include at least one layer which imparts a degree of stiffness to the headstraps to assist in the stabilization of the mask/cushion assembly, which may obviate the need for a forehead support and thereby decrease visual obstructions near the patient's eyes and better enhance or at least not hinder the patient's ability to don, wear or remove eye glasses with the mask system in use. At least a portion of the headstrap itself may be formed of a relatively more rigid material in comparison to relatively flexible headstraps, instead of providing a multiple layer structure. The headgear may include a relatively large, hand-manipulable clip member that can be quickly and easily attached and/or detached from the head strap and/or the mask frame. Alternatively, the headgear may be magnetically coupled with the mask frame.

Another aspect of the present invention is to provide a convenient or quick release mechanism which requires little effort or dexterity to operate.

Another aspect of the present invention is to provide a frame which includes and/or integrates a quick release mechanism so that the clip member of the head straps can be easily detached from the frame. The quick release mechanism may include at least one connector portion formed in one piece with the frame. A mating connector portion can be provided on a portion of the headgear. The mask system is attached to a source of pressurized air which is delivered via an air delivery conduit. The conduit may be directly attached to the mask with its lumen in fluid communication with the mask chamber in order to supply pressurized air to the entrance of the patient's airway. Preferably an intermediate piece connects the air delivery conduit to the mask. Preferably the intermediate piece is an elbow joint, which will be better described below. The frame may include an extended tube protruding from the outside surface of the mask, which can improve the seal between the elbow joint and the mask frame and also improve the stability of the connection between the mask frame and the elbow joint. The extended tube may include a flange for attachment to the elbow assembly. Preferably the elbow assembly may be easily manipulated to quickly and readily detach the elbow joint from the mask frame during a temporary interruption in patient treatment. The elbow assembly may include a vent to atmosphere. Preferably the vent is in fluid communication with the system air path via an exhaust passage which is separated from the incoming gas path, for example, by using a baffle provided within a portion of the elbow joint.

Another aspect of the invention is to provide a generally trapezoidal shaped mask cushion for a patient interface.

Another aspect of the invention provides a respiratory mask assembly for delivering breathable gas to a patient. The respiratory mask assembly according to one embodiment includes a frame having a front surface and a rear surface, opposite the front surface, and adapted in use to face the patient. The frame defines an inner wall and an outer wall extending from the rear surface, the inner and outer walls being spaced to define a channel therebetween. A cushion is removably attachable to the frame such that the cushion and frame are repeatably engagable with and disengagable from one another. The cushion includes a side wall to be inserted into the channel of the frame, the side wall having a first interlocking surface that engages a second interlocking surface provided in the channel when the cushion and frame are engaged with one another. The first and second interlocking surfaces interlock with one another to removably attach the cushion to the frame.

Of course, portions of the described aspects of the present invention may form sub-aspects of the present invention. Also, various ones of the sub-aspects and/or aspects may be combined in various manners and also constitute additional aspects or sub-aspects of the present invention. These and other features and aspects of the present invention will be described in or be apparent from the detailed description below read in conjunction with the attached Figures, where like reference numerals indicate like components.

BRIEF DESCRIPTION OF THE DRAWINGS

The accompanying drawings facilitate an understanding of the various embodiments of this invention. In such drawings:

FIG. 6b is an exploded view of the embodiment of FIG. 6a;

FIG. 9b is a bottom view of the locking clip of FIG. 9a;

FIG. 10b is a bottom view of the clip of FIG. 10a;

FIG. 10c is a top view of the clip of FIG. 10a;

FIG. 10d is a perspective view of the clip of FIG. 10a;

FIGS. 19a-1-19c-2 are sequential sectional views of the swivel elbow as shown in FIG. 18, illustrating connection with a flange extending from the front surface of the frame;

FIG. 23 is a perspective view of a connector tube of the nasal mask of FIG. 6a;

FIGS. 24c-24f illustrate various perspectives of the cushion shown in FIG. 24a;

FIG. 25b is a face side view of the cushion of FIG. 25a;

FIGS. 32a-1-32c-2 illustrate an additional embodiment of the present invention for engagement between the frame and cushion, the cushion showing CAD construction lines;

DETAILED DESCRIPTION OF PREFERRED EMBODIMENTS

Figure 1:
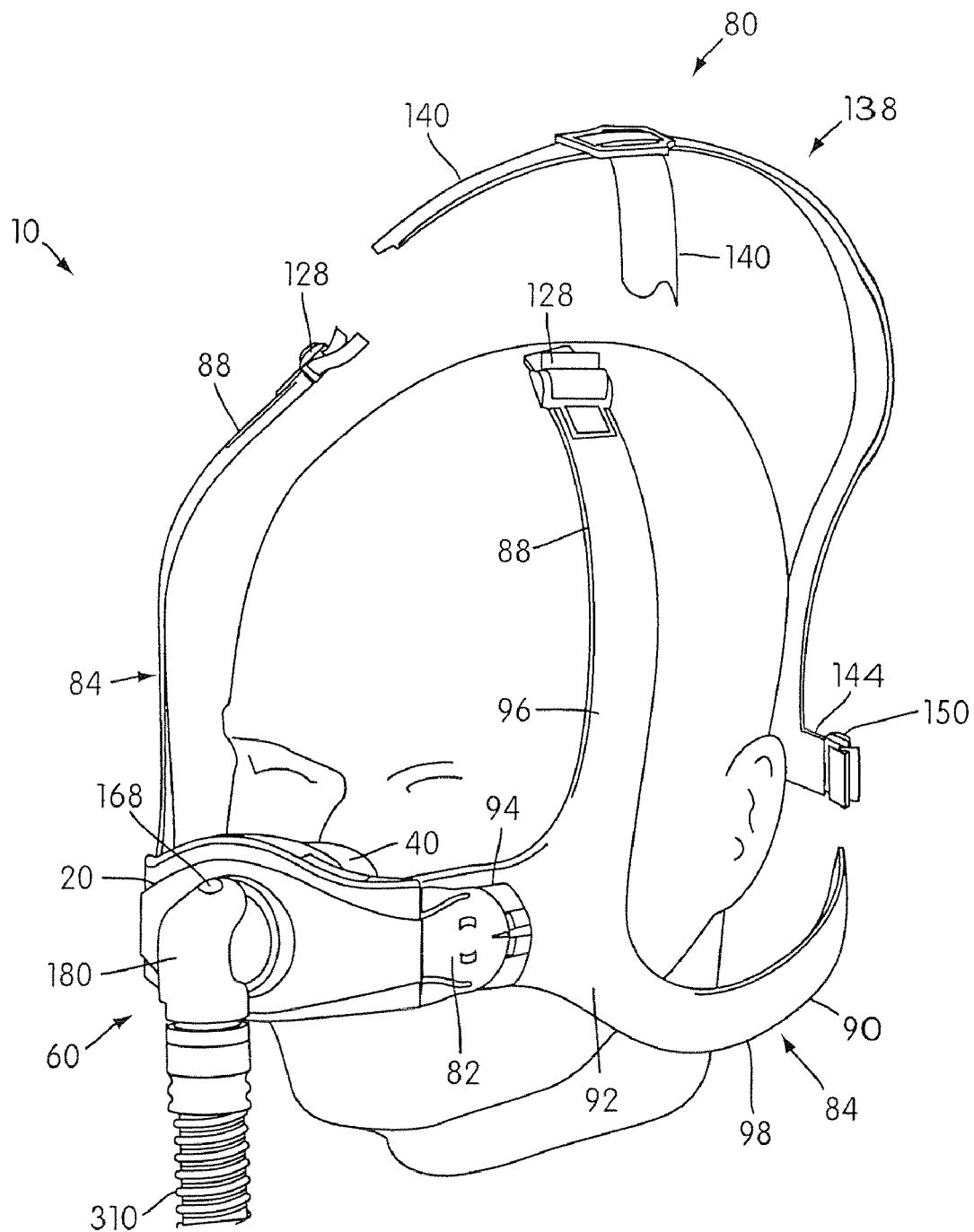
FIG. 1 is a perspective view of a nasal mask assembly according to one preferred embodiment of the present invention.
Figure 6A:
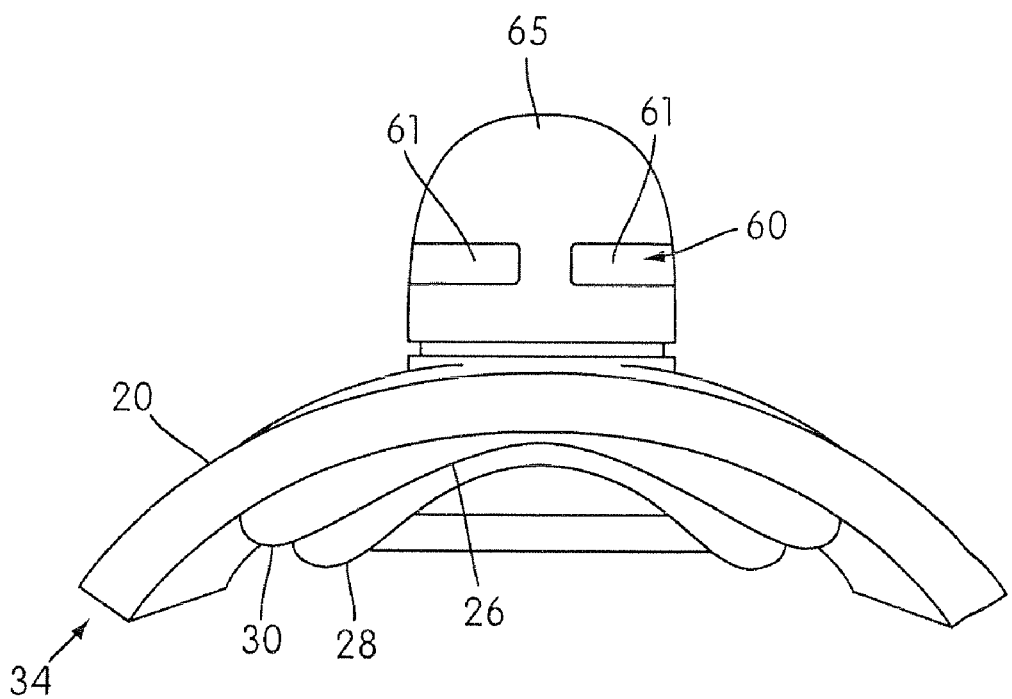
FIG. 6a is a top view of an elbow assembly and frame according to another embodiment of the present invention.
Figure 6B:
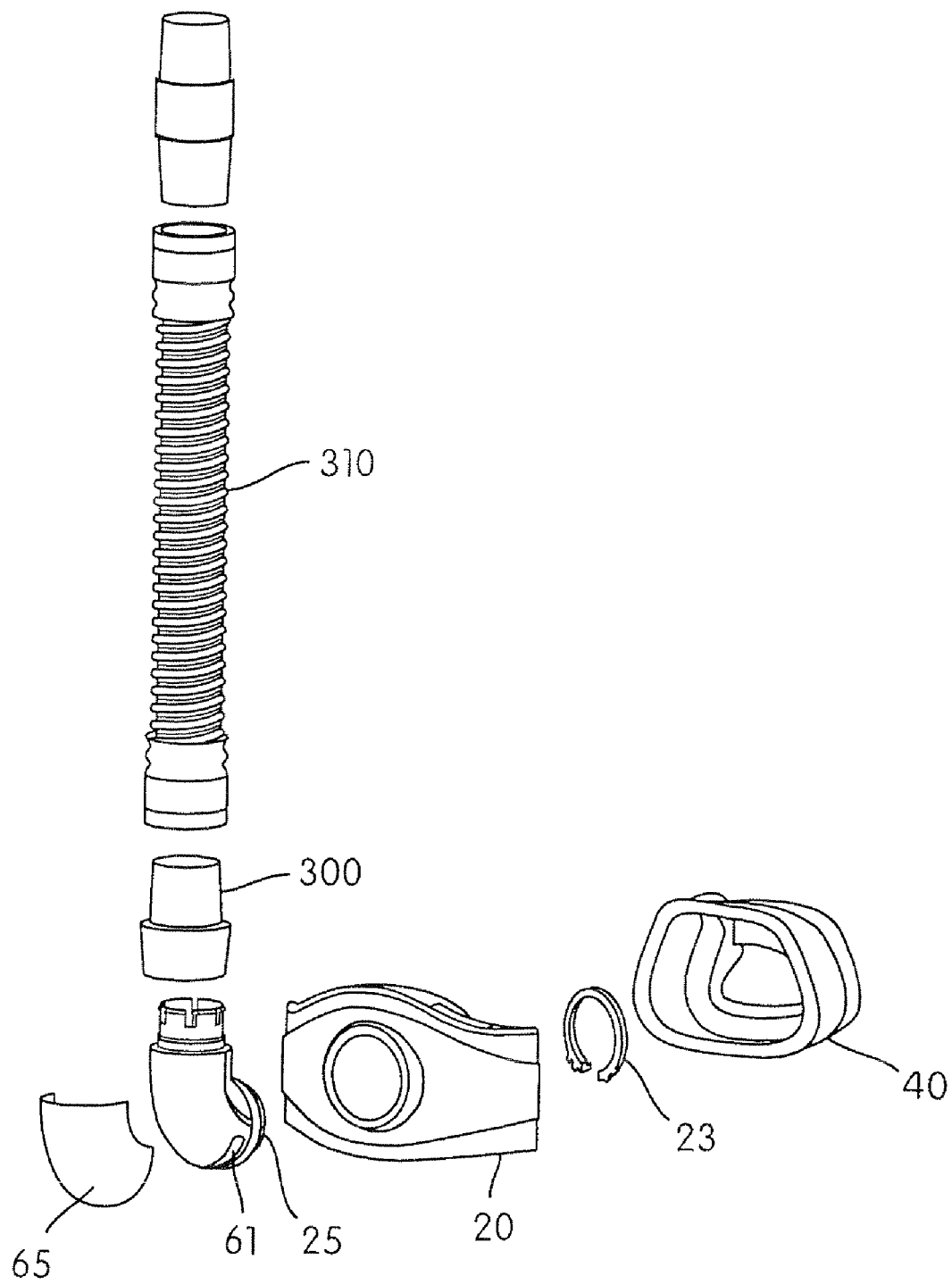

Two main embodiments are described in the figures. Although many of the features and/or parts of each embodiment are the same, there are several parts and/or elements that are different. For example, while FIG. 1 shows one embodiment of an elbow assembly 60 according to the present invention, FIGS. 6a-6b show another arrangement of the elbow assembly 60. Other differences between the embodiments will be described below. Moreover, several alternative approaches are also described with respect to various parts and/or elements, and those alternative approaches should be considered as additional preferred embodiments of the present invention.

Figure 1B:
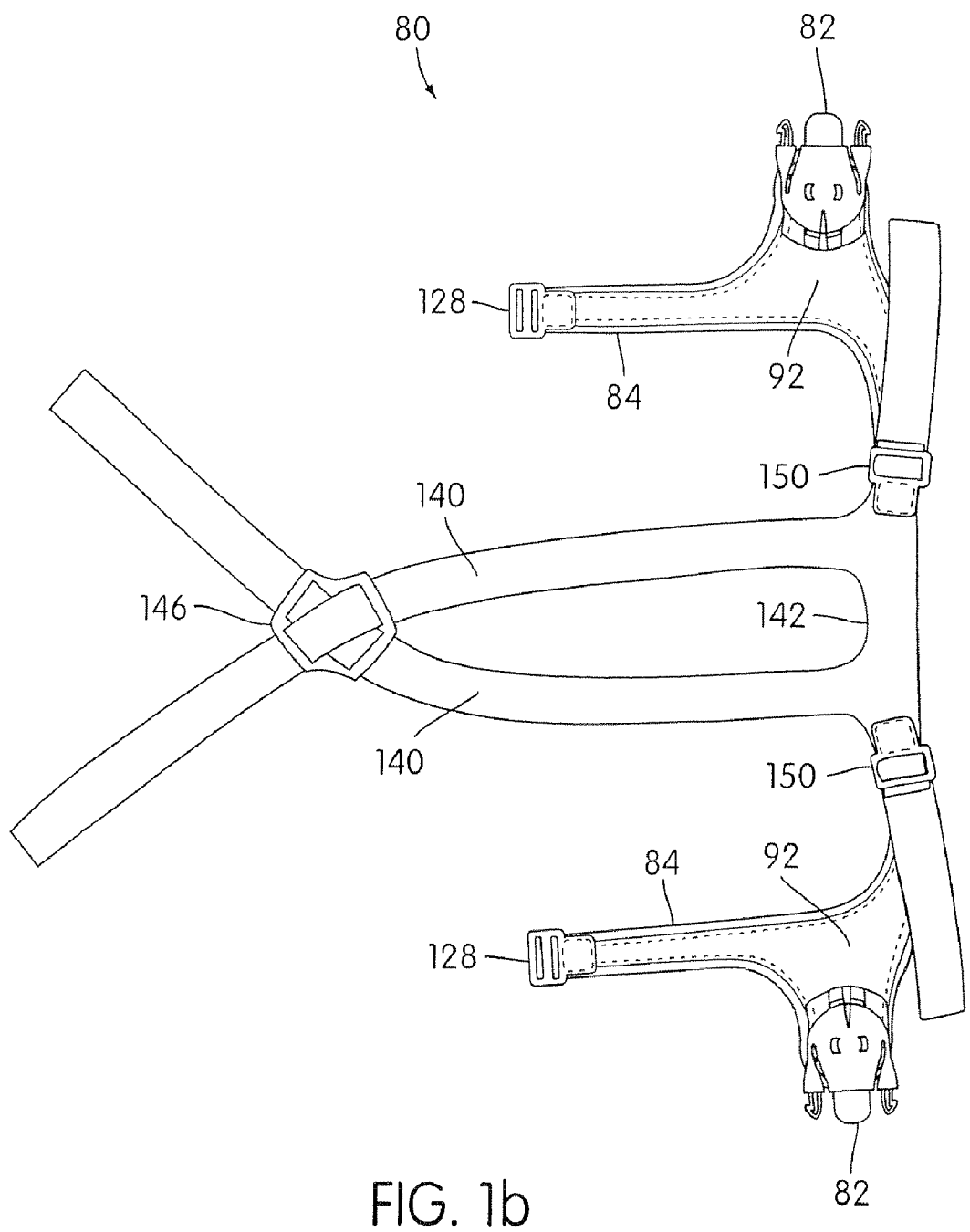
FIG. 1b shows a headgear assembly according to an embodiment of the invention.
Figure 2:
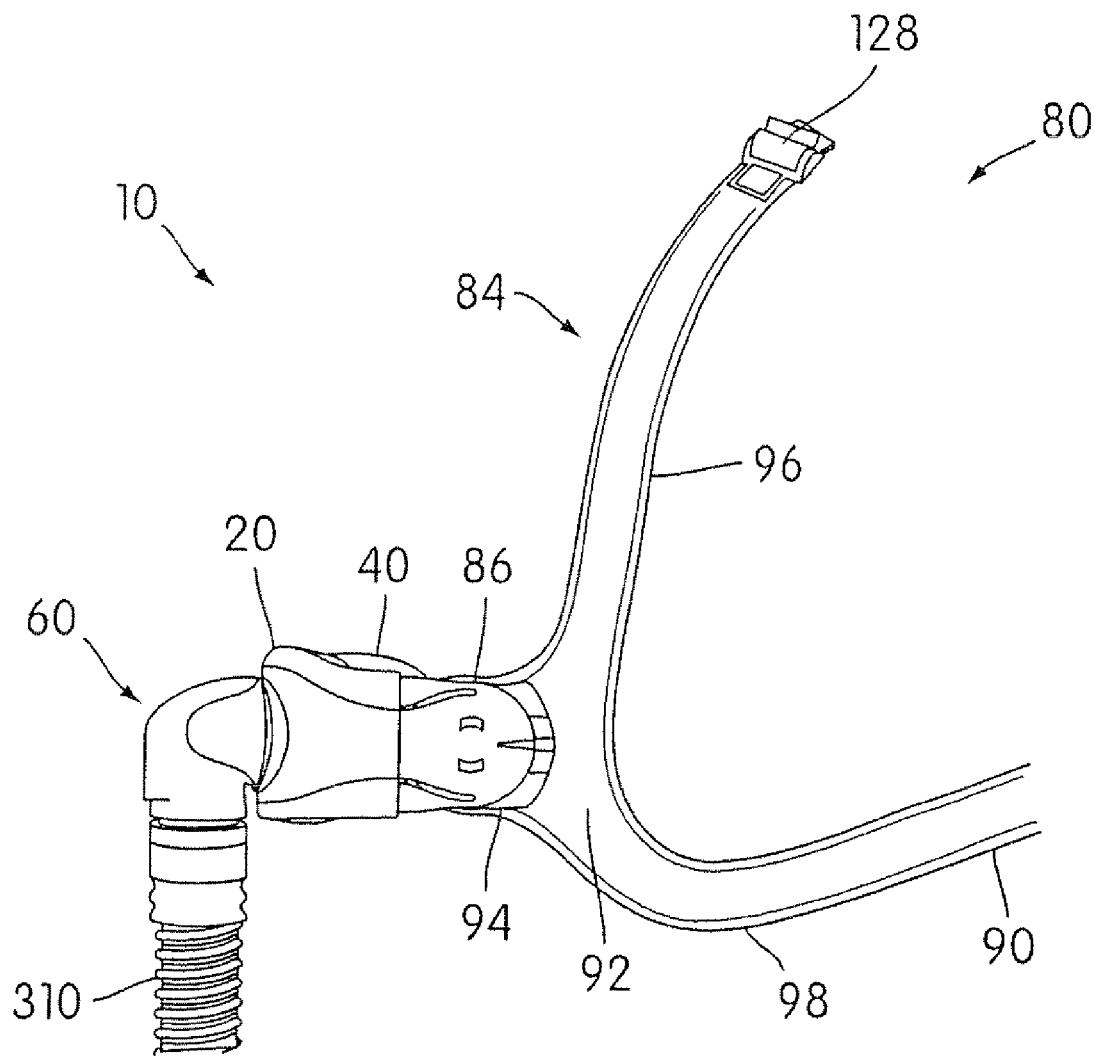
FIG. 2 is a partial side view of the nasal mask assembly of FIG. 1.
Figure 3:
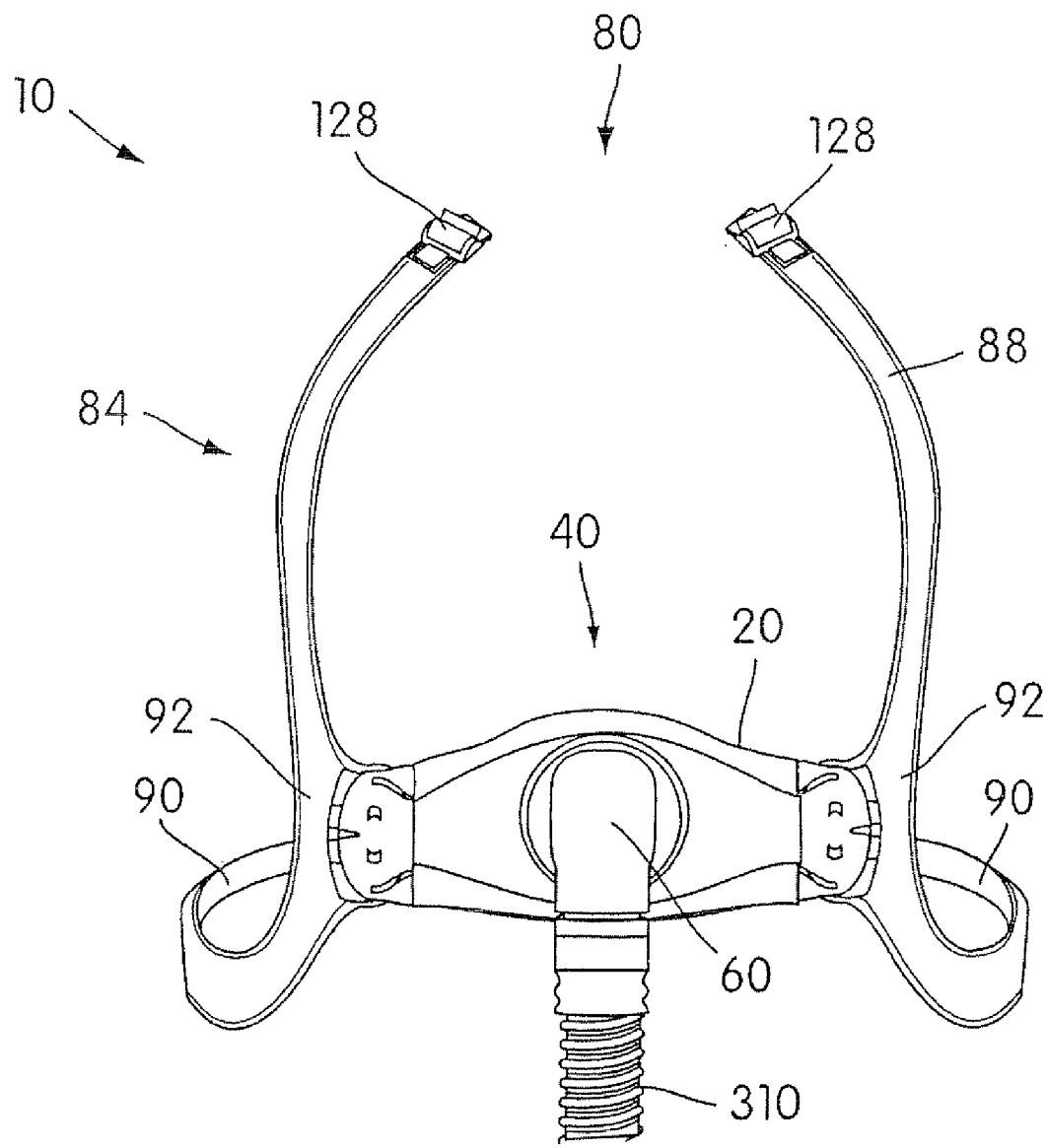
FIG. 3 is a partial front view of the nasal mask assembly of FIG. 1.
Figure 4:
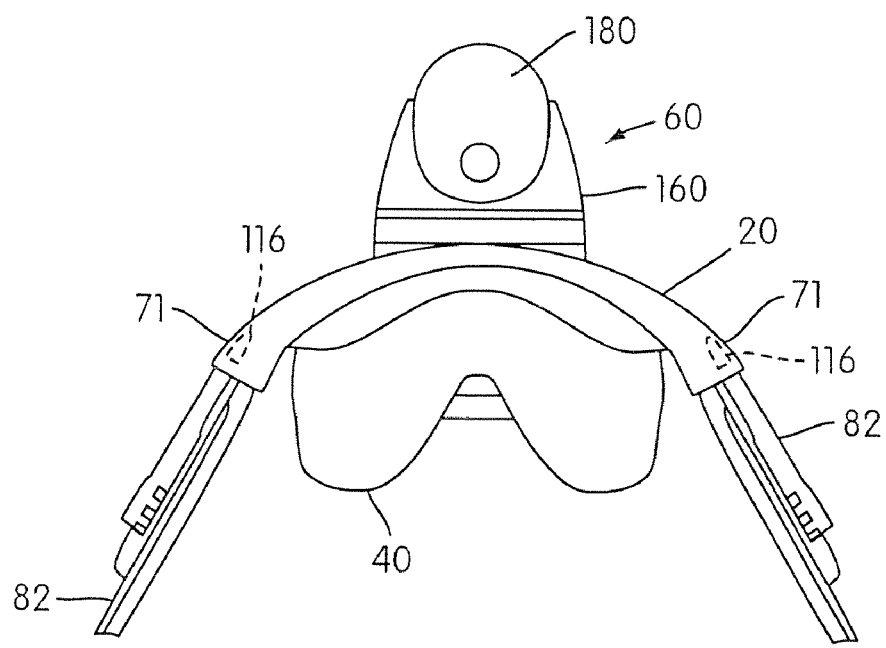
FIG. 4 is a partial top plan view of the nasal mask assembly of FIG. 1.

As shown in FIGS. 1-4, a nasal mask assembly 10 according to one preferred embodiment of the present invention includes a frame 20 and a cushion 40 that is preferably detachably connected to the frame 20. Alternatively, the cushion 40 can be permanently attached to the frame 20 using, e.g., co-molding and/or over-molding techniques, glue and/or mechanical fastening means. A swivel elbow assembly 60 and a headgear assembly 80 can be attached to the frame 20. FIG. 1 shows the nasal mask assembly 10 generally as it is intended to be mounted onto a human head. Of course, the depiction in FIG. 1 is slightly spaced away from the head, or "floating", for ease of understanding. FIG. 1b shows the headgear assembly laid flat with the frame 20 removed therefrom. FIG. 2 illustrates the mask assembly 10 from the left side view, FIG. 3 illustrates a front view thereof, and FIG. 4 illustrates a top view thereof. In FIGS. 2-4, the rear portion of the headgear assembly 80 has been removed for clarity.

Mask Frame

Figure 5:
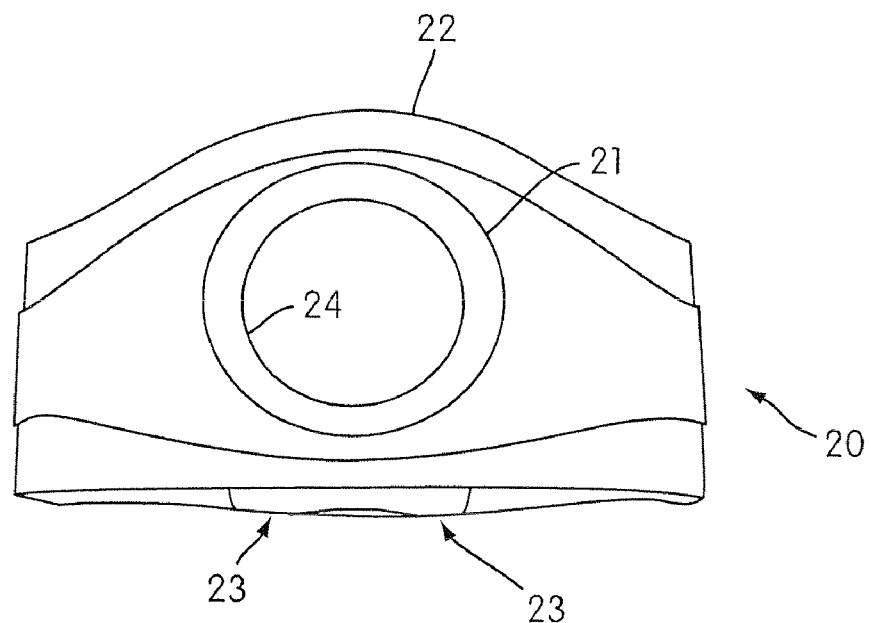
FIG. 5 is a front perspective view of a frame component of the nasal mask assembly of FIG. 1.
Figure 5A:
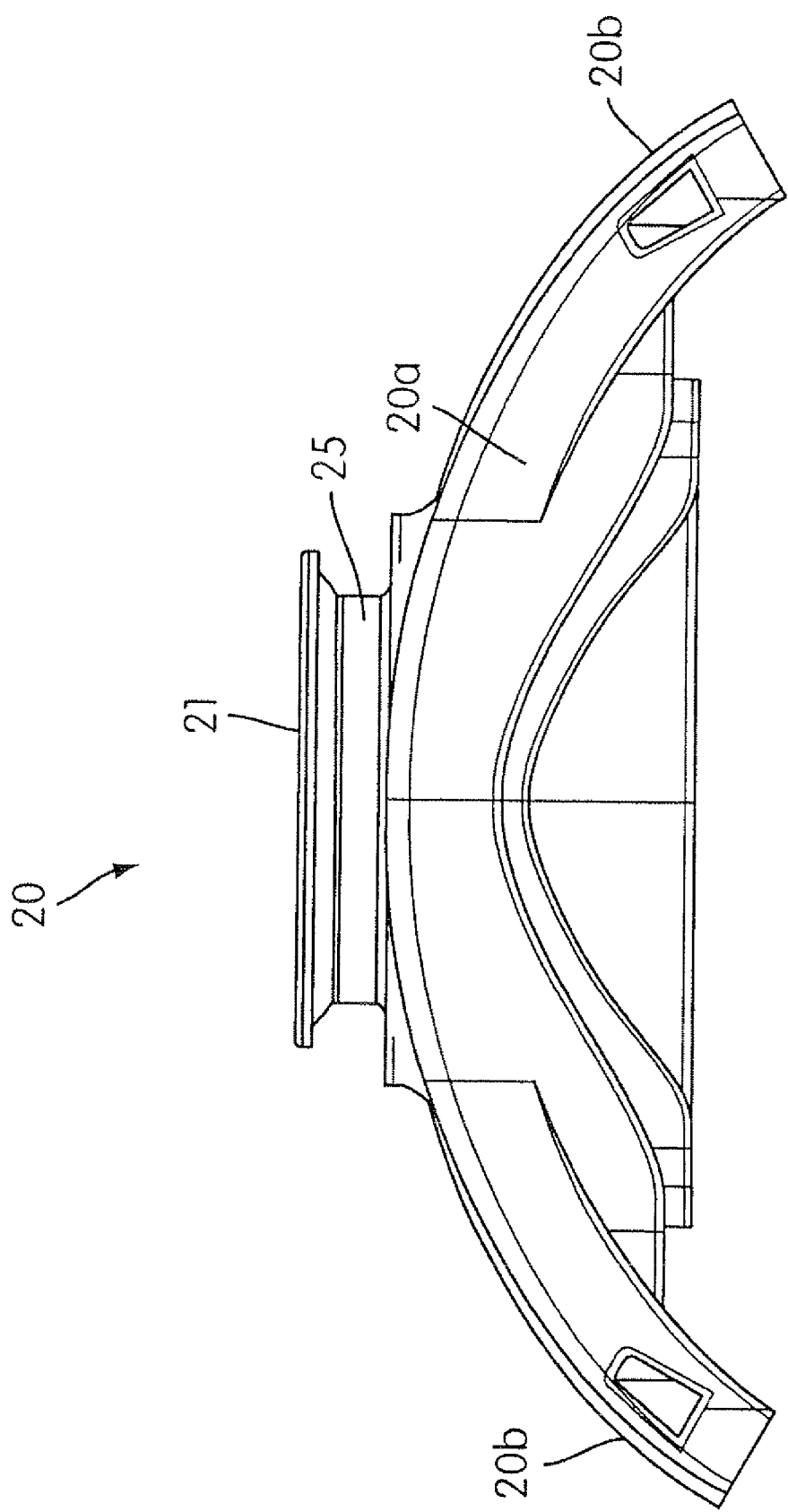
FIG. 5a is a top view of the frame of FIG. 5.

As shown in FIG. 5, frame 20 includes an elongated body 22 having a central bore 24 for connecting to the swivel elbow assembly 60. FIG. 5a is a top view of the frame 20 in which the cushion 40, the elbow assembly 60 and the headgear assembly 80 have been detached. The frame 20 includes a main body 20a, which is designed to accommodate the cushion 40, and a pair of side frame members 20b that are preferably formed in one piece with the main body 20a of the frame 20. FIG. 5a shows that both side frame members preferably have the same configuration. The main body 20a and the side frame members 20b have been designed to have a curvature that generally follows the facial contour of the patient's face on each side of the nose. In accordance with one embodiment of the invention, the curvature follows a smooth transition from the two side members having an inclusive angle of 120°. With the cushion 40 in place, the main body 20a is spaced away from the patient's face in the nose region to prevent contacting the patient's nose, while the side frame members 20b are generally parallel the cheek regions. A space is maintained between each side frame member 20b and the cheek of the patient since contact is not desired in this area. However, if desired, the side frame members 20b may be constructed to include a comfort feature such as pad structure that engages the cheek regions of the patient. Such a pad can have the advantage of assisting in supporting the cheeks when pressure is applied in treatment mode.

Figure 5B:
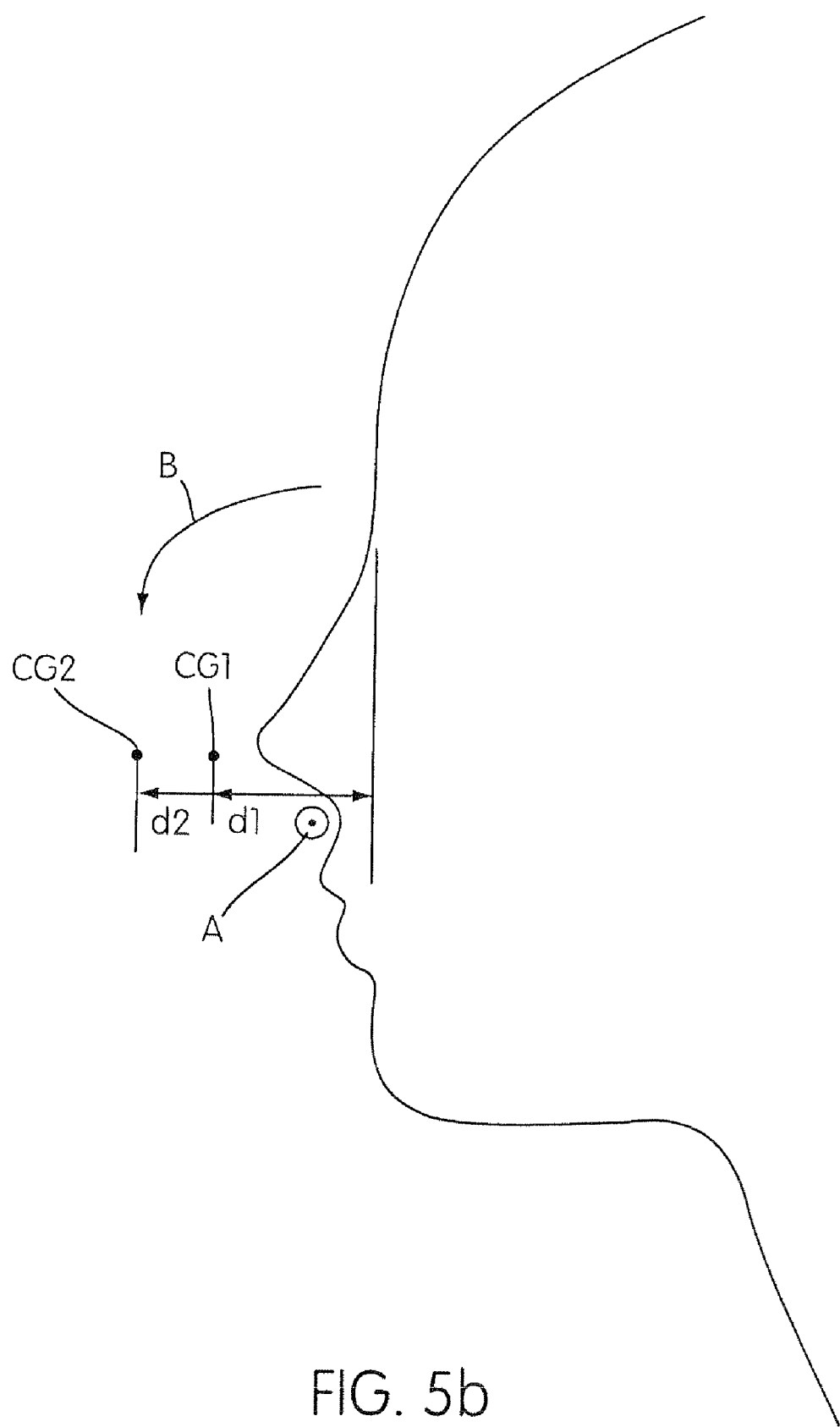
FIG. 5b is a schematic view showing various forces acting on the nasal mask assembly which may affect a patient.

Based on the curved design of the frame 20, and other features, the center of gravity CG1 (FIG. 5b) of the mask assembly 10 can be formed closer to the face of the patient. As such, rotative torque or moment created in the vertical plane due, for example, to the weight of the mask assembly can be reduced. For example, if the patient is sitting in the upright position as shown in FIG. 5b, the weight of the mask assembly 10 can produce torque about an axis A (into the page) that is transverse to the patient's nose in the horizontal plane. That torque can produce forces tending to rotate the mask assembly 10 in the direction of arrow B about the axis A which is generally positioned along the upper lip region of the cushion. Such torque may result in patient discomfort along the upper lip region and/or reduced sealing around the lower bridge region of the nose and/or at the cheek region. Specifically, a center of gravity CG1 located close to the face can produce less torque than a mask having a center of gravity CG2 that is further away from the face. This is because the distance d1, d2 between the center of gravity CG1, CG2 and the face defines the lever arm used to measure torque (torque=force×lever arm distance). Accordingly, torque can be reduced if the force or the lever arm distance is reduced. Similar torques can be created if the patient is lying on his or her side as well. The torque is affected by the geometry of the elbow, including such features as its length and height in relation to the cushion. It is desirable to minimise the effective lever arm length of the assembly which depends amongst other things on the configuration of the elbow.

Figure 5C:
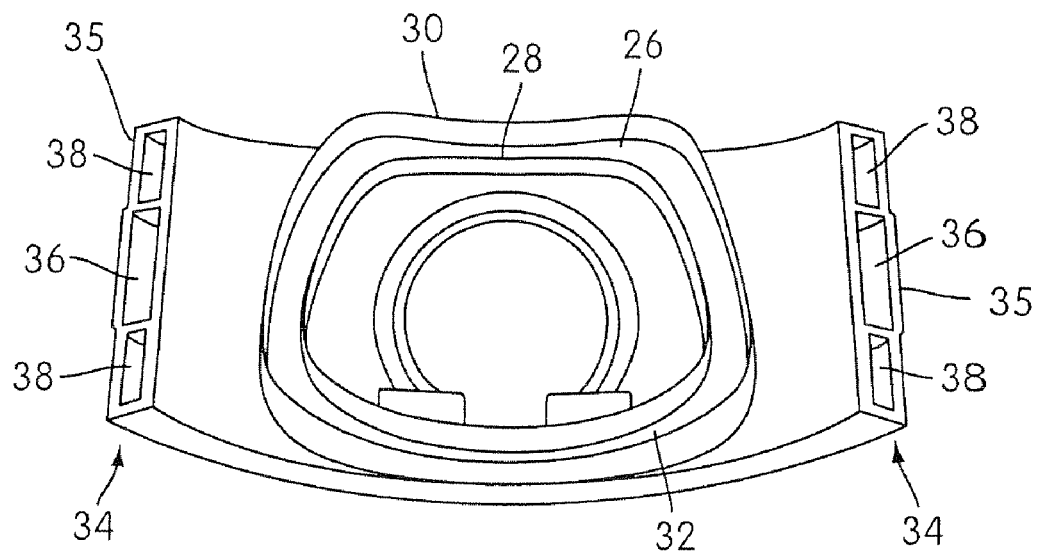
FIG. 5c is a rear perspective view of the frame of FIG. 5.

Other factors which contribute towards reducing the distance between the center of gravity of the mask assembly and the face include design of the cushion 40, the design of the frame 20, and the design of the elbow assembly 60. Another source of torque, which may affect stability of the mask, is the connection of the elbow assembly 60 to the gas delivery tube. In effect, the gas delivery tube may impart a force on the elbow assembly 60, which in turn may create a torque tending to shift the mask assembly with respect to the patient. The amount of torque applied to the patient due to the connection between the elbow assembly and the gas delivery tube can be reduced using the elbow assembly 60 discussed below in relation to FIGS. 16a-19c-2. In short, the lever arm of the elbow assembly can be effectively reduced because the elbow assembly is designed to be connected directly to a gas delivery tube 310 (FIG. 26), without the need for an intermediate swivel connector member 300 (FIGS. 6b and 23) between the elbow assembly and the gas delivery tube 310, as is currently used in some prior art. Alternatively, a swivel may be incorporated within the tube. In this way, an additional degree of freedom of movement may be added without increasing the undesirable torque. Also, because the cushion 40 is designed to distribute pressure at least along the lip and cheek regions of the cushion 40, the possibility or tendency to rotate in the vertical plane is further reduced. Moreover, each of the cheek regions of the cushion 40 defines a relatively large contact pressure receiving surface that is elongated in the vertical direction and widened in the horizontal direction. As such the cushion 40, at least in the cheek regions, resist rotational movement in the vertical and/or horizontal planes, which helps maintain the cushion 40 in a consistent position on the patient. More details of the cushion 40 are described below in relation to FIGS. 24*a*-25*i*. Referring to FIG. 5*c*, the frame 20 includes a channel 26 having a generally trapezoidal shape for connecting to the cushion 40. The channel 26 includes an inner wall 28, an outer wall 30 and a channel floor 32. The channel 26 will be described in further detail below.

FIG. 6*a* shows a frame 20 and elbow assembly 60 that is slightly different than the frame 20 and elbow assembly 60 shown in FIGS. 1-5*c*. Although the main differences between the embodiments reside in the elbow assembly 60, there are other differences between the frames 20, cushions 40, etc., as will be readily seen by comparing the various figures, or understood in conjunction with the description in various sections below. Like elements are indicated with like reference numbers.

In FIGS. 6*a* and 6*b*, the elbow assembly 60 is attached to the mask 20 using a C-clip 23 (FIG. 6*b*) that can be expanded and contracted to fit within a circumferal groove 25 provided on a portion of the elbow assembly 60 that protrudes into the frame 20 using a mechanism similar to that provided on ResMed's ULTRA MIRAGE® mask and as described in U.S. Pat. No. 6,691,707 (Drew et al.). An exploded view of the cushion 40, the frame 20, the elbow assembly 60 and the gas delivery tube is shown in FIG. 6*b*. The C-clip 23 has a surface that engages the inside surface of the frame 20 to prevent unwanted disconnection between elbow assembly 60 from the frame 20. The elbow assembly 60 may also include one or more vent openings 61 open to atmosphere, for example, for gas washout of exhaled carbon dioxide, among other things. The vent openings 61 are structured so that treatment pressure will be maintained within the nasal cavity. The vent openings 61 may be covered with a shell member 65 which is resiliently and removably clipped onto an outer surface of the elbow assembly 60. The vent openings 61 in FIG. 6*a* are visible through the clear shell member 65. Details of the shell member 65 and the C-clip are described in the ResMed's U.S. Pat. Nos. 6,532,961, 6,691,707 or PCT Application No. PCT/AU00/00097 (WO 00/78384), all of which are incorporated herein by reference.

As shown in FIG. 6*a*, the inner wall 28 of channel 26 preferably extends away from the frame 20 to a distance that is greater than the distance that the outer wall 30 extends away from the frame 20. FIGS. 5*c* and 32*d* also show that the inner wall 28 extends away from the frame 20 a distance that is greater than the distance over which the outer wall 30 extends away from the frame 20. As shown in FIG. 32*d*, the thickness of the inner wall 28 is in the range of about 1-2 mm, preferably 1.4 mm, the thickness of the outer wall 30 is in the range of about 1-2 mm, preferably 1.4 mm, and the distance between the tops of the inner and outer walls 28, 30 is in the range of 0.5-10 mm, preferably 2 mm. Further, as shown in FIG. 32*d*, the width of channel 26 between the upstanding surfaces of the inner and outer walls 28, 30 that face each other is in the range of about 2-10 mm, preferably 5 mm.

By adopting this relative distance between inner wall 28 and outer wall 30, the engagement of the cushion 40 to the frame 20 is facilitated. As the cushion and mask frame are moved together, the inner wall 28 provides a visual and/or tactile cue to cushion alignment and then will facilitate the continuance of the engagement process by guiding the edge of the side wall or central portion 215 (FIGS. 24*e* and 27*a*) of the cushion 40 into channel 26, as will be more fully explained with reference to FIGS. 27*a*-29*d* and 32*a*-1-32*c*-2. The shape of the channel 26, e.g., a generally trapezoid shape as seen in FIG. 5*c*, is selected so as to achieve guidance to correct cushion orientation relative to the channel 26 without the need for additional guide pieces as would be the case should the channel 26 have a more symmetrical shape such as an equilateral triangle, circle, square or rectangle. Nevertheless, the cushion channel 26 could adopt any of these shapes.

Figure 7:
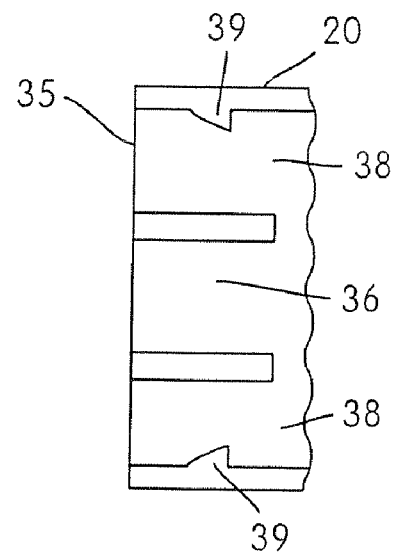
FIG. 7 is a partial sectional view of the frame of FIG. 5.

As seen in FIGS. 5*c* and 6*a*, the frame 20 includes a locking clip receiver assembly 34 positioned on each side of the frame 20 for connecting to a respective locking clip 82 (FIGS. 9*a* and 10*a*) of the headgear assembly 80. Each locking clip receiver assembly 34 includes an engagement face 35 (FIG. 5*c*), a central support slot 36 and two locking slots 38 positioned on opposite sides of the central support slot 36. The central support slots 36 and locking slots 38 have a generally rectangular cross-section. Each of the locking slots 38 includes a locking flange 39 (FIG. 7) positioned on an outer wall thereof for engagement with a respective locking tab 116 (FIGS. 9*a* and 9*b*) of one of the locking clips 82, as described below. The channel 38 may be provided with a slot 71 (FIG. 10*a*) in the outer wall of the frame 20 in addition to or in replacement of the locking flange 39 (FIG. 7). The slots 71 on the bottom of the frame 20 can be seen in FIG. 5*a*, while FIG. 4 shows the slots 71 from the top of the frame 20. The slots 71 need not extend through the side walls of the frame 20.

Headgear Assembly

FIG. 1*b* shows headgear assembly 80 in accordance with an embodiment of the invention, without the frame 20 or cushion 40. In FIG. 1*b*, the headgear assembly is shown laid flat.

The Straps and Yokes

Referring to FIGS. 1-4, headgear assembly 80 includes a pair of front straps 84, with the left and right front straps 84 preferably being mirror images of each other. Each front strap 84 is in the general form of a "Y" and has a front strap end 86, a top strap end 88 and a rear strap end 90 all formed in one piece or otherwise interconnected together by mechanical fastening or the like. The straps are made from laminated fabric and foam. One commercially available material is "Breath-O-Prene"™ manufactured by Accumed Inc., USA. Fastening of the straps may be assisted by use of a hook and loop material such as VELCRO®, however, the straps need not include hook and loop fasteners since the straps are fastened to the frame 20 using locking clips 82, as more fully described below. As shown in FIGS. 1-3 and 8, a yoke 92 is attached to each front strap 84. Each yoke 92 has the same general shape as the corresponding front strap 84 and has a front end 94, a top end 96 and a rear end 98. Each yoke 92 is constructed of a somewhat rigid material, e.g., plastic, and has a thickness in the range of 0.3-2.0 mm, preferably 1 mm. Examples of the plastic include nylon 11 or polypropylene. The yoke 92 is attached to the corresponding front strap 84 with adhesives, stitching, or other known attachment mechanisms. The strap and yoke arrangement can have different flexibilities in different directions, for example being stiff in a first direction (e.g., to resist the deformation due to the weight of the swivel elbow, associated conduits, etc.), but flexible in a direction generally orthogonal to the first direction. Upon donning the mask on the user's head, the relative stiffness of the yokes helps position the frame and cushion in the correct position on the user. Although having the same general shape as the front straps 84, the top ends 96 and rear ends 98 in this embodiment do not extend as far as the top strap ends 88 and rear strap ends 90 of the front straps 84.

However, in another embodiment, the top end 96 may be extended along the entire length of the top strap 88 and be formed integrally or in one piece with a connector element 128 (FIG. 1). The yokes 92 are also narrower than the front straps so that when they are attached together, the softer material of the front straps 84 extends beyond the more rigid material of the yokes 92, thereby preventing or at least reducing the opportunity for contact between the user and the more rigid material of the yokes 92 that could cause irritation or discomfort. While the straps and associated yokes are formed from a multilayer construction, e.g., two layers, the strap 84 and yoke 92 could be formed of a single material, so long as patient comfort and the appropriate rigidity/flexibility are maintained.

The yokes 92 add to the rigidity of the straps 84 in certain planes and directions, which assists in stabilizing the mask assembly 10 on the head of the patient during use. In other planes and directions, the yoke and strap assembly has a different rigidity. For example, the strap and yoke should be able to resist bending or curling towards or away from the patient's face. In general, the strap 84 and yoke 92 should be able to maintain their positions with respect to the head of the patient when the straps 84 and yokes 92 are connected to the frame 20. Moreover, the mask frame 20 need not be provided with a forehead support assembly, which may further increase the comfort of the patient since the patient's field of view is less obstructed as compared to masks with forehead supports. Of course, forehead supports of the type described above may be provided if desired for additional stability or comfort. Also, the mask frame 20 need not be provided with a chin strap, although a chin strap may be provided if desired for additional stability or comfort. In addition, beyond removal of the forehead support, the shapes of the straps 84 and yokes 92 are selected to avoid interference with the patient's field of view. In particular when fitted, the front ends 94 of each yoke 92 are connected to the frame 20 below the patient's eyes, and preferably extend along a curved arc resting across the cheek regions. The top end 88 of each strap 84 and the top end 96 of each yoke extend away from the intersection of the Y along the temple region of the patient's head. The rear end 98 of the yoke 92 and the rear end 90 of the strap 84 are curved downwardly and around the ear of the patient for connection with the rear strap member 138, as more fully described below. Due to the rigidity provided by the yokes 92, the straps 84 are better able to maintain a predetermined shape. On the other hand, a certain degree of flexibility of the yoke 92 and strap 84 is provided such that variations in patient physiology can be accommodated to a certain degree. The thickness of the yoke can also vary across its profile to modify flexibility characteristics, for example, thicker regions may be stiffer.

Figure 8:
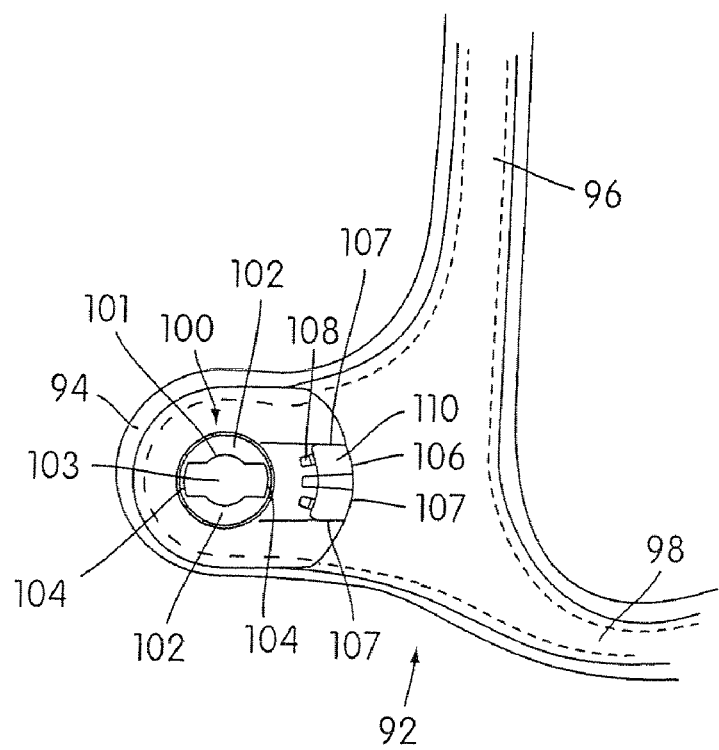
FIG. 8 is a side view of a left side yoke of the nasal mask assembly of FIG. 1.
Figure 8A:
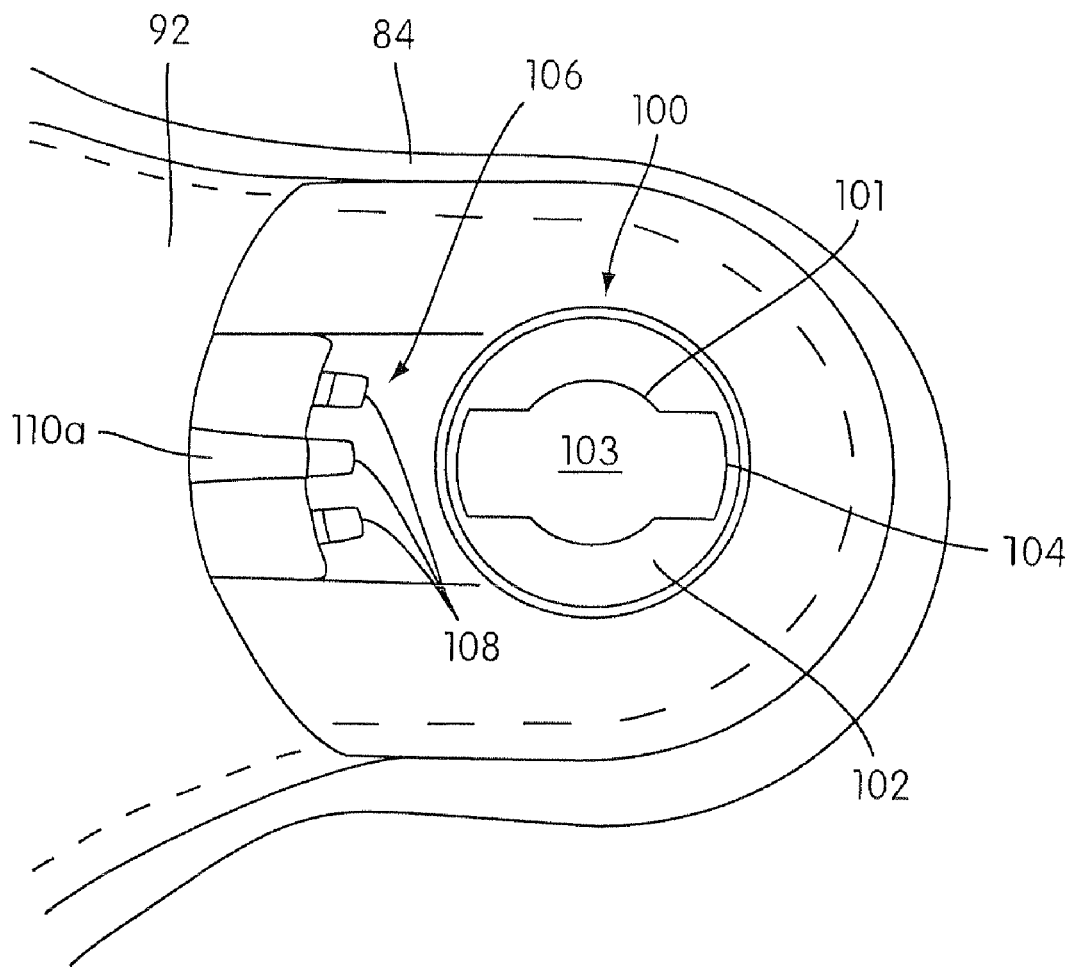
FIG. 8a is an enlarged view of a right side yoke according to another embodiment of the present invention.

As shown in FIG. 8, each yoke 92 has a mounting flange 100 positioned on the front end 94. The mounting flange 100 has an aperture or keyhole 101 leading to a bore 103, see FIG. 8*a*. Two semi-annular flanges 102 are separated from each other by slots 104. A radial inner surface of the semi-annular flanges 102 forms the central bore 103. The yoke 92 also has a spring tab 106 positioned rearward of the mounting flange 100 with a front portion of the spring tab connected to the yoke 92 and a rear portion separated from the yoke 92 by space 107 to be able to flex with respect to the yoke 92 when pressure is applied to the spring tab 106. The spring tab 106 preferably has a plurality of raised teeth 108 positioned in an arc about an axis of the mounting flange 100. The spring tab 106 also has a textured surface 110 (FIG. 8) or a raised positioning member 110*a* (FIG. 8*a*) at its free end to assist the user in locating, engaging and manipulating the spring tab 106. FIG. 8*a* is an enlarged view of a right side yoke 92 and strap 84, like that shown in FIG. 8, to better show details of yoke 92, including the manner in which the yoke 92 is stitched to the head strap 84. Other fixing mechanisms such as locking or friction may be used.

The Locking Clip

Figure 9A:
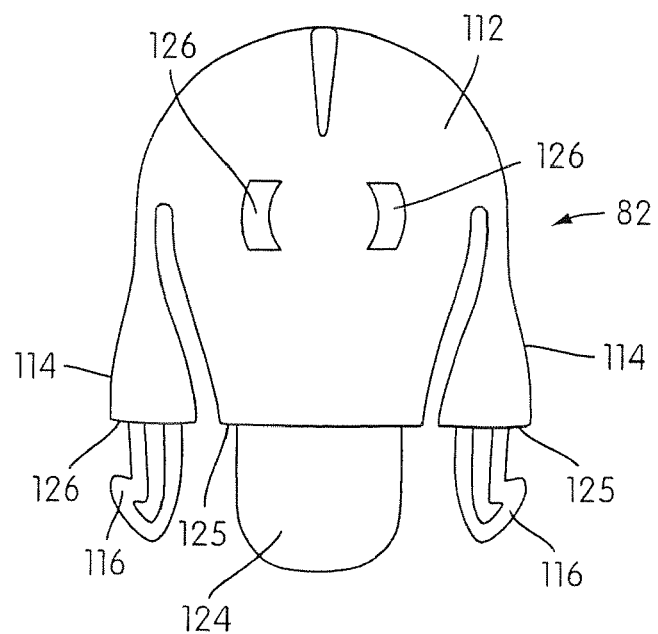
FIG. 9a is a top view of a locking clip of the nasal mask assembly of FIG. 1.
Figure 9B:
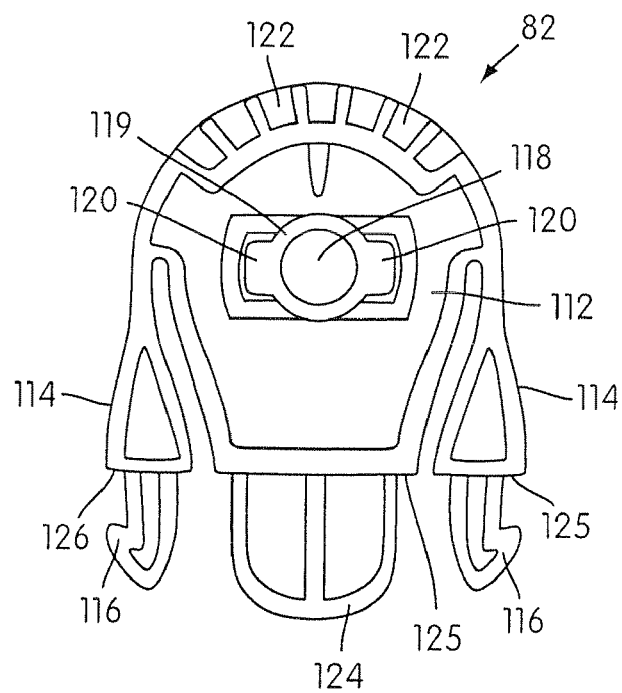

The locking clip 82 is adjustably attached to each mounting flange 100. As shown in FIGS. 9*a* and 9*b*, each locking clip 82 includes a main body 112. Two spring arms 114 are attached to opposite sides of the main body 112 and extend away from the main body in a generally parallel manner. A latch hook 116 is attached to a free end of each spring arm 114.

Figure 10A:
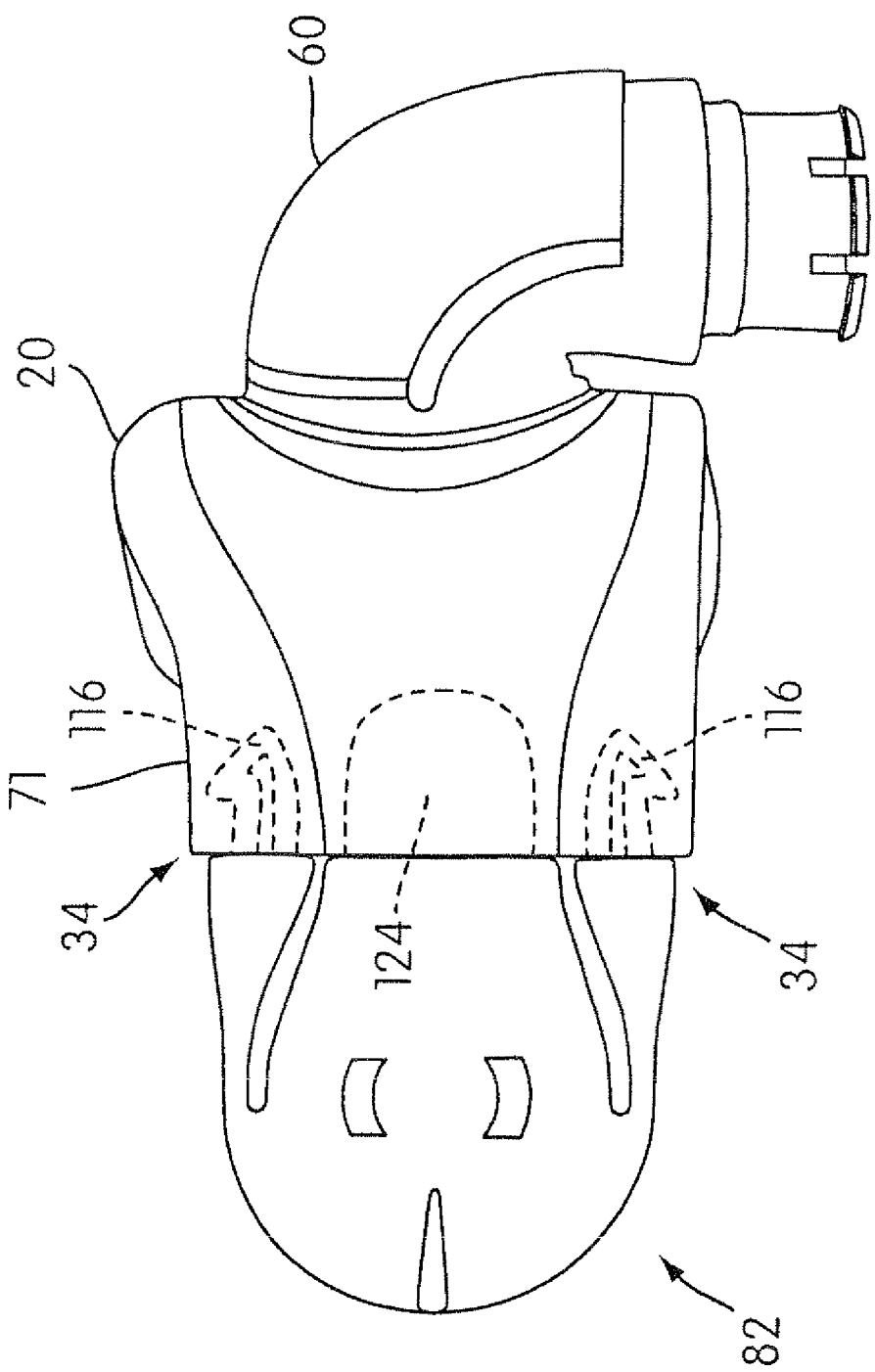
FIG. 10a is a side view of a clip and frame in a nearly fully connected condition, according to the present invention.

As shown in FIG. 10*a*, the clip 82 can be inserted into releasable engagement with the locking clip engagement receiver 34 of the frame 20. In FIG. 10*a*, only one clip 82 is shown and the clip 82 is not assembled to the yoke 92. Each latch hook 116 is received within a respective channel 38 (FIG. 5*c*) of the frame. In FIG. 10*a*, the distal ends of the latch hooks 116 are shown in a position just before they outwardly flex into the respective recesses 71 of the channel 38. FIG. 4 shows the distal ends of the latch hooks in the engaged position within the recesses 71. Of course, the clip 82 or at least the latch hook 116 thereof could be formed in the frame 20, and the channel 38 or at least the recess 71 could be formed on the strap and/or yoke.

FIGS. 4 and 10*a* also show that the outward surfaces of the locking clip 82 and the frame 20 preferably form a generally continuous surface, which is not interrupted when connected. Preferably, the locking clip 82 is as wide as the frame 20 at each end, which facilitates tactile location of the locking clip by the patient. The spring arms 114 are designed to flex within the plane of the locking clip main body, which further improves the ease by which the locking clips 82 are attached and detached. This positioning improves the ergonomics of the release mechanism. The patient's thumb and an opposing finger can be used to readily locate and operate the locking clips 82. Also, because of their increased size, patients with minimal dexterity can operate the locking clips 82. Further, the locking clips 82 are connected to the strap 84/yoke 92 so that length adjustment between the locking clips 82 and the strap 84/yoke 92 is not necessary.

Figure 10B:
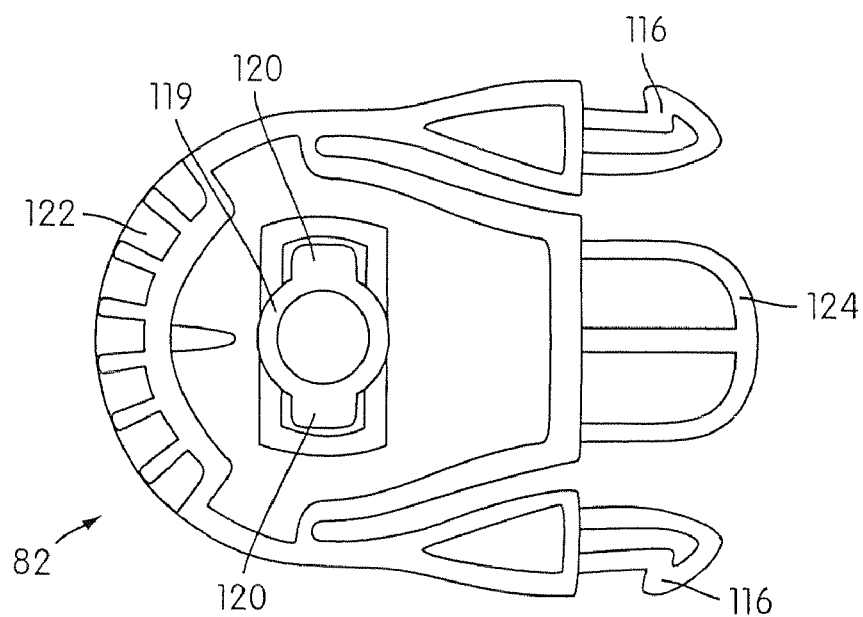
Figure 10C:
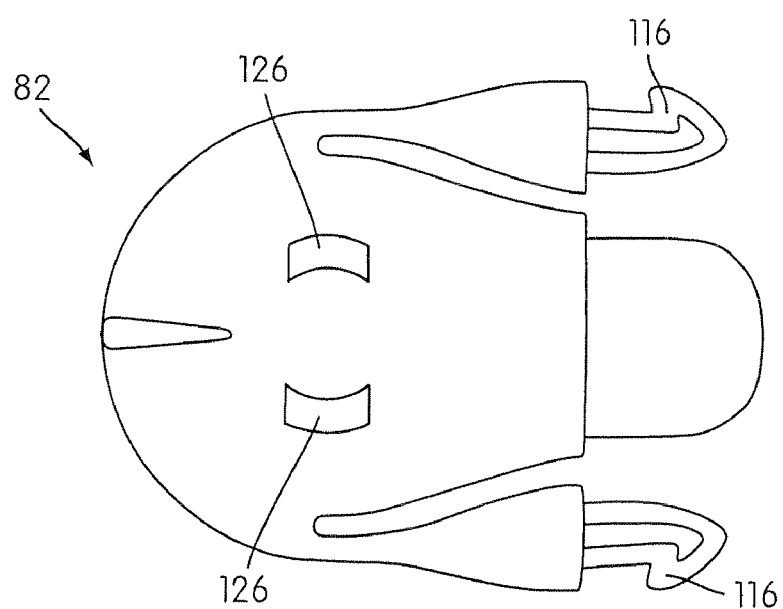
Figure 10D:
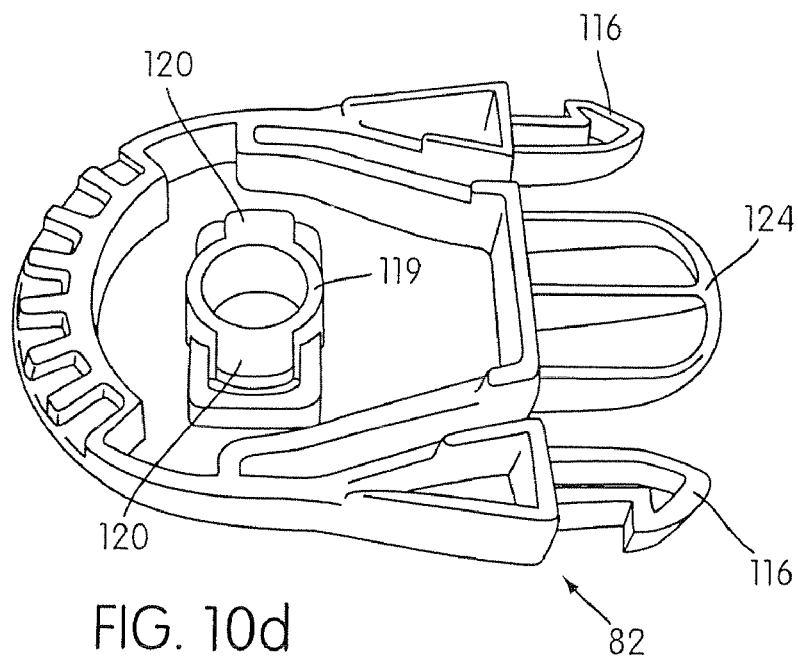

The locking clip 82 includes a retaining flange 118 (FIG. 9*b*) extending transversely outward from the main body 112. The retaining flange 118 has a central hub 119 extending along an axis of the retaining flange 118 and two retaining tabs 120 extending transversely from the central hub 119 on opposite sides of the central hub 119. FIGS. 10*b-d* show more details of the locking clips 82 shown in FIG. 10*a*, which are similar to features shown in FIGS. 9*a* and 9*b*. While the locking clip 82 has been shown to be separate from the yoke 92, it is understood that the clip and yoke 92 could be formed in one piece if relative movement and/or detachment between the two is not required. Conversely, the clip 82 and frame 20 can be formed as an integral unit, and the clip portion could be connected to the yoke.

Figure 10E:
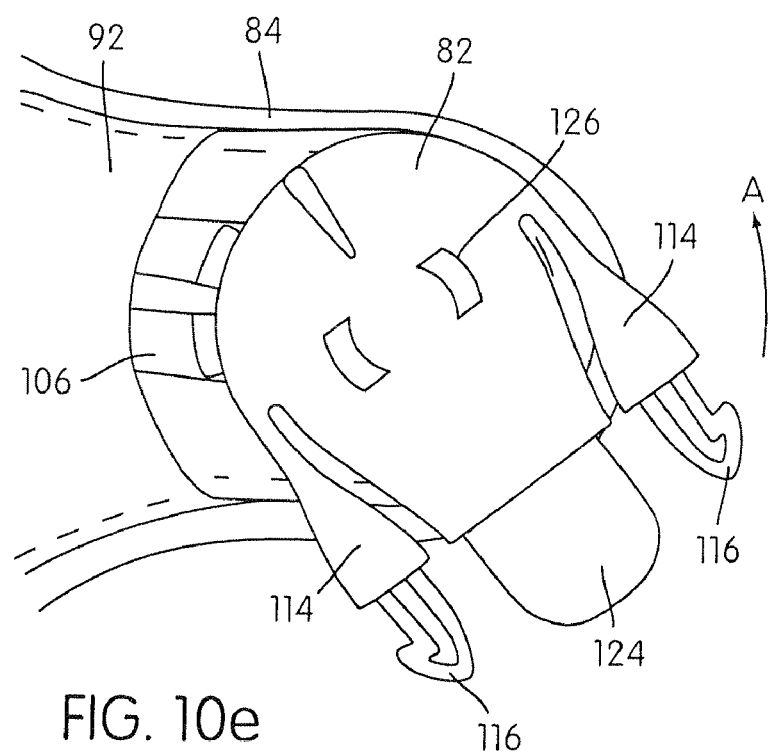
FIGS. 10e-10g illustrate the clip and yoke of the present invention in various connected positions.
Figure 10F:
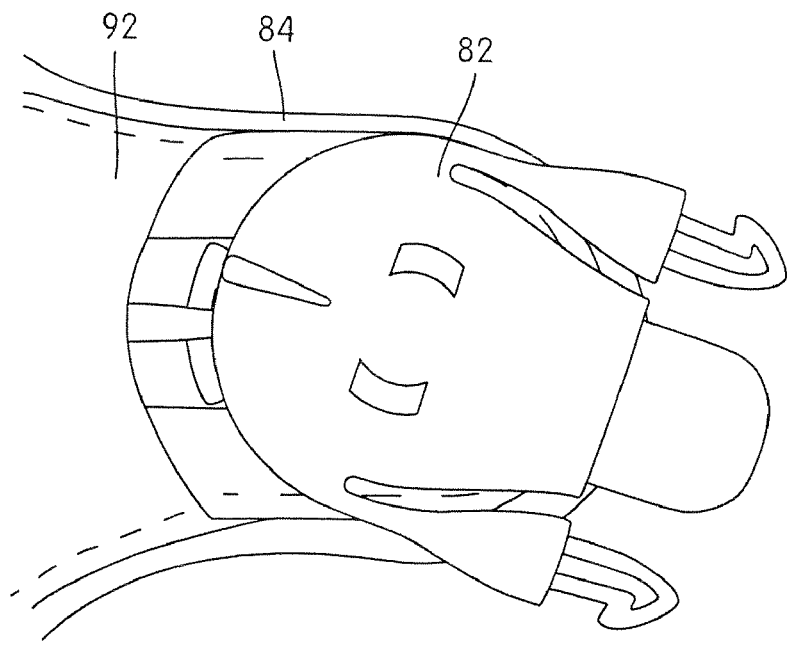
Figure 10G:
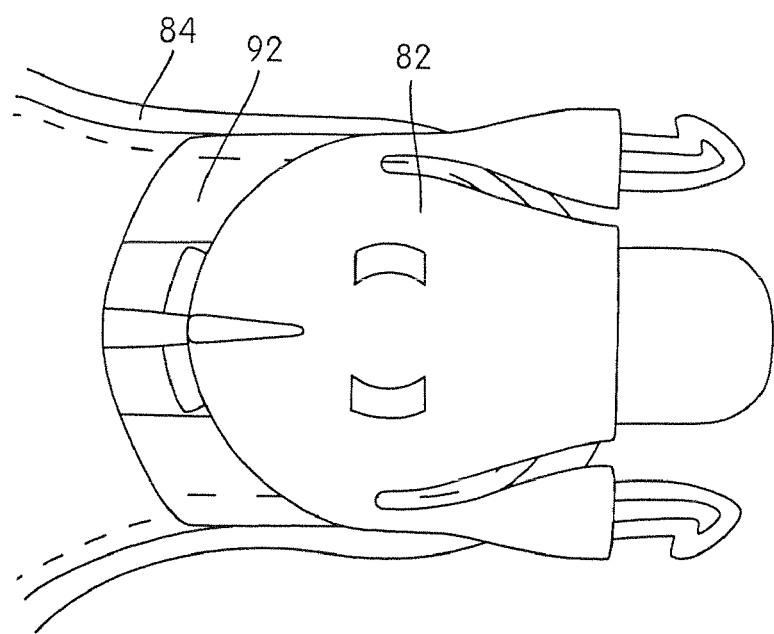

The retaining flange 118 is sized and shaped such that the retaining tabs 120 can be aligned with the slots 104 and the retaining flange 118 axially inserted into the mounting flange 100 of the yoke 92. The central hub 119 is sized to have a close tolerance with the central bore 103 so that the locking clip 82 and yoke 92 are rotationally supported with one another. Once the retaining flange 118 has been inserted into the mounting flange 100, the locking clip 82 can be rotated with respect to the yoke 92 such that the retaining tabs 120 engage an inside surface of the flanges 102, thereby axially locking the mounting clip 82 to the yoke 92. FIGS. 10*e-g* show the locking clip 82 in various positions with respect to the yoke 92. In FIG. 10*e*, the tabs 120 of the clip 82 have been inserted through the openings 104 of the yoke 92, and the clip 82 has been rotated slightly along the direction of arrow A such that the upper surfaces of the tabs 120 snugly engage the inside surfaces of the semi-annular portions 102. When the clip 82 is attached such that the flexing arms 114 are positioned approximately 90 degrees with respect to the front end 94 of the yoke 92, the clip 82 can be removed from the yoke 92. In this embodiment, there are two positions in which the removal can occur, and both of these positions are selected such that they would not occur when the mask is in normal use; otherwise the clips 82 could be inadvertently detached from the yokes 92. FIGS. 10f and 10g show the clip 82 in different rotational orientations with respect to the yoke 92.

As seen in FIGS. 9b and 10b, the locking clip also has a plurality of raised teeth 122 positioned in an arc about an axis of the retaining flange 118. The teeth 122 are constructed and arranged so as to engage the teeth 108 on spring tab 106. Once the spring tab 106 has been depressed to lower teeth 108, the locking clip 82 can be rotated to a desired position with respect to the yoke 92. The spring tab 106 can then be released so that teeth 108 engage teeth 122 in the desired position (within a pitch of the teeth) and rotationally lock the locking clip 82 with respect to the yoke 92. In accordance with one embodiment, the teeth 108 and 122 can be configured so that when a predetermined torque is applied to the locking clip 82, the teeth 122 will automatically force the teeth 108 and spring tab 106 downwardly to allow rotation of the locking lip 82 until the torque is removed and the teeth 108 re-engage the teeth 122. The locking clip 82 can thus be rotationally adjusted with respect to the yoke 92 within an angle of approximately 50-100°, and preferably 75°, depending on the position of engagement between teeth 108 and teeth 122. The angle of available rotational adjustment can be altered as desired by altering the number and positioning of teeth 108 and 122. The adjustment angle range reflects the relative cushion positions required on the face. Rotational adjustment with a toothed system as described above allows easy adjustment by the patient and allows a broad range of positions to accommodate a wide range of patients' faces. For example, the patient may adjust both locking clips 82 to have the same angle with respect to the yokes 92. Alternatively, the patient may adjust the locking clips 82 such that the locking clips 82 have different respective angles with respect to the yokes 92. The toothed system allows the patient to easily set and reproduce the desired angle for each locking clip 82. For example, the toothed system may allow relative movement between each locking clip and its respective yoke in, for example, five positions, which should accommodate most faces. Of course more or less than five positions could be used instead, depending on application. Moreover, once it is determined that a particular angle for each locking clip 82 with respect to the yokes 92 is desired, the mask system may include a non-adjustable clip arrangement which fixes the rotational position of the locking clips 82 with respect to the yokes 92. The teeth are large enough for the patient to easily determine the relative positions of the locking clip with respect to the yokes.

Further, the spring tab 106 is configured and positioned such that the patient cannot inadvertently depress the spring tab 106, e.g., by rolling over on the locking clip/yoke during sleeping, to cause the locking clip 82 to move relative to the yoke 92. For example, as shown in FIGS. 10e-10g and FIG. 36 (a different embodiment), the locking clip 82 extends further outwardly from the yoke 92 than the spring tab 106. That is, the spring tab 106 is positioned lower than the outer edge of the locking clip 82. Thus, the positioning of the locking clip 82 with respect to the spring tab 106 prevents inadvertent actuation of the spring tab 106. Moreover, the spring tab 106 is connected to the yoke 92 such that the yoke 92 can flex toward and away from the spring tab 106 without disengaging the teeth 108 of the spring tab 106 from the teeth 122 of the locking clip 82.

Alternative adjustment assemblies may be achieved by simple reversal of some or all of the sub-assemblies. For example, the central hub 119 might be located on the yoke 92 while its reciprocal yoke central bore 103 may be located on the locking clip 82. In a similar way, each sub-assembly and its reciprocal may be reversed. Alternatively, the yoke 92 and locking clip 82 may be adjustably connected by way of a screw or clamping mechanism, e.g., a part that may be separate from the yoke and clip, which can be used to selectively connect the yoke 92 and clip 82 in a plurality of desired positions. In addition, the central bore 103 can be shaped in any manner that allows detachment and attachment between the yoke and the clip. Also, a system of replacement yokes that would allow a fixed angle with respect to the locking clip may be used.

The locking clip 82 also includes a central support tab 124 extending outward from the main body 112 between and generally parallel to spring arms 114. The central support tab 124 is configured to have a close fit with the central support slot 36, so that when the central support tab 124 is inserted into the central support slot 36, little rotational, rocking or side to side movement is permitted between the locking clip 82 and the locking clip receiver assembly 34. Central support tab 124 is longer than arms 114 to assist with alignment into the frame. The locking clip 82 also has an engagement face 125 that engages engagement face 35 (FIG. 5c) when the locking clip 82 is inserted into the locking clip receiver assembly 34 to provide additional support for the locking clip 82. The latch hooks 116 and/or the central support tab 124 may have tapered widths and/or thicknesses to facilitate entry into slots 36, 38. Also, the latch hooks 116 and/or central support tab 124 may have rounded or contoured edges to facilitate entry into slots 36, 38. Further, the central support tab 124 may have a groove that engages a protrusion provided in the central support slot 36 to facilitate entry of the central support tab 124 into the central support slot 36. Alternatively, the central support tab 124 may have a protrusion that engages a groove provided in the central support slot 36.

When the locking clip 82 is inserted into the locking clip receiver assembly 34, the spring arms 114 are forced toward one another as the latch hooks 116 are inserted into recesses 71 (FIG. 4) or ride up and over the locking flanges 39 (FIG. 7). Once the latch hooks 116 have cleared the locking flanges 39 or recesses 71, the spring arms 114 can spring outward, providing a locking engagement between the latch hooks 116 and the locking flanges 39 and/or recesses 71. Sufficient clearance is provided in locking slots 38 to allow the necessary movement of the latch hooks 116 to clear the locking flanges 39.

In this manner, the respective left and right front strap assemblies, including front straps 84, yokes 92 and locking clips 82, can be attached to the frame 20 and the yokes 92 and front straps 84 rotationally adjusted with respect to the frame 20 within an angle of approximately 50-100°, and preferably 75°.

In a preferred embodiment, the locking clip 82 is a unitary plastic piece formed by injection molding. Examples of the plastic include nylon, acetal, polycarbonate, and polypropylene. In one embodiment, the retaining tabs 120 are formed during the molding process by mold projections that leave bores 126 extending through the main body 112 of the locking clip 82, thereby separating under surfaces of the retaining tabs 120 from the main body 112.

Magnetic Interconnection

FIGS. 33-37 illustrate an alternative embodiment for removably coupling the frame 420 and the headgear assembly 480. Specifically, the frame 420 and the yokes 492 are structured such that the yokes 492 may be magnetically coupled to the frame 420.

Figure 33:
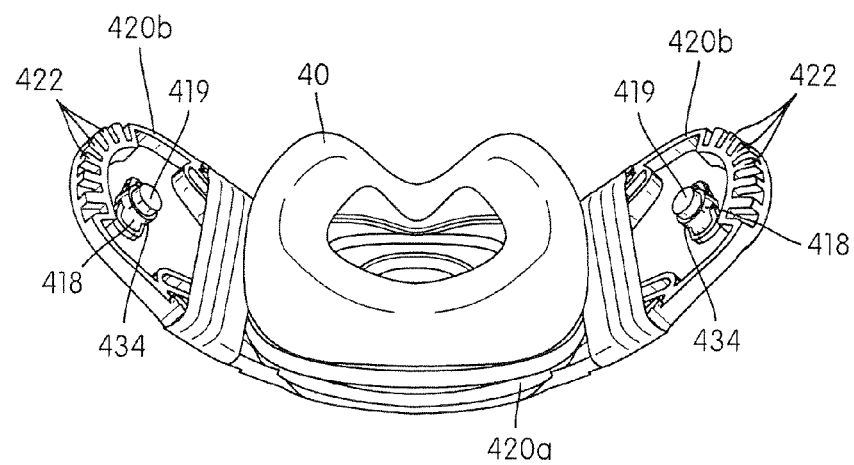
FIG. 33 is a perspective view of another embodiment of a frame of the nasal mask assembly.

As shown in FIG. 33, the frame includes a main body 420a and a pair of side frame members 420b. Similar to the embodiment of frame 20, the main body 420a is structured to be removably coupled with the cushion 40. Each side frame member 420b includes a first connector portion 434 for connecting to a second connector portion 435 provided by the yoke 492 of the headgear assembly 480. In the illustrated embodiment, the first connector portion 434 includes a retaining structure 418 that extends outwardly from the side frame member 420b. The retaining structure 418 is structured to retain a magnet 419. In one embodiment, the magnet 419 is constructed of Neodymium and has a cylindrical shape with a diameter of 6.35 mm and a thickness of 6.35 mm. However, the retaining structure 418 may be structured to retain a magnet of any suitable size and shape. Further, the outer edges of the side frame members 420b each include a plurality of raised teeth 422 positioned in an arc.

Figure 34:
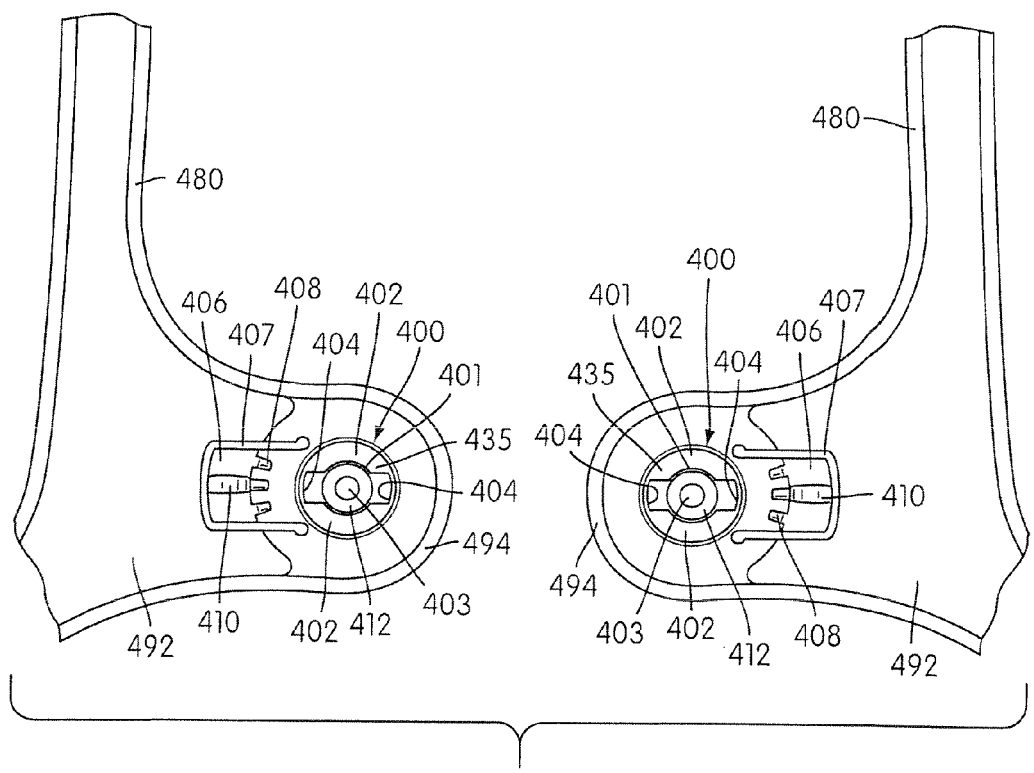
FIG. 34 is a top view of another embodiment of the yokes of the headgear assembly of the nasal mask assembly.
Figure 35:
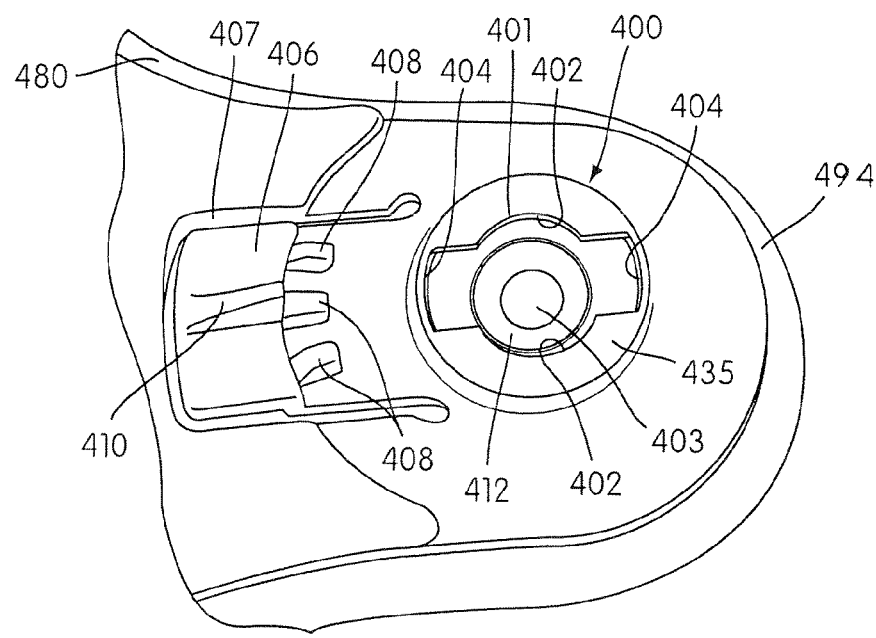
FIG. 35 is an enlarged view of a right side yoke of the headgear assembly shown in FIG. 34.

As shown in FIGS. 34 and 35, the yokes 492 of the headgear assembly 480 each include structure that is similar to the yokes 92 of headgear assembly 80. Specifically, the yokes 492 each include the second connector portion 435 having a mounting flange 400 positioned on the front end 494 thereof. The mounting flange 400 has an aperture or keyhole 401 leading to a bore 403. Two semi-annular flanges 402 are separated from each other by slots 404. A radial inner surface of the semi-annular flanges 402 forms the central bore 403. The yoke 492 also has a spring tab 406 positioned rearward of the mounting flange 400 with a front portion of the spring tab 406 connected to the yoke 492 and a rear portion separated from the yoke 492 by space 407 to be able to flex with respect to the yoke 492 when pressure is applied to the spring tab 406. The spring tab 406 preferably has a plurality of raised teeth 408 positioned in an arc about an axis of the mounting flange 400. The spring tab 406 also has a raised positioning member 410 at its free end to assist the user in locating, engaging and manipulating the spring tab 406.

In contrast to the yoke 92, the yoke 492 includes a ferrous metal disk 412 that is secured within the bore 403. In one embodiment, the metal disk 412 is a steel washer with a diameter of 14 mm and a thickness of 1 mm. However, the metal disk 412 may have any suitable size and shape that can be mounted within the bore 403 of yoke 492. Further, a magnet of suitable size and shape may be used in place of the metal disk 412.

Figure 36:
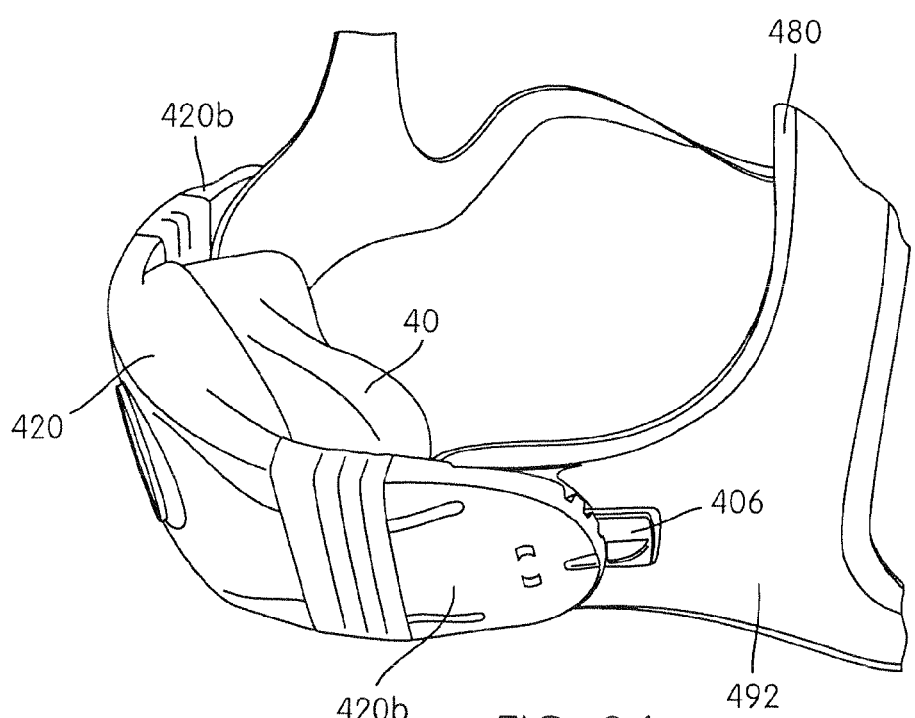
FIG. 36 is a perspective view illustrating the frame of FIG. 33 magnetically coupled to the headgear assembly of FIGS. 34 and 35.
Figure 37:
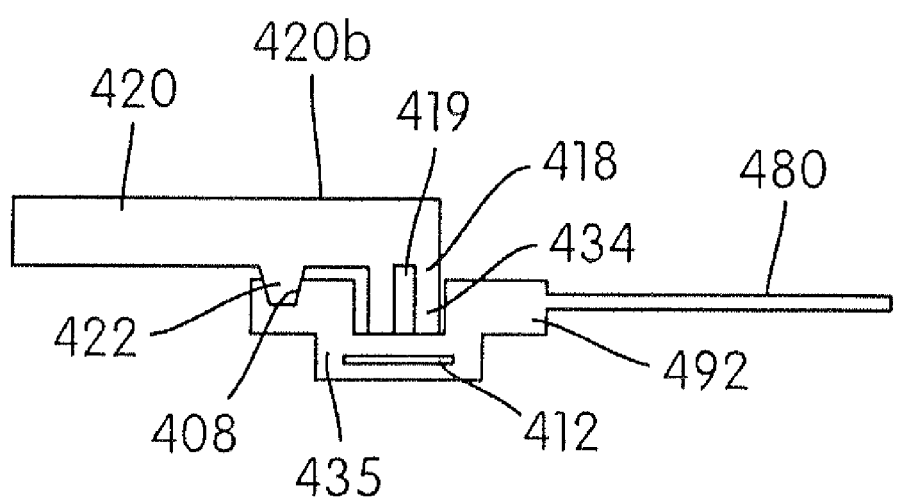
FIG. 37 is a schematic view illustrating the magnetic coupling of the frame of FIG. 33 and the headgear assembly of FIGS. 34 and 35.

As shown in FIGS. 36 and 37, the first connector portion 434 of the frame 420 is engaged with the second connector portion 435 of the yoke 492 such that the magnet 419 is magnetically coupled with the metal disk 412. Specifically, the magnet 419 is axially inserted into the bore 403 so that the magnet 419 is positioned adjacent to or engaged with the metal disk 412 which allows the magnetic attraction between the magnet 419 and the metal disk 412 to axially retain the yoke 492 to the frame 420. The strength of the magnetic attraction between the yokes 492 and the frame 420 may be increased by replacing the metal disk 412 with a magnet, as discussed above. The retaining structure 418 is sized to have a close tolerance with the bore 403 so that the frame 420 and yoke 492 are rotationally supported with one another.

Further, the teeth 422 on the frame 420 are constructed and arranged to engage the teeth 408 on the spring tab 406 when the frame 420 is magnetically coupled with the yoke 492. Once the spring tab 406 has been depressed to lower teeth 408, the yoke 492 can be rotated to a desired position with respect to the frame 420. The spring tab 406 can then be released so that teeth 408 engage teeth 422 in the desired position (within a pitch of the teeth) and rotationally lock the frame 420 with respect to the yoke 492. In accordance with one embodiment, the teeth 408 and 422 can be configured so that when a predetermined torque is applied to the yoke 492, the teeth 422 will automatically force the teeth 408 and spring tab 406 downwardly to allow rotation of the yoke 492 until the torque is removed and the teeth 408 re-engage the teeth 422. The yoke 492 can thus be rotationally adjusted with respect to the frame 420 within an angle of approximately 50-100°, and preferably 75°, depending on the position of engagement between teeth 408 and teeth 422.

The magnet 419 in each side frame member 420b may be oriented such that an incorrect attachment (e.g., left side yoke 492 to right side frame member 420b) is indicated by magnetic repulsion. Specifically, the magnet 419 on one side frame member 420b is oriented so that it will only magnetically couple with one of the yokes 492 and the magnet 419 on the other side frame member 420b is oriented so that it will only magnetically couple with the other of the yokes 492. Thus, sensory indication of correct attachment of the frame 420 to the headgear assembly 480 is achieved by magnetic attraction of correctly paired yokes 492 and side frame members 420b. This construction ensures that the headgear assembly 480 and frame 420 are assembled correctly. Further, this construction enables the frame 420 to be easily coupled with the headgear assembly 480, even in the dark, as the magnet 419 will automatically locate itself in the correct position with respect to the metal disk 412. The headgear assembly 480 may be easily detached from the frame 420 by applying a suitable disengagement force that is greater than the attractive magnetic force between the magnet 419 and the metal disk 412.

Alternatively, the first connector portion 434 on the frame 420 may provide a ferrous metal member and the second connector portion 435 on the yoke 492 may provide a magnet.

Straps

Figure 11:
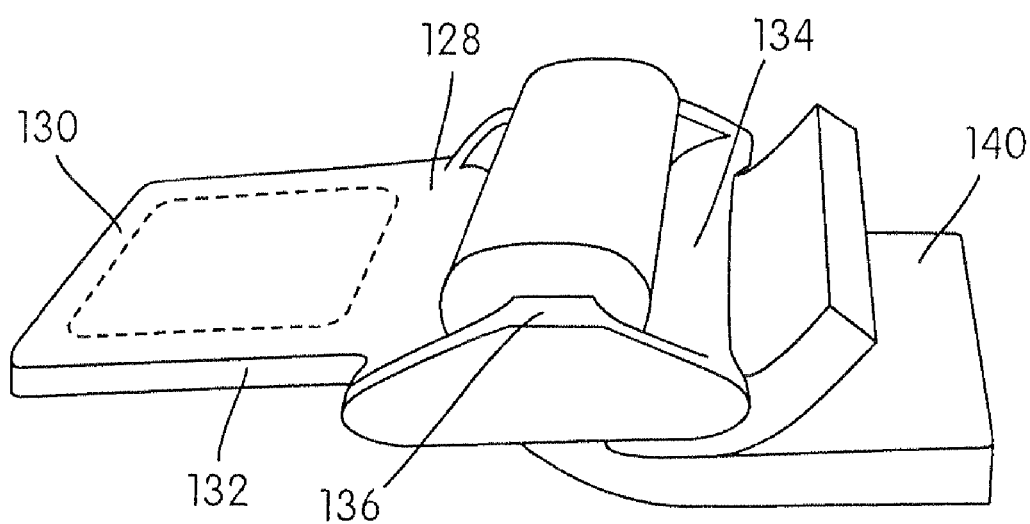
FIG. 11 is a perspective view of a buckle of the nasal mask assembly of FIG. 1.

Each front strap 84 includes a ladder-type buckle 128 attached to the top strap 88 to connect the top strap 88 with a top strap 140 of cross-over strap 138. See FIGS. 1-3 and 11. The buckle 128 can be attached to the top strap 88 with adhesives, stitching and/or other known manners, such as being manufactured integral with the strap. In the embodiment shown in FIG. 11, the buckle 128 includes a plurality of bores 130 evenly spaced around an attachment tab 132 in the form of a square to allow the buckle to be stitched to the top strap 88. The buckle further includes a crossbar 134 and a crossbar 136, around which the top strap 140 can be threaded, in a known manner, so that top strap 140 wraps around crossbar 136 and a free end of top strap 140 is positioned between crossbar 134 and a remainder of top strap 140. Thus, when tension is applied between the buckle 128 and top strap 140, the free end of top strap is frictionally held between crossbar 134 and the remainder of top strap 140 so that the connection between buckle 128 and top strap 140 is self holding under tension. A single cross bar buckle can also be used if used in combination with a strap loop to hold the strap in position. Of course, other connector members can be used instead of the buckle, as is known in the art.

Figure 12:
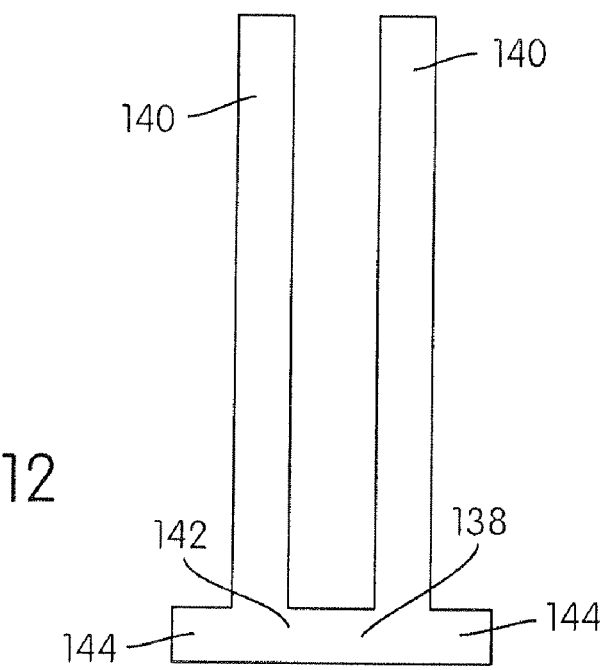
FIG. 12 is a bottom view of a cross-over strap of the nasal mask assembly of FIG. 1 in a relaxed state.
Figure 13:
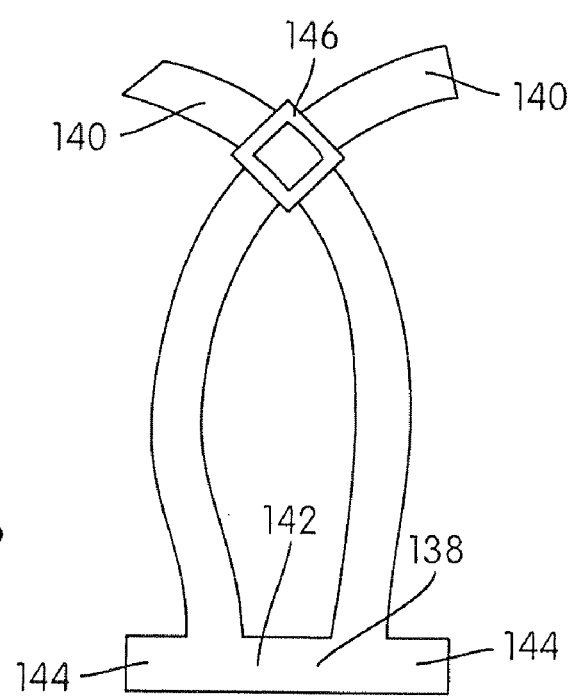
FIG. 13 is a bottom view of the cross-over strap of FIG. 12 in a crossed-over state.
Figure 14:
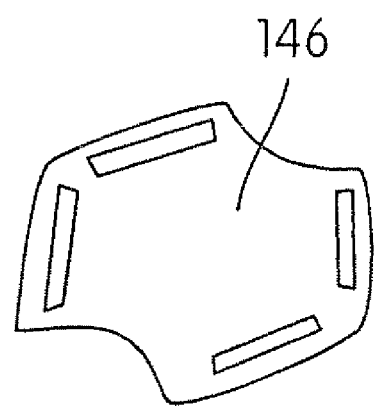
FIG. 14 is a view of a cross-over buckle of the cross-over strap of FIG. 13.
Figure 15:
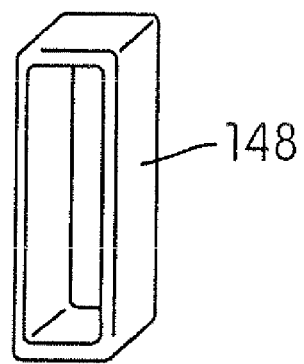
FIG. 15 is a perspective view of a strap loop for use with the nasal mask assembly of FIG. 1.

As shown in FIG. 12, cross-over strap 138 has a generally elongated shape in a relaxed state with two top straps 140 extending upward from a cross-strap 142 having ends 144. To place the cross-over strap 138 in a configuration for wearing, the two top straps 140 are threaded through a cross-over buckle 146, so that they are held in the cross-over position. See FIGS. 13 and 14. In this manner, the left top strap 140 of cross-over strap 138 crosses over to connect with the buckle 128 of right top strap 88 and the right top strap 140 of cross-over strap 138 crosses over to connect with the buckle 128 of left top strap 88. This crossing over of the respective straps helps maintain the headgear assembly 80 and nasal mask assembly 10 in a desired adjusted position on the user. A strap loop 148 can be used to hold down free ends of the respective straps. See FIG. 15. In one form of the invention, the straps are supplied oversized and then cut to length to suit the person.

Similarly to buckles 128 and top straps 88, buckles 150 (FIG. 1) can be attached to cross-strap ends 144 so that the cross-strap ends 144 can be connected to the respective rear strap ends 90 of front straps 84.

Swivel Elbow Assembly

Figure 23:
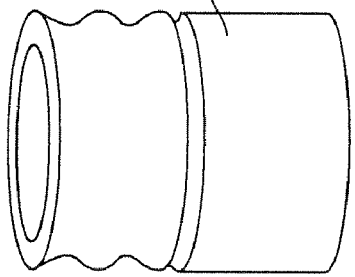
Figure 26:
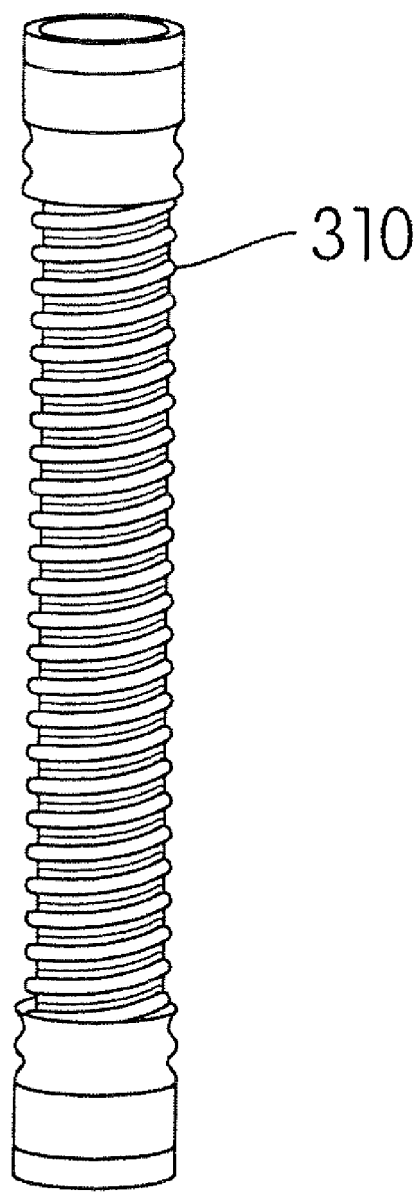
FIG. 26 is a perspective view of an air tube of the nasal mask assembly of FIG. 1.

The swivel elbow assembly 60 of FIG. 6a may be the same as is currently used in ResMed Limited's ULTRA MIRAGE® mask, which employs an internal C-clip member, as described above. The elbow assembly 60 of FIG. 6a is intended to be used with a connector tube 300 (FIG. 23). The connector tube 300 is provided between the elbow assembly 60 and the gas delivery tube 310 (FIG. 26).

Alternatively, the swivel elbow assembly may be constructed in accordance with FIGS. 1-4 and 16-22. Such a swivel elbow assembly 60 may include a swivel elbow 160 and a vent cover 180. Swivel elbow 160 is rotationally connected to frame 20.

In another alternative form of the invention, a further swivel is connected to the end of tube 310, as shown in FIG. 6b.

As shown in FIGS. 16a-19c-2, swivel elbow 160 includes an intake port 162 and an exhaust port 164. The air tube 310 (FIG. 26) is preferably directly connected to a stem 166 of swivel elbow 160 (without connector tube 300) to supply pressurized breathable air or gas from a pressurized supply through air tube 310, intake port 162 and into cushion 40 for breathing by the patient.

The exhaust port 164 is separated from the intake port 162 using, for example, a baffle 161 provided within the interior portion of the elbow 160. See FIGS. 18 and 19a-1. In the illustrated embodiment, the baffle 161 has a generally planar configuration. However, the baffle 161 may have a curved configuration or any other suitable configuration for separating the exhaust port 164 from the intake port 162. The orientation of the intake and exhaust ports 162, 164 was selected such that the incoming gas, indicated by the directional arrow in the intake port 162, less directly impacts the flow of gas washout along the exhaust port 164. Further, the gas entering the elbow 160 is less likely to flow directly into the exhaust port 164 since the baffle 161 forces the incoming air to take a tortuous path, e.g., turn around about 180 degrees, before being able to exit through the exhaust port 164.

Figure 16B:
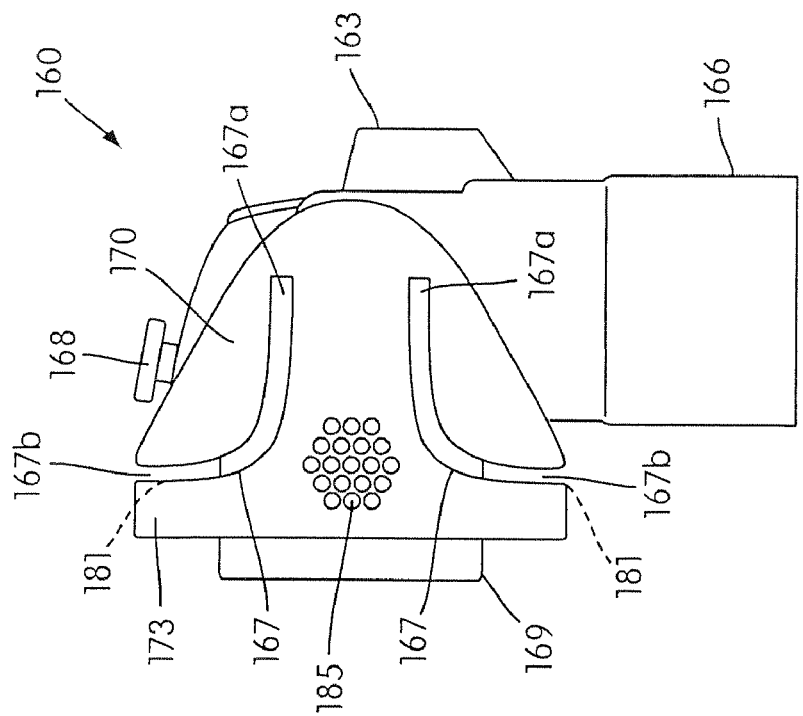
FIG. 16b is a side view of a swivel elbow of the nasal mask assembly of FIG. 1.
Figure 16A:
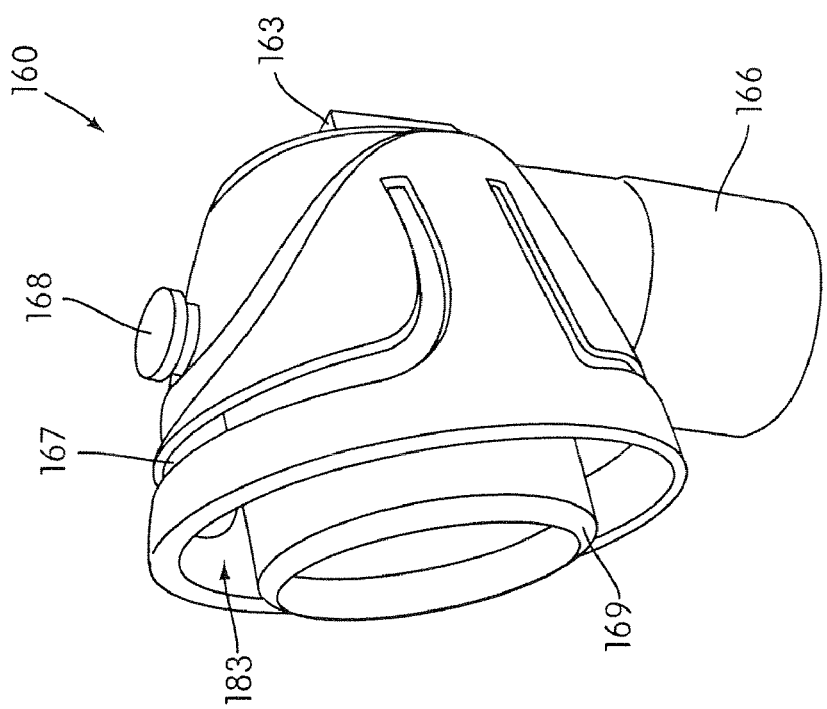
FIG. 16a is a perspective view of the swivel elbow shown in FIG. 1.
Figure 18:
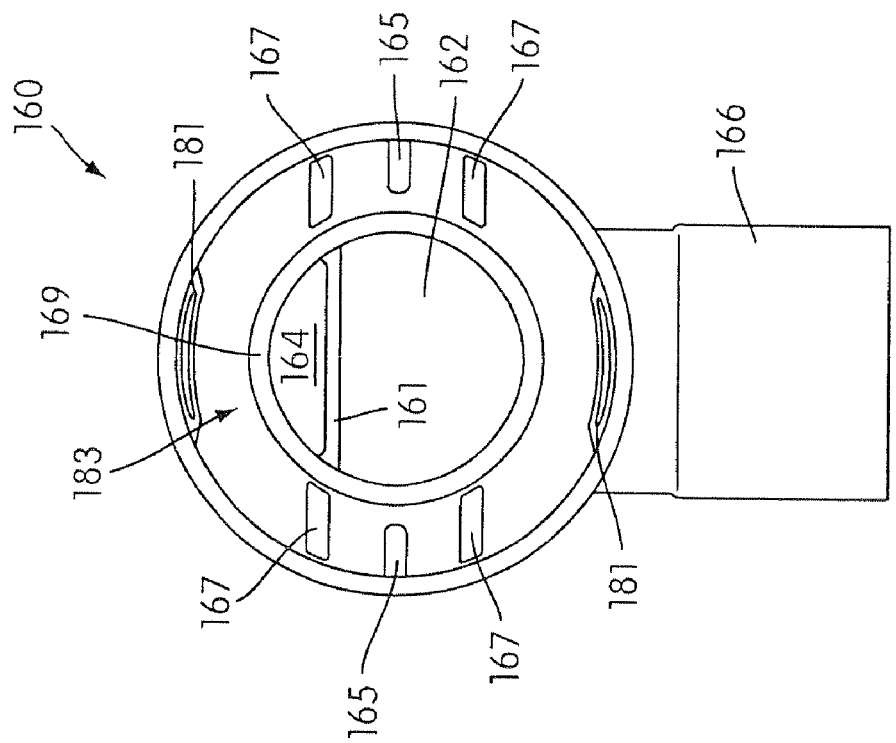
FIG. 18 is a rear view of the swivel elbow of FIGS. 16a and 16b.
Figure 17:
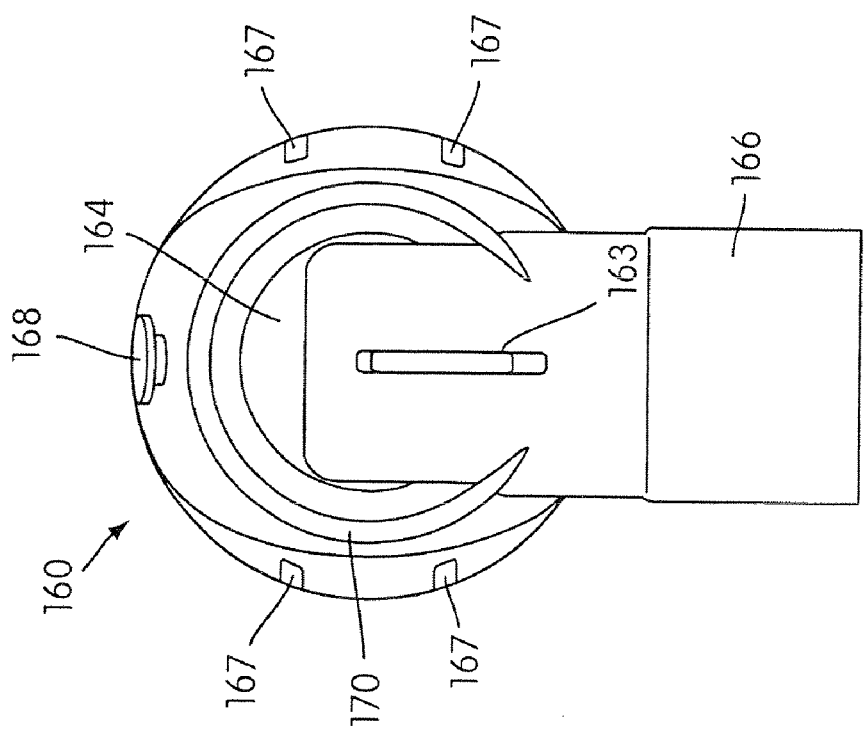
FIG. 17 is a front view of the swivel elbow of FIGS. 16a and 16b.

The elbow 160 includes an end portion 169 that is adapted to engage the aperture 24 provided in the frame 20, to provide gas into the nasal cavity formed by the frame 20 and the cushion 40. The baffle 161 terminates just inside the end portion 169 of the elbow. A flexible quick release mechanism includes a collar 173 and an apron 170. The collar 173 includes a generally T-shaped member, as seen in FIG. 16b, that surrounds the end portion 169 of the elbow 160. Preferably, the end portion 169 of the elbow 160 extends beyond the collar 173 to improve alignment when assembling into frame 20. The collar 173 is spaced away from the end portion 169 in concentric relation so as to form a receiving space 183 between the collar 173 and the end portion 169, as shown in FIG. 18. The apron 170 is preferably formed as an integral part of the elbow 160, and is connected to the lower leg of the T-shaped collar 173. Two grooves 167 are provided between the collar 173 and the apron 170. A portion 167a of the groove 167 allows the lower leg of the T-shaped collar 173 to flex with respect to the apron 170. A portion 167b of the groove allows the cross portion of the T-shaped collar 173 to flex outwardly and inwardly with respect to the end portion 169 of the elbow 160.

Figures 2, 19A:
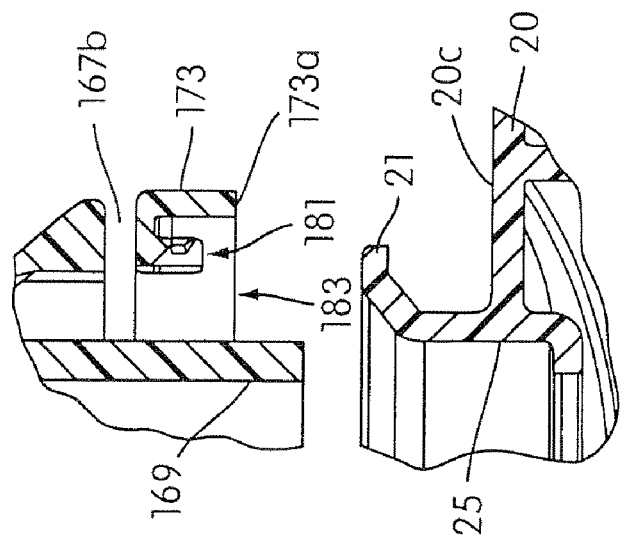
Figures 1, 19A:
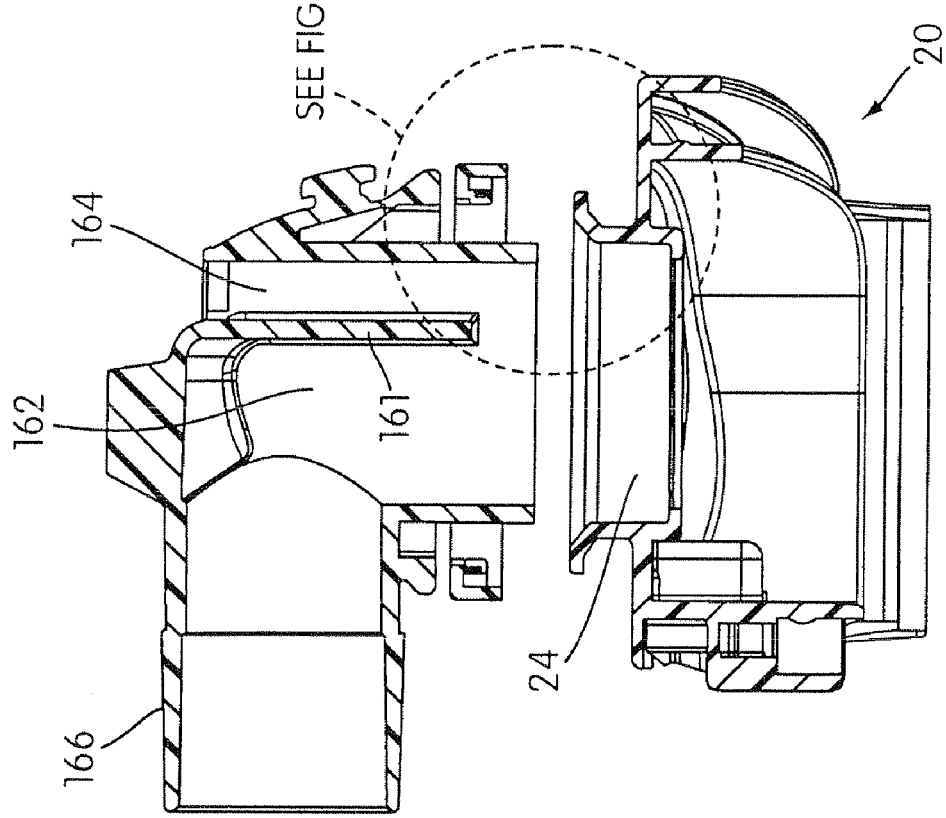
Figures 2, 19B:
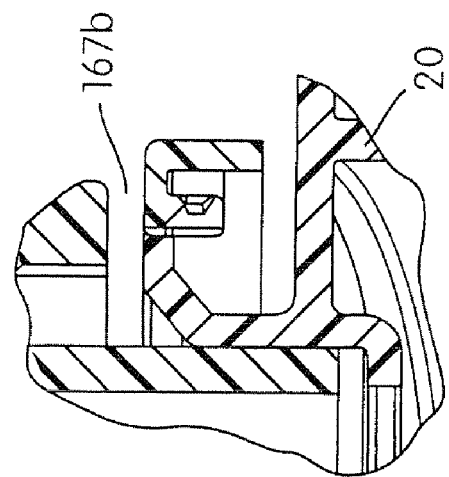
Figures 1, 19B:
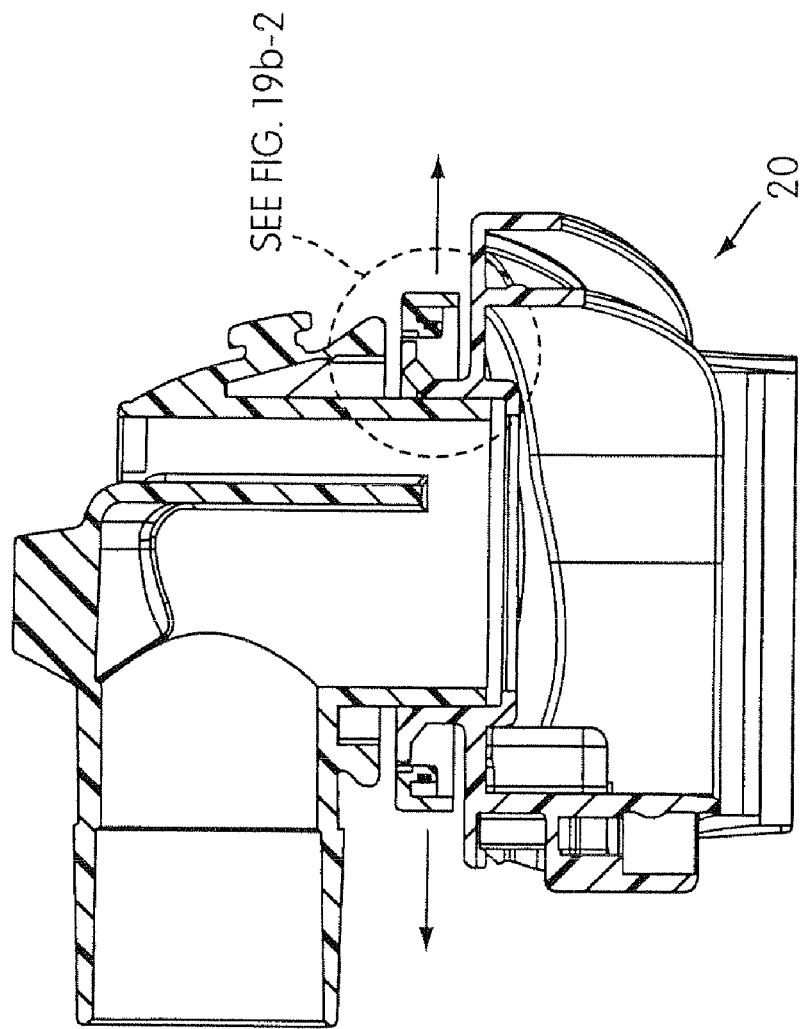
Figure 22:
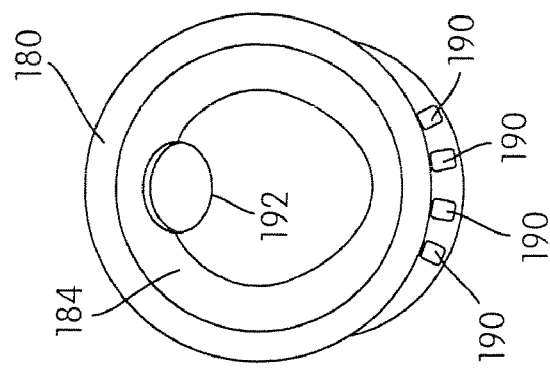
FIG. 22 is a bottom view of the vent cover of FIG. 20.
Figure 21:
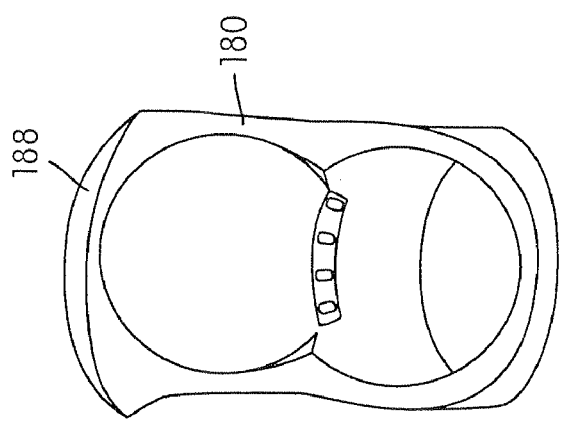
FIG. 21 is a rear view of the vent cover of FIG. 20.
Figure 20:
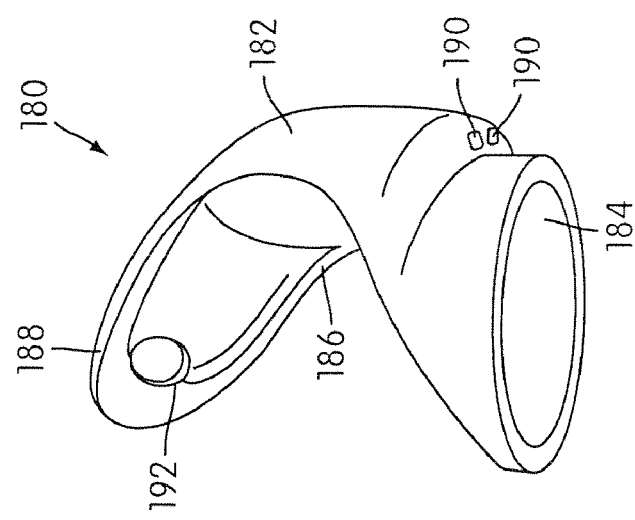
FIG. 20 is a perspective view of a vent cover of the nasal mask assembly of FIG. 1.
Figure 22D:
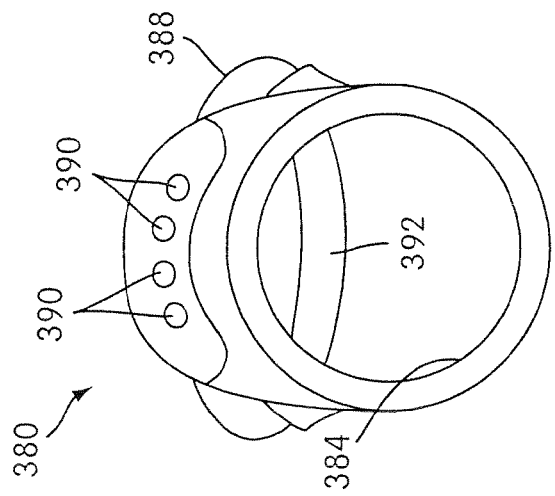
FIG. 22d is a bottom view of the vent cover of FIG. 22b.
Figure 22C:
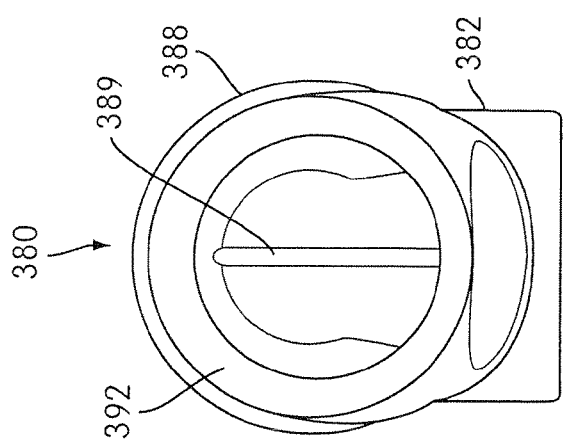
FIG. 22c is a rear view of the vent cover of FIG. 22b.
Figure 22B:
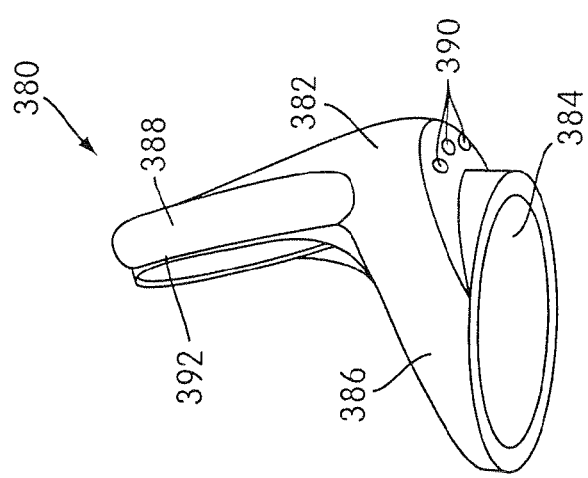
FIG. 22b is a perspective view of another embodiment of a vent cover for connection with the swivel elbow of FIG. 18b.

FIGS. 19a-1-19c-2 show sequential views illustrating connection between the elbow 160 and the frame 20. FIGS. 19a-1-19a-2 show a cross section of the elbow 160 just before connection with the mask frame 20. FIGS. 19b-1-19b-2 show the elbow 160 and frame 20 in the nearly connected condition, and FIGS. 19c-1-19c-2 show the elbow and frame in the fully connected condition.

The frame 20 includes a flange 21 provided at a distal end of a wall 25 defining the aperture 24. FIGS. 5 and 5a show the flange 21, while the embodiment of FIG. 6a does not show or include such a flange since a different elbow assembly 160 is employed. As the flange 21 is inserted within the space 183, it engages protrusions 181 formed in the inside surface of the collar 173. In this embodiment, only two protrusions 181 are provided. The protrusions 181 are ramped or inclined such that engagement with the flange 21 causes outward flexure (FIG. 19b-1-19b-2) of each end of the cross portion of the T-shaped collar 173, until the flange 21 aligns with and is received within the groove portion 167b (FIG. 19c-1-19c-2). In this state, with the elbow 160 secured to the frame 20, the collar 173 returns to its unflexed state. Portions of the flange 21 rest against lugs 165 provided within the space 183.

The engagement between the collar 173 and the flange 21 during the snap-action connection of the elbow 160 and the frame 20 results in an audible click or sound indication. This sound indication is advantageous to signal the user that the elbow 160 is securely attached to the frame 20.

To release the elbow 160 from the frame 20, portions 185 on each side of the collar 173 are flexed towards one another in order to raise the protrusions 181 radially outwardly to allow passage of the flange 21. In this manner, the elbow 160 can be quickly and easily removed from the frame 20 without accessing the interior portion of the nasal cavity, as would be the case with an elbow connected using a C-clip (FIG. 6b). As shown in FIG. 16b, a preferred form of the elbow 160 includes textured protrusions 185 to assist users to locate the release points. The distance between the opposed textured portions 185, i.e., the diameter of the collar 173, is approximately 35-45 mm, and preferably 40 mm.

The elbow 160 also is adapted to connect directly to the gas delivery tube 310 (FIG. 26) without the connector 300 shown in FIG. 23. (See FIG. 1). FIG. 6b shows the connector 300 between the elbow and the gas delivery tube 310. Removal of the connector 300 is advantageous because the length of the effective lever arm of the combined elbow and connector 300 (FIG. 6b) may increase the possibility that unwanted levels of torque are applied to the frame 20 or mask assembly 10 relative to the patient's head/face. By eliminating the need to use the connector 300, the effective length of the level arm can be reduced, which results in less torque being applied to the mask assembly which results in increased stability. With increased stability, patient comfort is increased and compliance is increased.

In the connected state, the inside surface of the wall 25 of the frame 20 sealingly engages the outside surface of the end portion 169 of the elbow as shown in FIG. 19a-1-19c-2. These surfaces engage one another for a distance of approximately 1-10 mm, preferably 6 mm, which helps to seal as well as to provide stability to the connection between the elbow 160 and the frame 20. As seen in FIGS. 19c-1-19c-2, a portion of the wall 25 extends inside the mask to further increase the area of contact between the elbow 160 and the frame 20. In the connected state, an end portion 173a of the collar 173 is flush with the outside surface 20c of the frame 20, as shown in FIGS. 19c-1-19c-2. The wall 25 includes a flange 25a (FIG. 19c-2) to form a stop for the insertion of the end portions 169, and to permit a controlled leak between the elbow 160 and frame 20. In one embodiment, the leak between the elbow 160 and frame 20 is minimal. In another embodiment, a seal is provided between the elbow 160 and frame 20 to prevent a leak.

This system allows for the rapid and precise connection between the elbow 160 and the frame 20. It also allows for simple disassembly. Moreover, the elbow 160 is configured to allow the patient to attach and detach the elbow 160 from the frame 20 with one hand. This is advantageous when cleaning the mask or if the patient should choose to interrupt treatment during a session, while intending to resume treatment a short time later. The elbow assembly 60 and frame 20 connection allows the patient to rapidly disconnect the elbow 160 from the blower's gas delivery tube while keeping the mask frame, cushion and headgear in place on the patient's head during a momentary treatment interruption. The aperture 24 is large enough to lower impedance, to thereby enable the patient to breathe comfortably since a sufficient amount of gas can be accommodated by the aperture 24. Specifically, the aperture 24 has an area of at least 180 mm². In one embodiment, the aperture 24 has a diameter in the range of 20-30 mm, preferably 27 mm, and an area in the range of 200-600 mm², preferably in the range of 500-600 mm². As illustrated, the aperture has a generally circular shape. However, the aperture may have a non-circular shape. Further, the frame may have a plurality of apertures therethrough with the elbow coupled to the frame such that it surrounds the plurality of apertures. In this respect, a mask in accordance with an embodiment of the invention differs from prior art mask arrangements which included quick release mechanisms with narrower apertures. Such narrower apertured quick release mechanisms could lead to patient discomfort, for example anxiety or claustrophobia. Discomfort is exacerbated by increased $CO_2$ re-breathing or increased flow impedance.

Vent Cover

Vent cover 180 includes a main body 182 having a lower bore 184, curved portion 186 and top portion 188. See FIGS. 20-22. The main body 182 also includes at least one vent 190, and in a preferred embodiment, a plurality of vents 190 extending from an interior of the vent cover to an exterior of the vent cover. Top portion 188 of vent cover 180 includes flange or aperture 192 for engaging latch 168 of swivel joint 160. In the illustrated embodiment, the vent cover 180 includes an aperture 192. The vent cover 180 is connected to the swivel joint 160 by placing the stem 166 of the swivel joint 160 through lower bore 184 of the vent cover 180. The vent cover 180 is then moved toward the swivel joint 160 until the latch 168 extends through the aperture 192, as shown in FIG. 1. This configuration allows for the vent cover 180 to remain in the vicinity of the elbow assembly 160 and/or mask assembly 10, as it is captured by the elbow 160 or the gas delivery conduit. This is convenient in that should the vent cover 180 become dislodged during cleaning or by inadvertence, it will not drop and become lost, as it is retained by the mask assembly.

The curved portion 186 of the vent cover fits adjacent apron 170 of the swivel joint 160 to provide a generally air-tight seal between an interior of the vent cover 180 and the swivel joint 160. In this manner, exhalation gases from an interior of the mask can flow through exhaust port 164 of swivel joint 160, through the interior of the vent cover 180 and to the atmosphere through vents 190. FIG. 19c-1 includes an arrow B that approximates the path exhaust gas follows when the vent cover is in position. This arrangement has an additional advantage in that the vent direction reduces or prevents irritation of a bed partner of the patient by gas flow from the mask. FIGS. 1-4 show the elbow 160 and vent cover 180 in the connected position. A spacer 163 is provided to ensure that the vent cover 180 is spaced sufficiently away from the exterior surface of the elbow 160, which especially helps prevent the air gap from collapsing since the vent cover is preferably made of a resilient flexible material. Of course, the vent cover could be made of a plastic member somewhat like the cover used in the Ultra Mirage™, if desired. In addition, this vent arrangement can be replaced or supplemented using ResMed's vent assembly disclosed, for example, in U.S. patent application Ser. No. 09/021,541, incorporated herein by reference in its entirety.

Figure 18C:
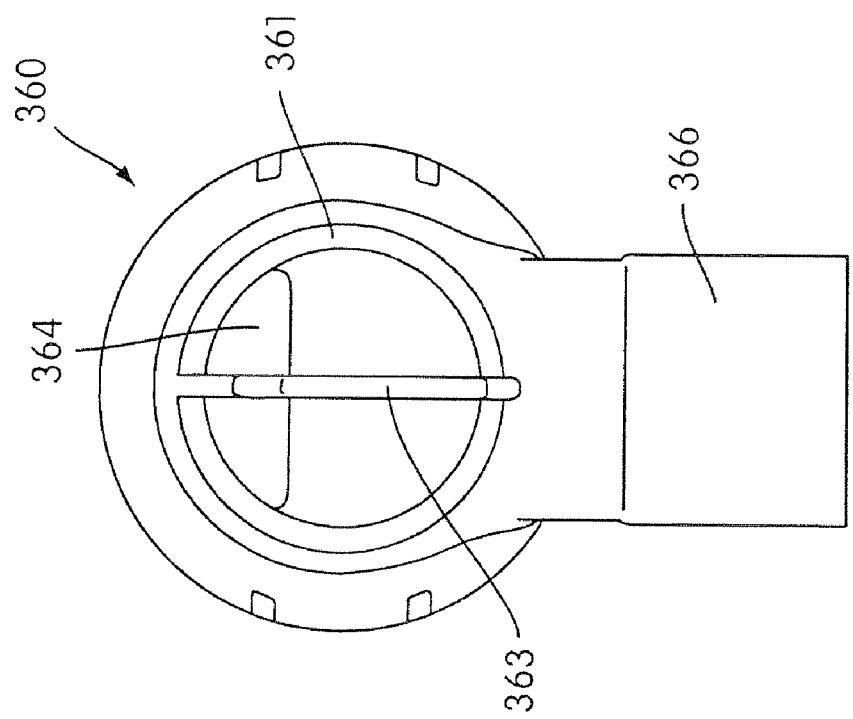
FIG. 18c is a front view of the swivel elbow of FIG. 18b.
Figure 18B:
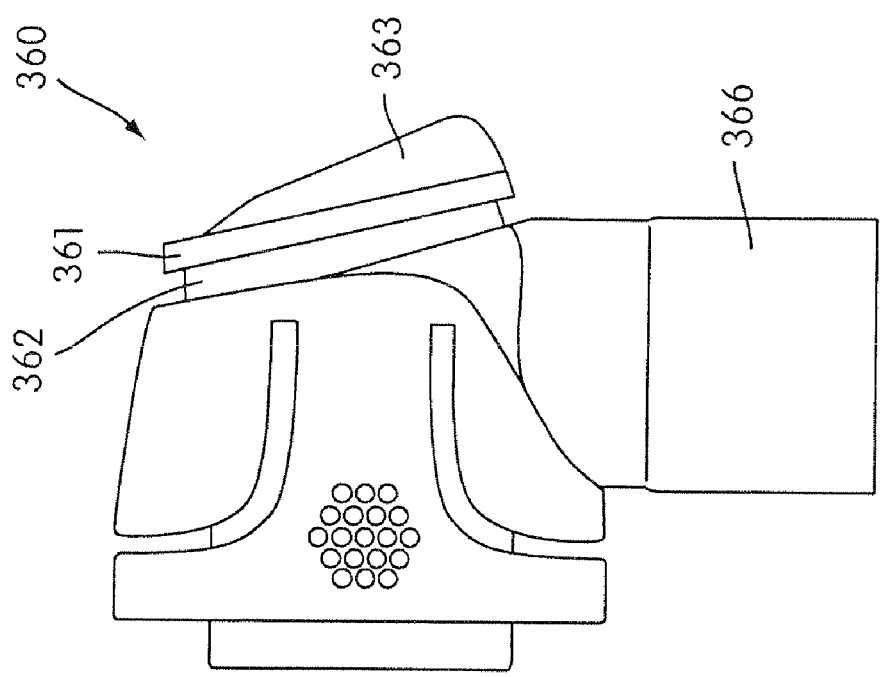
FIG. 18b is a side view of another embodiment of a swivel elbow.
Figure 18D:
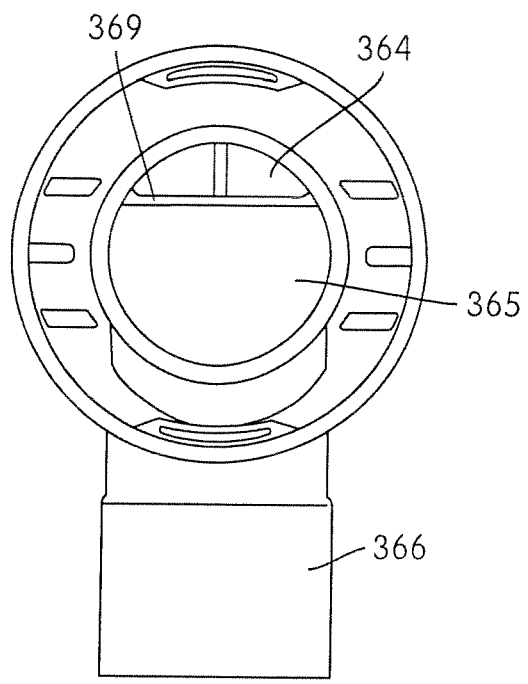
FIG. 18d is a rear view of the swivel elbow of FIG. 18b.
Figure 18E:
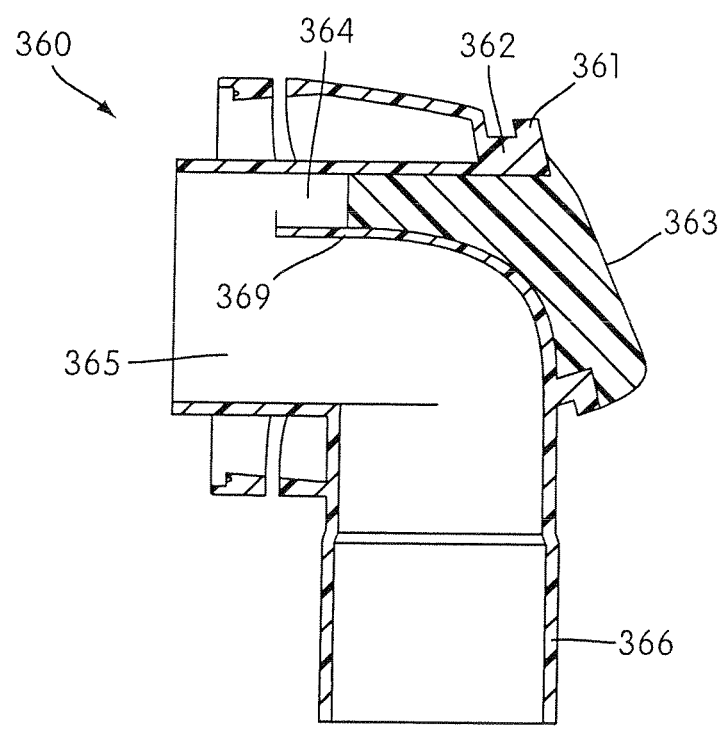
FIG. 18e is a cross-sectional view of the swivel elbow of FIG. 18b.

FIGS. 18b-18e illustrate another embodiment of the swivel elbow, indicated as 360, that is adapted to be connected to the vent cover 380 illustrated in FIGS. 22b-22e. As shown in FIGS. 18b, 18c, and 18e, the swivel elbow 360 includes a flange 361 provided at a distal end of a wall 362 surrounding the outlet of the exhaust port 364. FIGS. 18d and 18e show the intake port 365, the exhaust port 364, and a baffle 369 that separates the intake and outlet ports 365, 364. As illustrated in FIG. 18e, the baffle 369 has a curved configuration. Specifically, the baffle 369 curves generally downwardly as it extends from the inlet of the exhaust port 364 to the outlet of the exhaust port 369. However, the baffle 369 may have a generally planar configuration similar to baffle 161 shown in FIG. 19a-1. Alternatively, the baffle may have any other suitable configuration to separate the intake and outlet ports 365, 364. As shown in FIGS. 22b-22e, the vent cover 380 includes a main body 382 having a lower bore 384, an intermediate portion 386 and top portion 388. The main body 382 also includes a plurality of vent holes 390 extending from an interior of the vent cover to an exterior of the vent cover. The top portion 388 of the vent cover 380 includes a collar 392 for engaging the flange 361 of swivel elbow 360. The vent cover 380 is connected to the swivel elbow 360 by placing the stem 366 of the swivel elbow 360 through lower bore 384 of the vent cover 380. The vent cover 380 is then moved toward the swivel elbow 360 until the collar 392 latches onto the flange 361 of the swivel elbow 360. The collar 392 is stretched to overcome the flange 361, and firmly grips the flange 361 due to its resiliency and elasticity. In the illustrated embodiment, the collar 392 has a generally circular shape so that stress ("hoop stress") applied to the flange 361 and wall 362 is evenly distributed. Similar to the embodiment of vent cover 180, this configuration allows for the vent cover 380 to remain connected on in the vicinity of the swivel elbow 360 and/or mask assembly, as it is captured by the elbow 360 or the gas delivery conduit. The vent cover can be considered "self-holding" in that it can be held in place on the elbow to cover the exhaust passage without an additional securing mechanism. In addition, the vent cover is held onto the elbow via the ring-shaped lower bore 184 as the patient stretches the collar 392 over the flange 361, which minimizes the chances for losing the vent cover if the first assembly attempt is not successful.

Figure 22F:
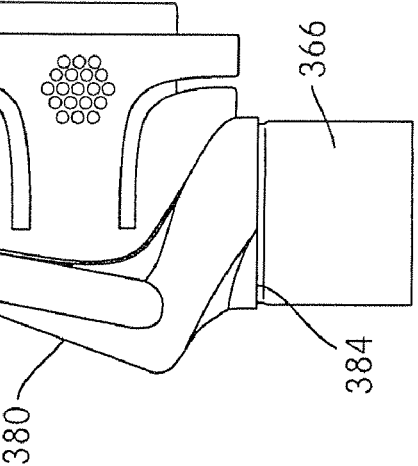
FIG. 22f is a side view of illustrating the vent cover of FIG. 22b connected to the swivel elbow of FIG. 18b.
Figure 22E:
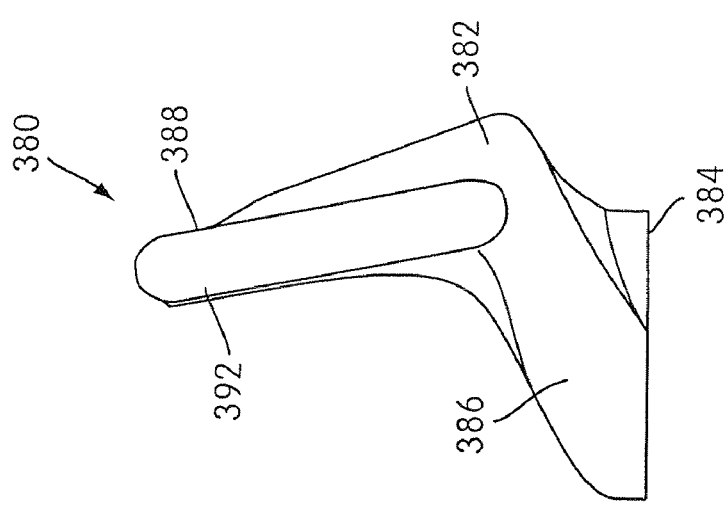
FIG. 22e is a side view of the vent cover of FIG. 22b.

FIG. 22f shows the swivel elbow 360 and vent cover 380 in the connected position. As shown in FIGS. 18c and 18e, the swivel elbow 360 includes a wall 363 that ensures that the vent cover 380 is spaced sufficiently away from the exterior surface of the swivel elbow 360, which especially helps prevent the air gap from collapsing since the vent cover 380 is preferably made of a resilient flexible material. The vent cover 380 includes a recess 389 (FIG. 22c) on an inner surface of the top portion 388 that engages the wall 363.

Mask Cushion

The cushion is designed to rest on the face and apply pressure around its perimeter while minimizing and/or avoiding contact with pressure sensitive regions on the face. Some parts of the face require special attention to achieve a balance of pressure and seal. It is also desirable to provide a low profile mask to improve patient comfort level by improving stability, and to reduce the forces which may tend to pivot the mask relative to the patient's face. Properties are listed below with the measures taken to create a successful design.

Figure 24A:
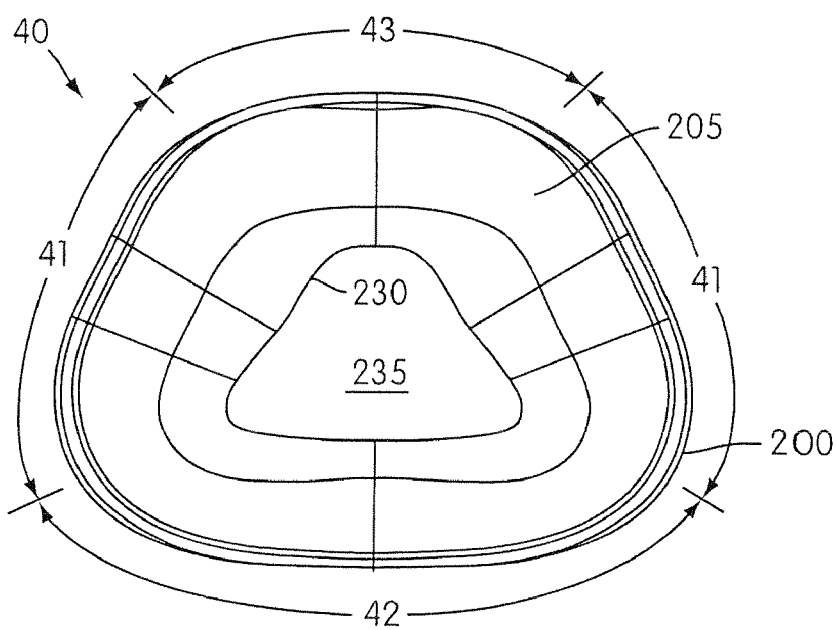
FIG. 24a is a face side view of a cushion of the nasal mask assembly of FIG. 1 showing Computer Aided Design (CAD) construction lines.
Figure 24B:
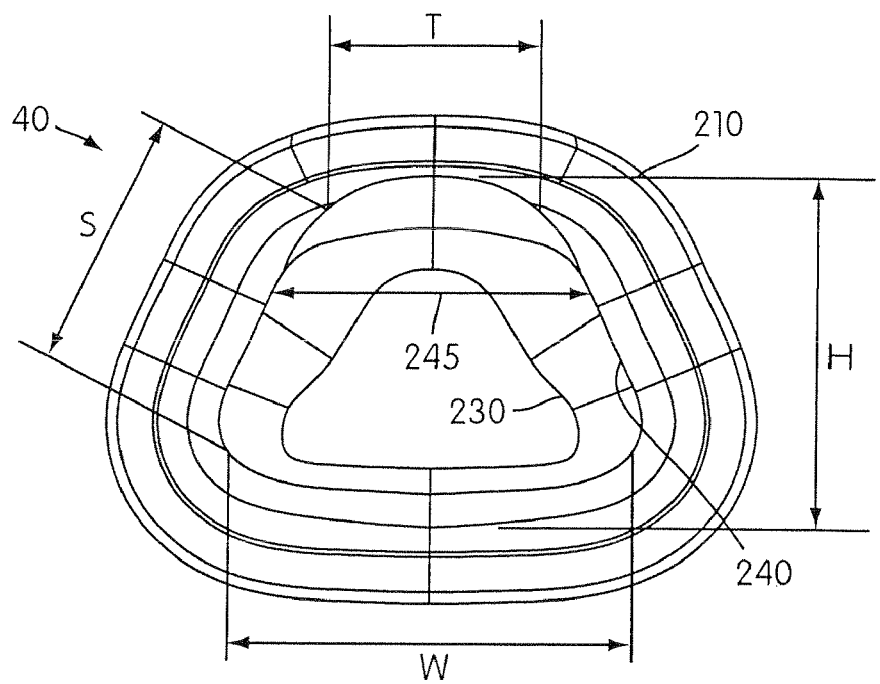
FIG. 24b is a frame side view of the cushion of FIG. 24a showing CAD construction lines.
Figure 24C:
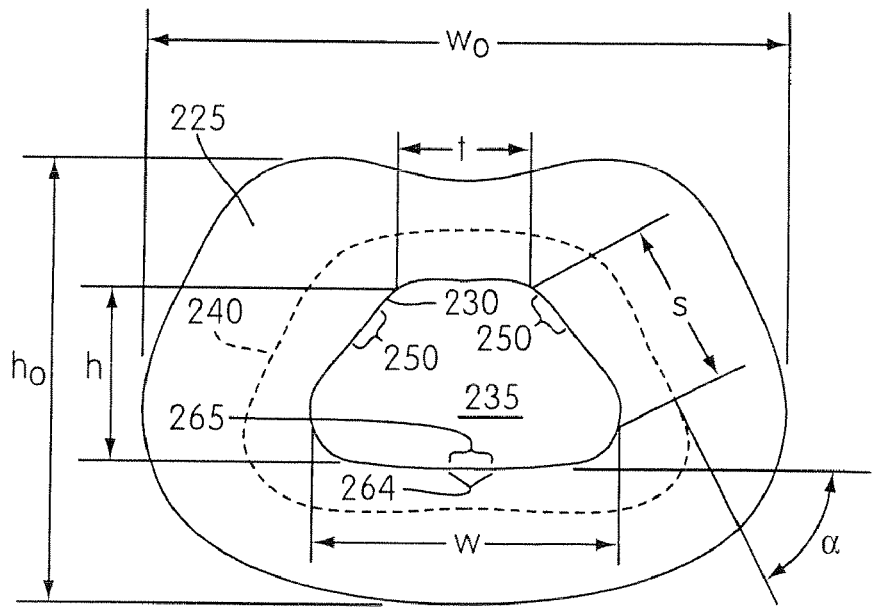

The cushion has a face-contacting side and a non face-contacting side with a wall therebetween. The non-face contacting side of the cushion engages with the mask frame. In one form of the invention, the shape of the cushion on its face-contacting side, as per the view shown in FIG. 24c, is generally trapezoidal. In this aspect, the shape of the cushion on the face contrasts with prior art cushions having a generally triangular shape. An advantage of this trapezoidal shape is that it assists sealing at a point lower down the nose without impeding flow through the patient's or user's nasal vents (that is, in the region of the lateral nasal cartilage and just below the nasal bone on either side of the nose). Thus, the cushion is positioned on a lower portion of the nasal bridge region of the patient. Moreover, the cushion is configured and positioned such that contact pressure of the cushion on the nasal vents is minimized or eliminated. The shape of the cushion may be altered, e.g., a triangular or other non-trapezoidal shape could be used, keeping in mind that localized pressure points on the lower nasal bridge region and occlusion of the nasal vents should be avoided. Some prior art mask cushions push on the nasal vents which can increase the impedance of the nasal vents to airflow. In a preferred form of the cushion, both the face-contacting and non face-contacting sides of the cushion have the same general trapezoidal shape.

In one form of the invention, a combination of support structure and sealing structure is provided in the region of the face contacting side of the cushion. The support and sealing structures may be provided as part of the cushion, or alternatively using separate components. Where the support and sealing structures are provided as part of the cushion, the cushion may have a single-walled, double-walled or triple- or more walled construction. In a preferred form of cushion, the sealing structure is provided by a thin membrane, whereas the support structure is provided by a thicker frame.

The center and sides of the nasal bridge are particularly sensitive to contact pressure. Thus, it is important that the cushion seals as lightly as possible in this area. Instability of the cushion may cause an increased pressure in the nasal bridge region and thus presents an extra challenge in this area. The supporting element (e.g., frame 200 shown in FIG. 24a) can be designed to totally avoid contact with the adjacent portion of the overlying face-contracting element (e.g., membrane 205 shown in FIG. 24a), thereby allowing the membrane 205 alone to seal. While localized points of contact pressure should be avoided in the nasal bridge region, especially at the sensitive apex thereof that contacts the lower nasal bridge region, the seal must be maintained. The lower nasal bridge region is positioned generally where the bony region of the nasal bridge transitions to a portion of the nose containing more cartilage. In addition, the forces that are applied to the face should be substantially evenly distributed around the entire perimeter of the cushion 40. An aspect of the invention is that the facial contact pressure is controllably distributed around the face. Of course, the forces applied to the lower nasal bridge region can be spread out along a relatively wider section of the membrane 205, to avoid the localized forces, while the forces in the lip and cheek regions can be slightly more localized, e.g., spread out over less distance in the width direction, since forces can be more comfortably accommodated in the lip and, particularly, in the cheek regions. Moreover, the contact area or width between the membrane and the face in the lower nasal bridge region may be greater than the contact area or width between the membrane and the lip and cheek regions, while maintaining a relatively constant overall force distribution around the face of the patient, which improves comfort. Using this arrangement, the patient perceives that the pressure is evenly distributed over the contact region, even though the actual force over the contact region may not be evenly distributed.

Another advantage is that the angle of the cushion with respect to the patient can change without adversely affecting sealing efficiency. For example, the cushion may contact different patients at different angles based on the shape of the patient's face, and the angle of the cushion can move with respect to the face during movement when the patient is asleep.

The sealing element (e.g., membrane 205) incorporates a large effective rolled over section (large radius) to allow some degree of movement or rotation of the mask relative to the patient's face and prevents the membrane distal edge from irritating the patient's face and/or nose. The sealing element (e.g., membrane) snugly seals against the nose by conforming around a lower portion of the nasal bridge at sides of the nose. A compromise must be reached between a secure seal and membrane tightness/stretching across the nose. The membrane cutout can be notched to enable maximum stretch distance without edge tightness. Stretch can also be achieved by materials, for example softer material and or thinner materials, for example, elastomer, silicone, polyurethane, thermoplastic elastomers, foamed elastomers and/or composites.

The sealing element (e.g., membrane) is preferably elastomeric having a thickness in the range of 0.1 and 2.0 mm, preferably 0.35 mm, to allow the membrane to stretch readily over the lower portion of the nasal bridge. The stretch of the membrane may be varied in different regions by varying its thickness, adding stiffening structure such as ribs, or using composites.

Facial wrinkling is most pronounced at the facial or nasal crease between the sides of the nose (also known as the naso labial sulcus) and the cheek and presents a challenge in effective sealing. The underlying cushion (e.g., frame 200 shown in FIG. 24a) sits as close to the sides of the nose as possible. In this way it seals in the flattest area possible. The curved area designed to sit in the facial crease should have as small a radius as is practical. The membrane 205 extends inwardly and/or downwardly further than the edge of the cushion (e.g. rim 225) to allow rolling around the outer edge at the sides of the nose. This lessens the likelihood of irritation arising from rough edges and prevents the inner cushion rim 225 from being a source of irritation against the patient's face and/or nose.

Excess pressure across the top lip can be caused by both cushion design and by the vertical rotation of the mask under its own weight, or by undesirable force applied to the mask, for example, due to tubing drag or the weight of components attached to the mask. The design of the headgear, as described above, can help reduce the possibility of adding unwanted pressure to the lip region due to vertical rotation of the mask under its own weight. The lip region 42 may include a notch to accommodate the bottom of the septum of the patient, to enhance sealing and comfort, as shown in FIG. 24g. The septum notch 264 would be provided in region 265, as shown in FIG. 24c. FIGS. 24a and 24b show front and rear views of the cushion 40. In an alternative embodiment, a septum notch may also be provided on the underlying frame.

The cushion 40 preferably has a generally trapezoidal shape in this embodiment. However, the cushion 40 may have a non-trapezoidal shape such as a triangular shape. The cushion 40 includes a pair of cheek regions 41 to provide a seal in the crease between the cheeks and the sides of the nose, a lip region 42 provided to provide a seal below the nose and above the upper lip of the patient, and a nasal bridge region 43. The nasal bridge region 43 spans across the lower portion of the bridge and sloping sides of the bridge that intersect with the nasal crease formed between the cheeks and the sides of the nose. The transition between the lip region 42 and each cheek region 41 is where the cushion 40 begins to turn around the bottom of the nose towards the side of the nose. The transition between the nasal bridge region 43 and each cheek region 41 is where each cheek region 41 diverges upwardly towards the bridge of the nose. In other words, the nasal bridge region 43 starts where the cheek region begins to angle upwardly. See FIG. 24d.

The nasal bridge region 43 is designed to contact the patient's nose, for example, as shown in FIG. 1, where it can be seen that the lower portion of the bridge is selected for contact. Note that FIG. 1 shows the cushion 40 spaced away from the frame. However, pictures in Appendix C of incorporated U.S. Provisional Application of Moore et al., Ser. No. 60/402,509, show the nasal mask assembly attached to two model noses (A & B), described further below. More specifically, the nose includes relatively bony sections at the upper portion of the bridge, and flexible cartilage at the tip of the nose. Reference may be had to Gray's Anatomy, Thirty-Eighth Edition (1995), Figures 6.133A, B, 6.135A and 11.3A, B, incorporated herein by reference for drawings showing these regions. It is desirable to avoid localized pressure points along the bony region of the nose, to increase comfort to the patient. Conversely, it is desirable to avoid mask contact with only the cartilage portion of the nose, because its flexibility may allow too much unwanted movement of the cushion in use, may occlude the nasal passages of the patient, and may not provide a stable fit. In addition, positioning on the tip of the nose may increase the distance between the center of gravity of the mask assembly of the face of the patient—an undesirable consequence.

Accordingly, the optimal region of sealing engagement between the cushion and the bridge is somewhere between the uppermost bony region and the lower cartilage region of the nose. Optimally, the region of contact is just above the cartilage on the bone. Generally, the cushion can sit on the bone along the center of the nose, but it needs to avoid areas of cartilage on the sides of the nose. The nasal length and other appropriate dimensions can be measured from the base of the nose and the transition, or it can be obtained from statistical information on human anatomy. Samples of typical dimensions which are considered include one or more of those found in FIGS. 30 and 31. However, the cushion may not contact the patient in the lower nasal bridge region (positioned generally where the bony region of the nasal bridge transitions to a portion of the nose containing more cartilage) in all cases due to differences in the facial contour for each individual patient.

The cushion 40 is designed to accommodate most of the patient population (e.g., 80% of the patient population) in one or more sizes, preferably one to three sizes. The distance between the base of the nose and the top of the bridge is longer than the distance between the base of the nose and the transition between bone and cartilage. The cushion 40 can be made compact and/or lightweight since it need not accommodate the entire length of the nose. This frees designers to optimize or improve other areas of the cushion 40 and increases the patient's field of view while wearing the mask. Certain facial dimensions have been identified for optimal mask design to maximize the portion of the population that can be accommodated. In one embodiment, a series of color coded cushions is used. The cushion may be color coded for type or size, for example.

Figure 24D:
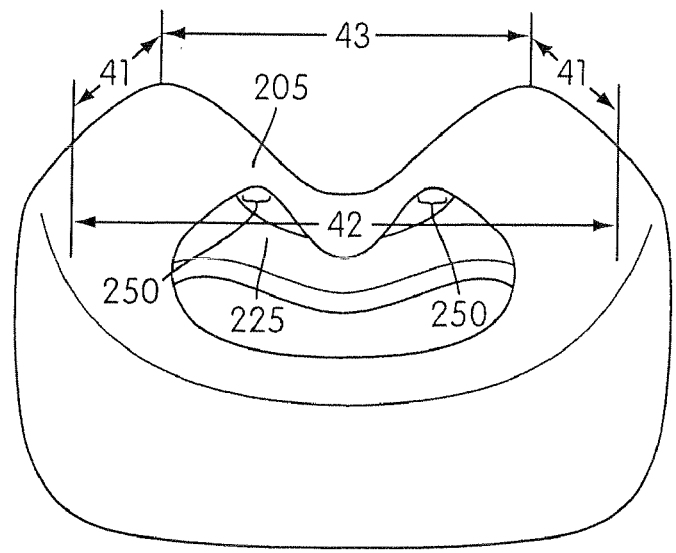
Figure 24E:
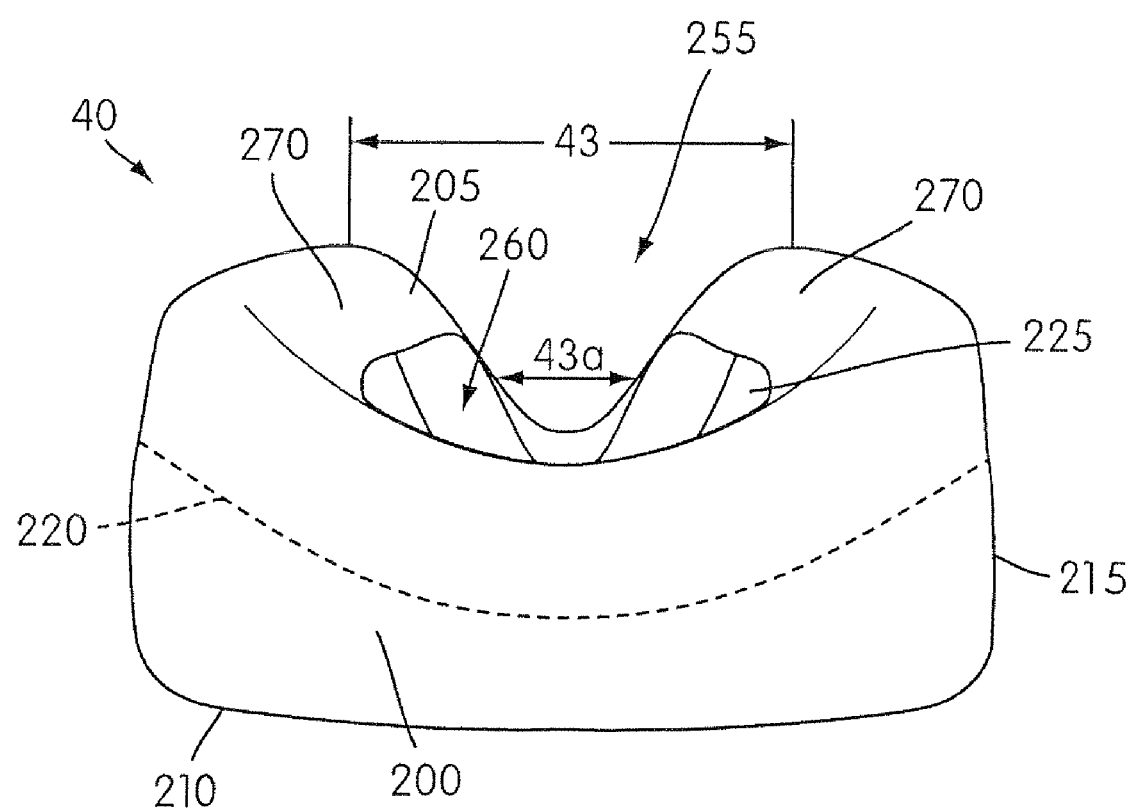
Figure 24F:
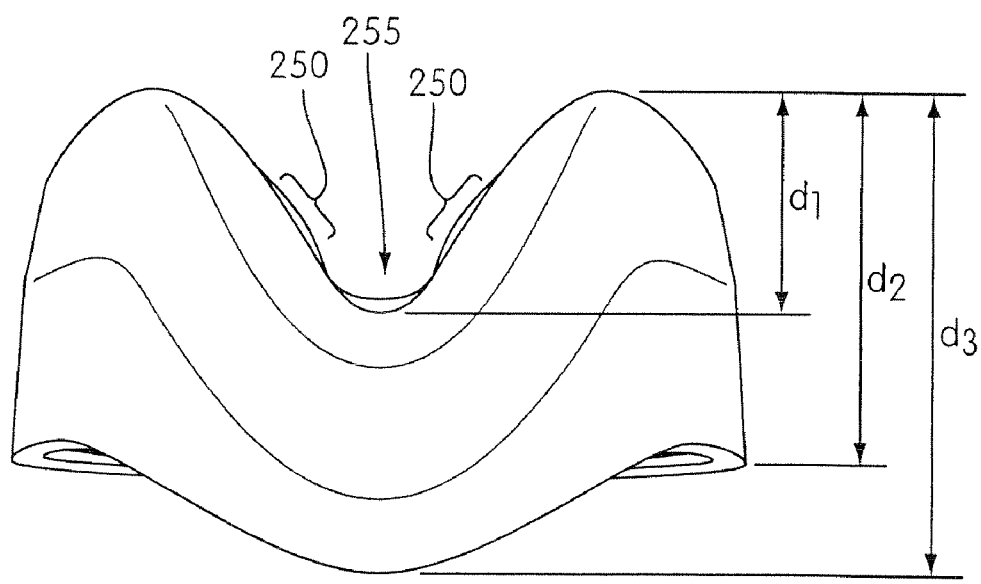
Figure 24G:
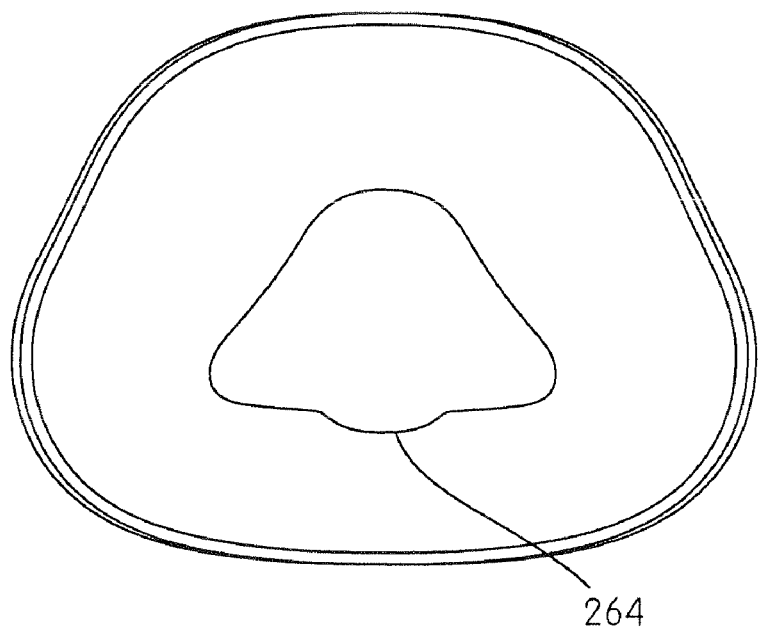
FIG. 24g shows a mask cushion in accordance with an embodiment of the invention incorporating a septum notch.

FIGS. 24a-g show additional views of the cushion 40. As shown in FIG. 24e, the cushion 40 includes a frame 200 and a membrane 205 attached to the frame. The frame 200 and membrane 205 are formed, for example, in a one-shot injection molding process as is known in the art, using, e.g., silicone such as SILASTIC™ with 40 durometer hardness. Of course, the frame 20 and the membrane 205 can be formed from two different pieces that are connected together and/or to the frame 20. The frame 200 has an edge 210, which may be attached to the channel 26 of the frame 20, as described in relation to FIGS. 27a-29d. The edge 210 of the frame 200 may be attached to the frame 200 with clips, straps, friction or interference, direct molding to the frame, adhesives and/or a tongue and groove arrangement, as is known in the art. The edge 210 and a central portion or sidewall 215 above the edge 210 has a thickness which is able to withstand buckling forces which can be applied when the cushion 40 is placed in engagement with the channel 26 of the frame. In one form the central portion 215 has a thickness of 2-10 mm, preferably 5 mm. The central portion 215 extends from the edge 210 to a transition line 220 where the thin membrane 205 joins with the underlying frame 200, between the frame 200 and the membrane 205. In the preferred embodiment, the height of the central portion 215 of the frame 200 is most in the cheek regions 41 and less in the lip and nasal bridge regions 42, 43.

Beyond the transition line 220, the frame 200 includes a rim 225. In a preferred form, the rim 225 has a curved shape that curves inwardly into the nasal cavity of the cushion 40. In an alternative form, the rim may be provided by a solid piece having a generally round cross-section. The membrane 205 forms a seal forming portion 270 (FIG. 24e) which contacts the patient in the lower nasal bridge region, cheek and lip regions 41-43. The rim 225 has a thickness that is preferably less than the central portion 215 of the frame 200, but preferably greater than the membrane 205. For example, the membrane 205 has a thickness in the range of between about 0.1-2.0 mm, and preferably 0.35 mm, while the rim 225 has a thickness of between about 0.5 and 2.0 mm, and preferably 1.35 mm. While it is preferable that the membrane 205 be thinner than the rim 225, they could have the same thicknesses. The membrane 205 completely covers and surrounds the rim 225 of the frame 200, as shown in FIG. 25. The inside surface of the membrane 205 is spaced from the outside surface of the rim 225 so as to form a compliant seal with the patient. By compliant seal, it is meant that the membrane 205 can accommodate small variations in the shape of a patient's facial/nasal features without undue force, and can account for small movement of the mask relative to the patient during use, while maintaining an effective seal. The membrane 205 is preferably spaced away from the rim 225 at least in the nasal bridge region 43, especially at a region 43a near the apex of the nasal bridge region 43 (FIG. 24c). This is because that area of the patient is most sensitive to localized contact pressure. Stated differently, the membrane 205 is preferably the only portion of the cushion 40 that contacts the patient to apply a sealing force to the patient in the lower portion of the nasal bridge region 43. The membrane 205 can better evenly distribute the force across the entire bridge of the nose, applying a lighter pressure, thereby improving comfort. Of course, the sealing force applied to the transition between the bony region and the cartilage region of the nose is not so great as to partially or wholly close the nasal vents.

The rim 225 in the nasal bridge region, especially at the apex thereof, is spaced a sufficient distance away from the membrane 205 to avoid localized pressure points or regions on the lower bridge region of the nose. Moreover, the rim 225 should be inwardly curved to evenly distribute forces which may cause the membrane 205 to contact the rim 225. Such forces may be the result of over tightening the headgear 80 or instability due to patient movement. The cushion 40 is designed to avoid contact between the rim 25 and the membrane 205 in the lower nasal bridge region even if the headgear 80 is over-tightened. In that event, the rim 225 in the lower nasal bridge region (at least at the apex 43a) can be eliminated to save material and weight, so long as the structural integrity of the cushion 40 is not compromised. Moreover, the rim 225 need not be curved along the entire perimeter thereof, especially those portions that are designed not to contact the membrane 205 in use.

Spacing between the membrane 205 and the rim 225 in the cheek and lip regions 41, 42 is not necessary, but will add comfort and enable the cushion 40 to fit a wider range of patients due to the compliant membrane 205.

A cushion in accordance with the invention provides improved stability over prior art cushions. The footprint, or contact area has been maximized, particularly along the sides of the nose. The side contact regions of the cushion have been maximized. This provides two further advantages. First, since the side walls of a cushion in accordance with the invention are longer than some prior art cushions, it is possible to design a mask which seals above the nasal vents but below the upper portion of the nasal bridge. Second, by distributing the contact pressure over a larger footprint, or contact area, stability of the mask assembly is improved. As such, the cushion 40 is much less likely to rotate in the vertical plane, as compared to prior art masks which tend to rotate about an axis substantially over the lip region.

Figure 25A:
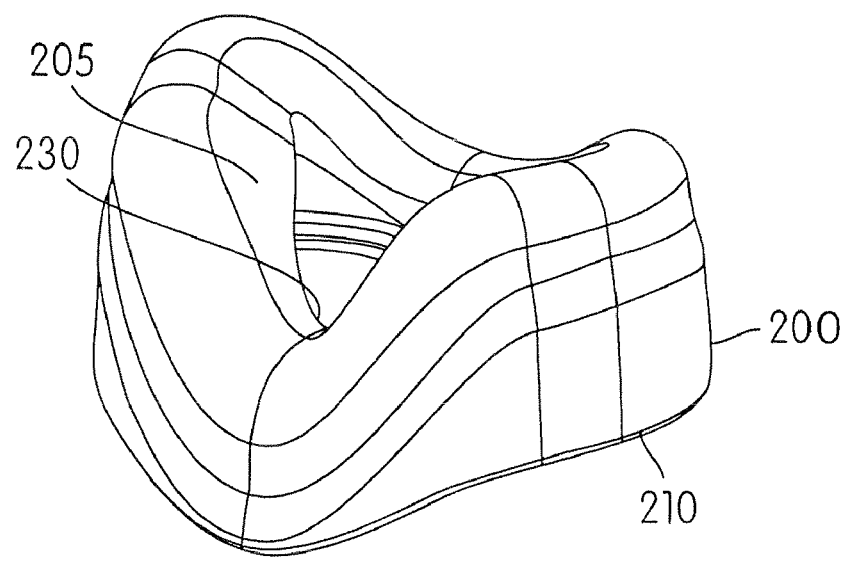
FIG. 25a is a perspective view of the cushion shown in FIG. 1 showing CAD construction lines.
Figure 25B:
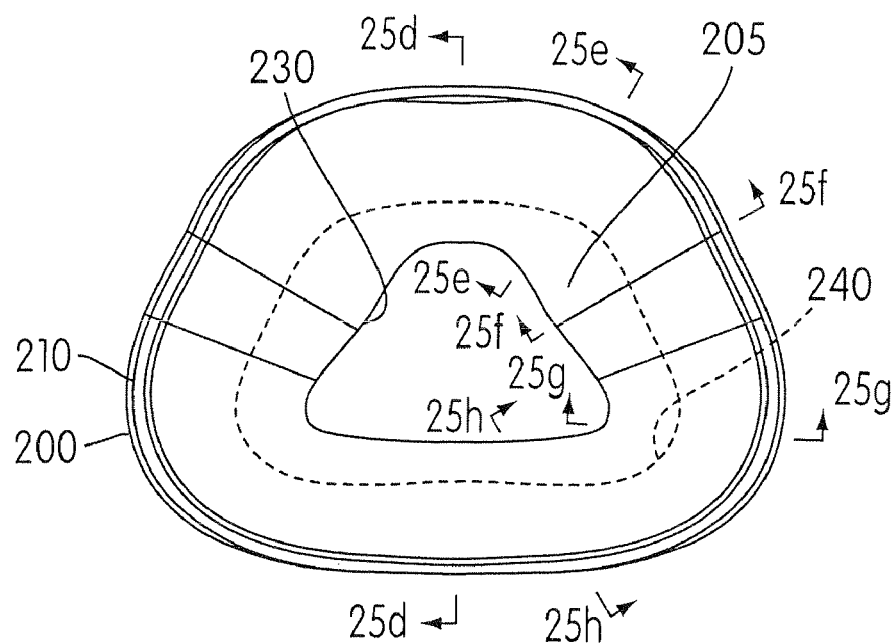
Figure 25C:
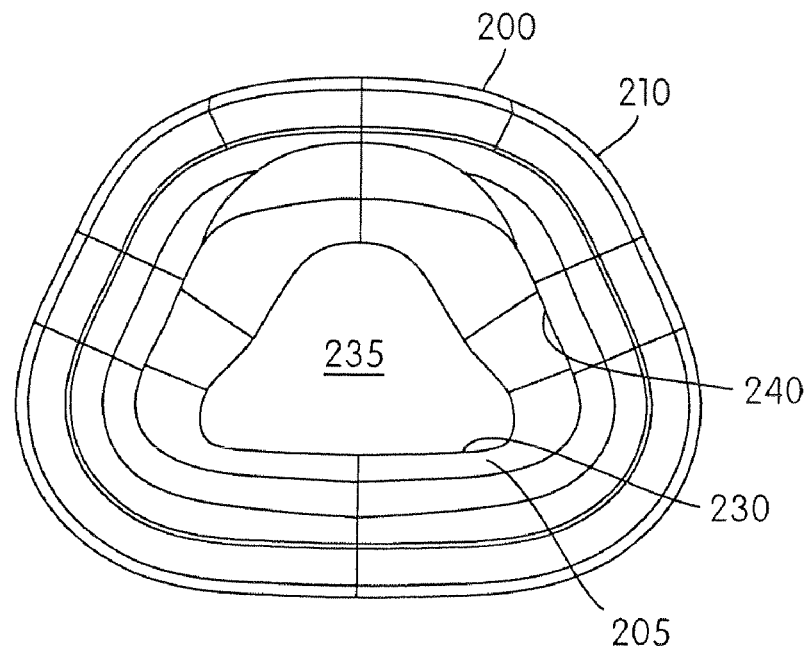
FIG. 25c is a frame side view of the cushion of FIG. 25a showing CAD construction lines.
Figure 25D:
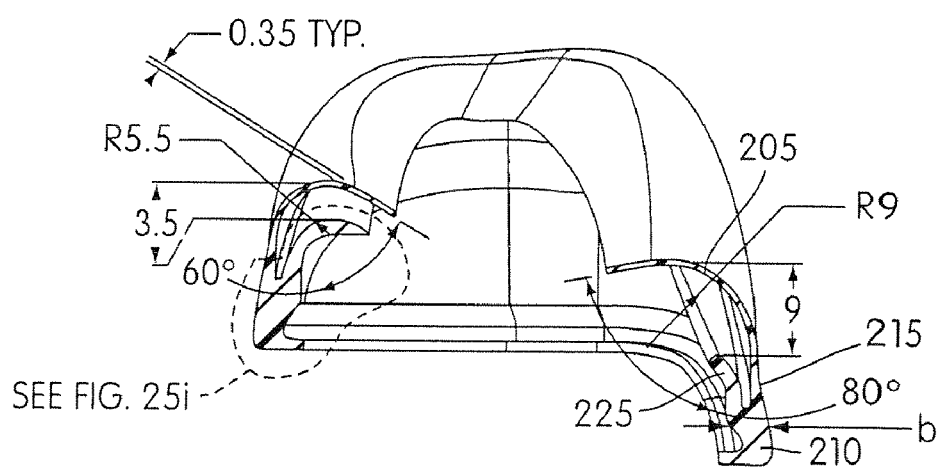
FIG. 25d is a cross-section taken along line 25d-25d of FIG. 25b showing CAD construction lines.
Figure 25G:
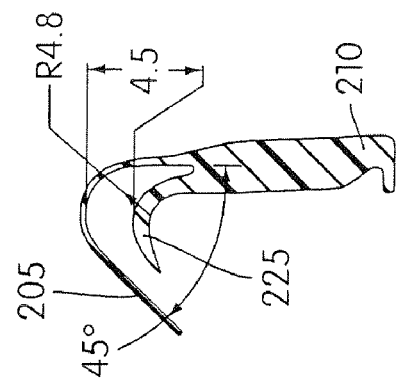
FIG. 25g is a cross-section taken along line 25g-25g of FIG. 25b.
Figure 25F:
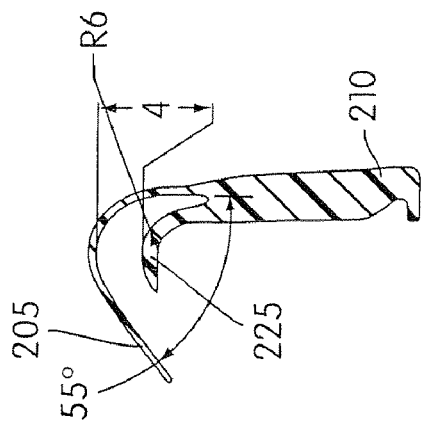
FIG. 25f is a cross-section taken along line 25f-25f of FIG. 25b.
Figure 25E:
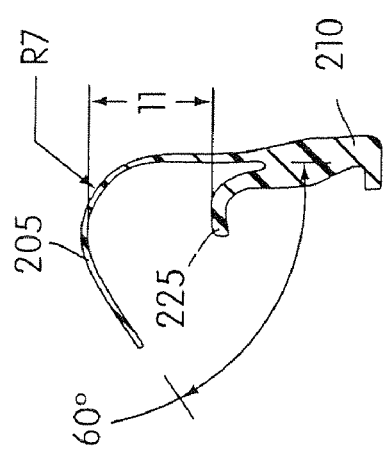
FIG. 25e is a cross-section taken along line 25e-25e of FIG. 25b.
Figure 25I:
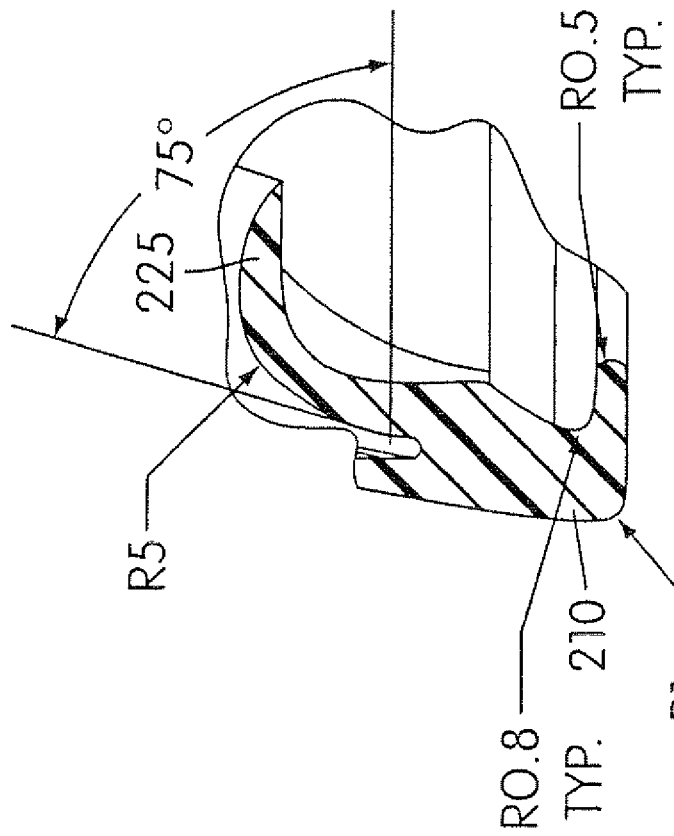
FIG. 25i is an enlarged view of FIG. 25d showing typical (TYP) dimensions of an embodiment (R-radius)
Figure 25H:
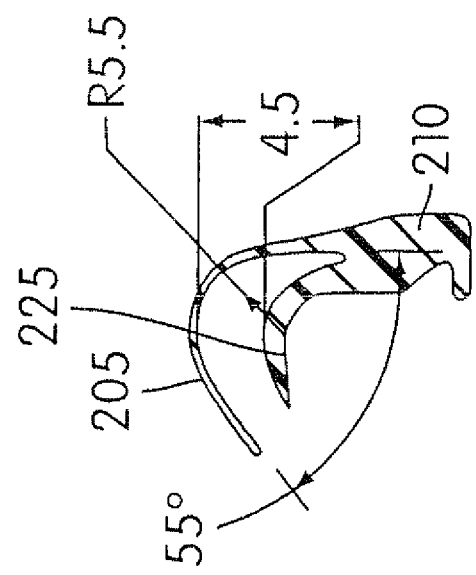
FIG. 25h is a cross-section taken along line 25h-25h of FIG. 25b.

FIGS. 25d-25i show cross sections of the cushion 40. As shown in FIG. 25d, the distance between the rim and the membrane in the nasal bridge region 43 is in the range of about 5-14 mm, preferably 9 mm. As shown in FIG. 25e, the distance between the rim and the membrane is in the range of about 7-16 mm, preferably 11 mm. As shown in FIGS. 25f, 25g, 25h, and FIGS. 25d and 25i in the lip region, the distance is in the range of about 1-6 mm, preferably 4 mm.

FIGS. 25d-25i also show various other dimensions in one preferred embodiment, such as the radii of curvature, the angles at which the membrane extends, etc. For example, at the apex of the nasal bridge region, in FIG. 25d, the radius of curvature of the membrane is in the range of about 5-14 mm, preferably 9 mm, with an angle of about 70-90 degrees, preferably 80 degrees. As shown in FIG. 25e, the radius of curvature is within the range of about 4-10 mm, preferably 7 mm, with an angle of about 50-70 degrees, preferably 60 degrees. Generally, the spacing in the nasal bridge region 43 should be more than the spacing in the cheek and lip regions 41, 42. Of course, a cushion with a combined membrane and rim could be provided as well, e.g., a one layer structure. Conversely, the support function of the rim 225 could be accomplished using two or more support rims to support the membrane 205, or two or more membranes could be provided over a single rim. In another alternative, the support function of the rim and the sealing function of the membrane can be split into two different members, which may be made of different materials.

FIG. 24e shows that the membrane 205 includes a preformed, contoured notch 255 in the nasal bridge region 43 to match generally the typical contours of the lower portion of the bridge region of the patient. The frame 200 includes a notch 260 which is co-located in relation to the notch 255. The shape of the notch 255 is generally U-shaped, while the shape of the notch 260 is generally wider than the notch 255, and the notch 260 is generally U-shaped. As shown in FIG. 24f, the notch 255 has a depth $d_1$ in the range of 12-27 mm.

As seen in FIGS. 24a-c, an inner edge 230 of the membrane 205 defines an aperture 235 of the membrane 205. In this preferred form, the shape of the aperture 235 is generally trapezoidal and has a base width w of about 31-45 mm, sides with a length s of 20-22 mm, and a top portion 1, generally parallel to the base portion with a length of about 5-10 mm. See FIG. 24c. The included angle α is in the range of 45°-55°, and preferably 50°. The height h between the base portion and the top portion of the membrane 205 is in the range of 19-22 mm. Further, the overall height $h_o$ of the cushion 40 is in the range of 45-55 mm, preferably 50-51 mm and the overall width $w_o$ of the cushion 40 is in the range of 65-75 mm, preferably 69-71 mm. Also, as shown in FIG. 24f, the dimension $d_2$ of the cushion is in the range of 29-31 mm and the dimension $d_3$ of the cushion is in the range of 41-43 mm. In one embodiment of a cushion 40 that has a "standard size", the membrane 205 of the cushion 40 has a width w in the range of 31-34 mm, preferably 33 mm, a height h in the range of 19-28 mm, preferably 22 mm, and the notch 255 has a depth $d_1$ in the range of 19-23 mm, preferably 21.5 mm. In another embodiment of a cushion 40 that has a "deep" size, the membrane 205 of the cushion 40 has a width w in the range of 31-34 mm, preferably 33 mm, a height h in the range of 19-28 mm, preferably 22 mm, and the notch 255 has a depth $d_1$ in the range of 22-27 mm, preferably 24 mm. In yet another embodiment of a cushion 40 that is wider and/or shallower in depth ("wide/shallow"), the membrane 205 of the cushion 40 has a width w in the range of 35-45 mm, preferably 41 mm, a height h in the range of 19-28 mm, preferably 22 mm, and the notch 255 has a depth $d_1$ in the range of 12-20 mm, preferably 16 mm. It is to be understood that these dimensions refer to a particular embodiment of the invention, and a differently sized mask (for example, a "small" size versus a "large" size) while having the same shape would have different dimensions and nevertheless be within the scope of the invention. Further, while the "standard" size cushion, "deep" size cushion, and "wide/shallow" size cushion may be provided individually, these cushions may be provided together as a set of cushions. This set of three cushions provides a good fit in a wide range of patients without having an excessive inventory.

The sides s of the membrane 205 adjacent the aperture 235 include a curved portion 250 (FIG. 24c) between the nasal bridge 43 and lip regions 41. The curved portion 250 appears as a bulged portion curving inwardly toward the aperture 235. In FIG. 24f, the curved portion 250 appears outwardly bulged in relation to the adjacent surfaces. FIG. 24e also shows the depth of the notch 255 provided in the membrane 205 in the nasal bridge region, as seen from the top view. FIG. 24d provides yet another view of the curved portion 250, and the shape of the membrane 205 in relation to the underlying shape of the rim 225. The curved portion 250 helps provide a good seal along the sides of the nose in the crevice where the cheek meets the nose. For example, as seen in FIG. 24c, the portion 250 is spaced away from the edge of the rim 225 so that more allowance for sealing in the crease and along the sides of the nose is provided. The edge 240 of the rim 225 and the edge 230 of the membrane 205 in the cheek region 41 begin diverge away from one another at an angle, as seen in FIG. 24c. The spacing between the edges 230, 240 of the membrane 205 and the rim 225 are smallest in the lip region 42, and gradually increases in the cheek regions 41, and is most in the curved portion 250 and nasal bridge region 43, as shown in FIGS. 25e-25i.

The inner edge 240 of the rim 225 which defines an aperture 245 is shown in FIG. 24b. The base width W of the aperture 245 is in the range of 38-45 mm. The length of each side S is in the range of 20-23 mm. The length of the top portion T is in the range of 15-20 mm. The height H between the base portion and the top portion of the is in the range of 32-36 mm. These dimensions, and all other dimensions provided herein, are preferred dimensions and could be changed depending on the particular application. While the shape of the aperture can also be characterized as generally trapezoidal, the trapezoid is not in the same proportions to the trapezoidal shape of the aperture 235 of the membrane 205. The aperture 235 is smaller than the aperture 245.

Further, the apertures 235 and 245 may have a triangular shape or other non-trapezoidal shape. Further, the overall shape of the cushion may be triangular or non-trapezoidal. The shapes of the apertures 235 and 245 and cushion may be similar to one another or may be different, e.g., the aperture 235 has a trapezoidal shape and the aperture 245 has a triangular shape.

The width of the membrane 205 as measured from the transition line 220 to the edge of the membrane 205 is greatest in the curved portion 250 and nasal bridge region 43, less in the cheek regions 41, and the least in the lip region 42. The membrane 205 generally extends upwardly away from the transition line 220 in the nasal bridge, cheek and lip regions 41-43. In the nasal bridge region 43, the membrane 205 curves inwardly along a generally constant radius to terminate at the edge 230. In the cheek regions 41, the membrane 205 curves around the rim 225 and then inwardly away from the rim 225 at an angle generally toward the opposite bottom position of the frame 200. In the lip region 41, the rim 225 and the membrane have substantially the same shape. See FIGS. 25d-25i.

Mask Frame and Cushion Connection System

The mask of the present invention may be fabricated in a manner where the mask frame and mask cushion are permanently attached to each other. For example, the mask frame and cushion may be formed from the same material in one piece where the elbow is attached as a separate piece. Alternatively, the mask frame and cushion may be formed as two pieces of the same or different material where the cushion and mask shell are attached in a permanent manner. The permanent attachment may be achieved through co-molding, adhesives, the use of clips or other mechanical means.

Alternatively, the mask frame and cushion may be attached by way of a method that allows for it to be detached and then re-attached repeatedly through the useful life of the mask, as will be described below. This allows for disassembly for effective cleaning and maintenance or even allows replacement if a part is worn out.

The mask shell and cushion connection system of the present invention allows for the manufacture of a combination mask frame and cushion that allows for the independent determination of forces for engagement of the cushion and disengagement of the cushion from the frame. Because of this ability, it is possible to fabricate a mask connection system where the engagement force is equal to the disengagement force, or where the engagement force is less than the disengagement force, or where the engagement force is greater than the disengagement force.

The connection system may be designed to achieve a disengagement force that is less than or greater than the force asserted upon the mask system at maximum treatment pressure.

Preferably the disengagement force (i.e. the force that will detach the cushion from the mask frame) will be greater than the force that would be asserted against the mask shell and cushion combination when the maximum treatment pressure is achieved in the mask chamber. By setting this lower limit for the disengagement force by reference to that force asserted against the frame and cushion combination, the likelihood of a mask disengaging during the application of treatment pressure is reduced.

While the minimum disengagement force is preferably determined by reference to the force asserted by treatment pressure, the maximum disengagement force ought to be no greater than the force that is capable of being comfortably exerted by a user when manually disengaging the mask to prevent inadvertent release and annoyance to the user. Preferably, the displacement force will be no greater than the force that may be comfortably exerted by a user.

The engagement force for the cushion (that is the force required to correctly connect the cushion to the mask shell) may be predetermined and achieved by adoption of the sealing and retaining mechanisms of the present invention.

Preferably the engagement force will be no greater than the force that may be comfortably exerted by the user. As the present invention has application in a mass-produced product range, preferably the maximum engagement force will be no greater than the force that may be exerted by the target user population. In a clinical setting that target population may be the clinical staff who will be fitting and applying the mask to patients. In a non-clinical setting that target population may be the population of end users. Preferably the target engagement force would be determined by considering the preferred engagement force that may be exerted by the target population when manipulating the mask shell and cushion in a conventional manner. Of course, these principles also apply to the disengagement force as well.

Figure 27C:
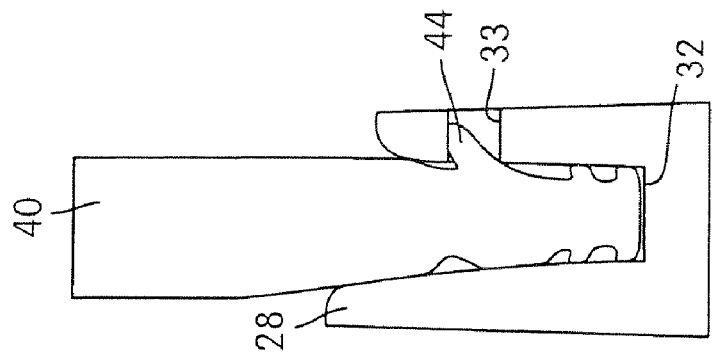
FIGS. 27a-27e are partial sectional views of a frame and cushion of the nasal mask assembly of FIG. 1 showing a sequence of positions of assembly and disassembly of the frame and cushion.
Figure 27B:
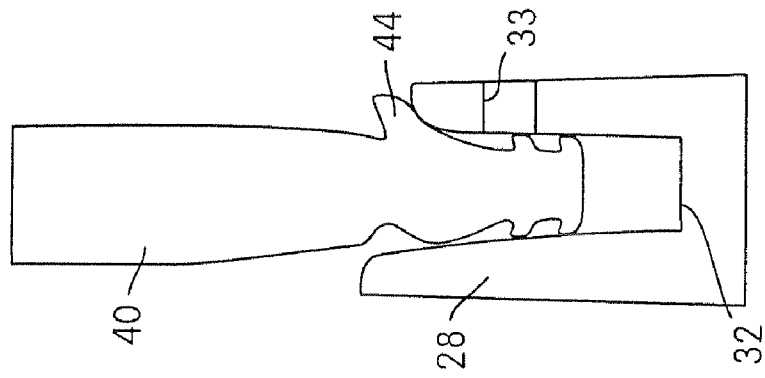
Figure 27A:
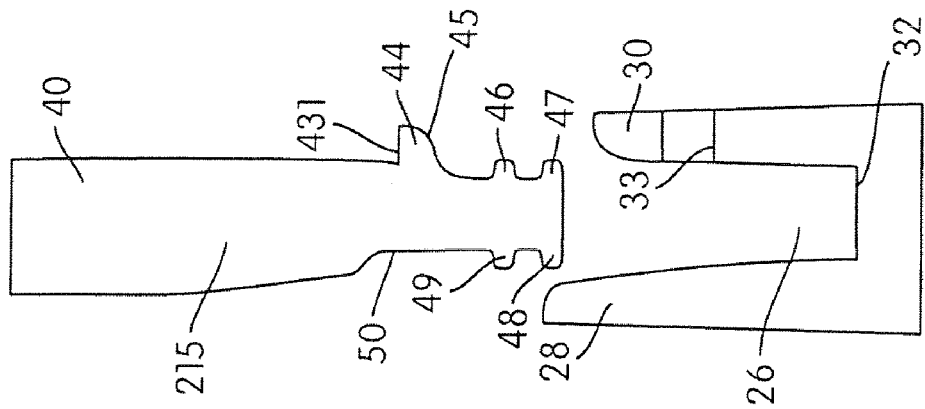
Figure 28:
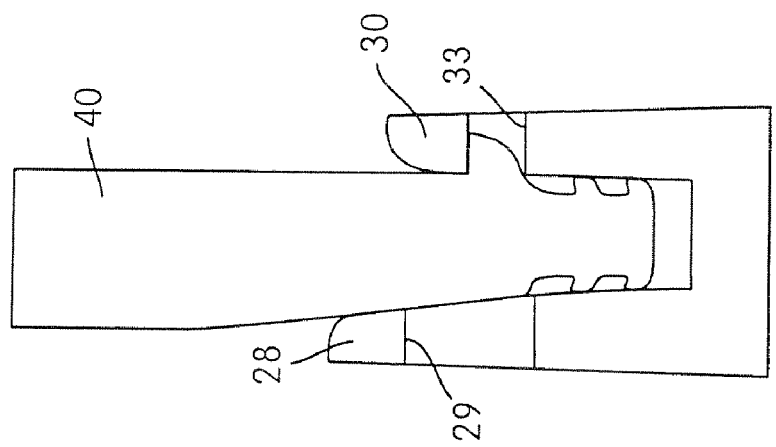
FIG. 28 is a partial sectional view of an alternative embodiment of the frame and cushion of the nasal mask assembly of FIG. 1.
Figure 27E:
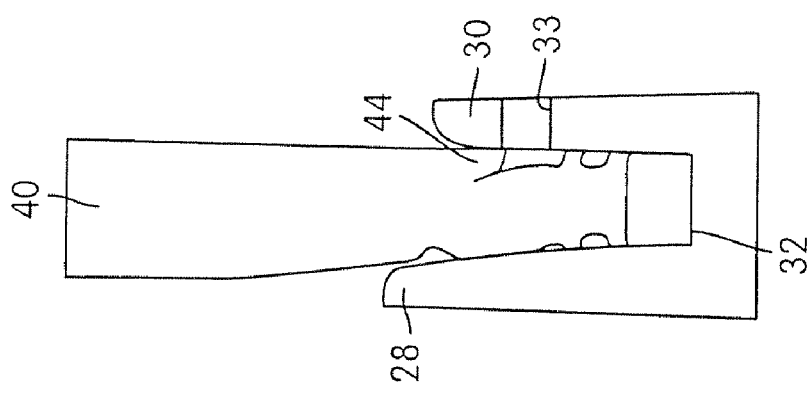
Figure 27D:
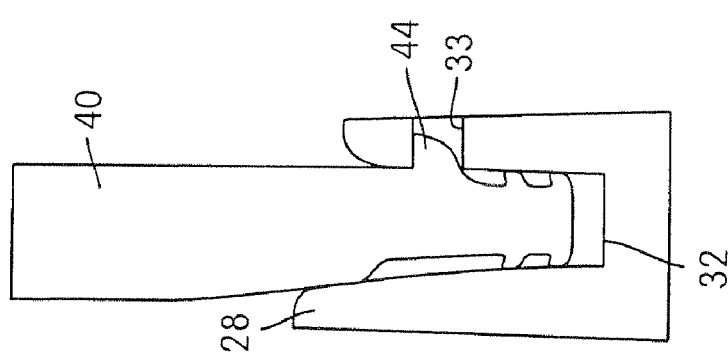
Figure 29B:
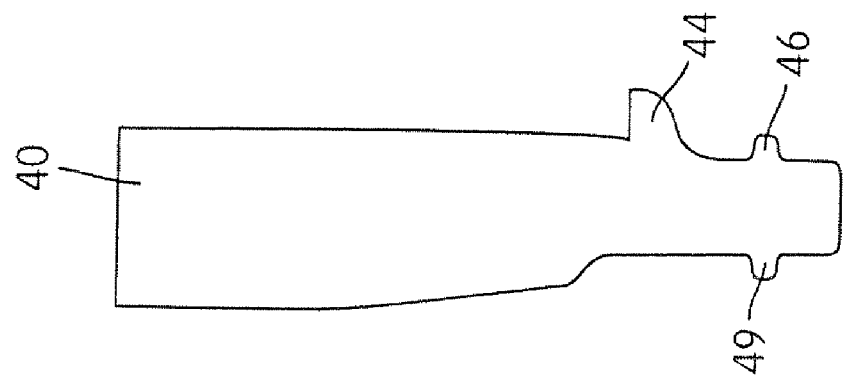
FIGS. 29a-29d show alternative sealing configurations of the cushion of FIGS. 27a-27e.
Figure 29A:
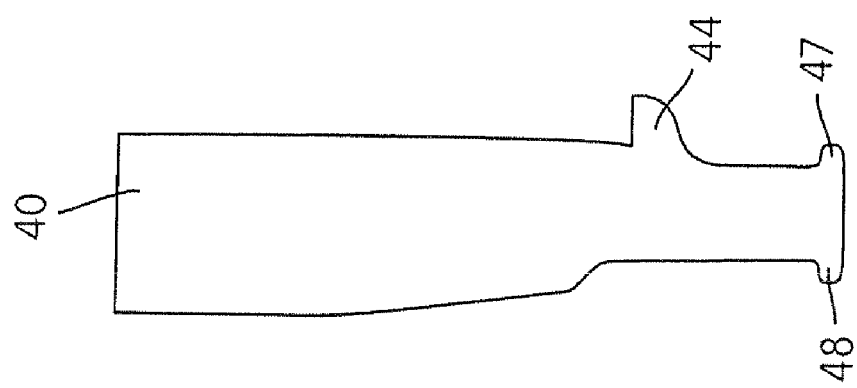
Figure 29D:
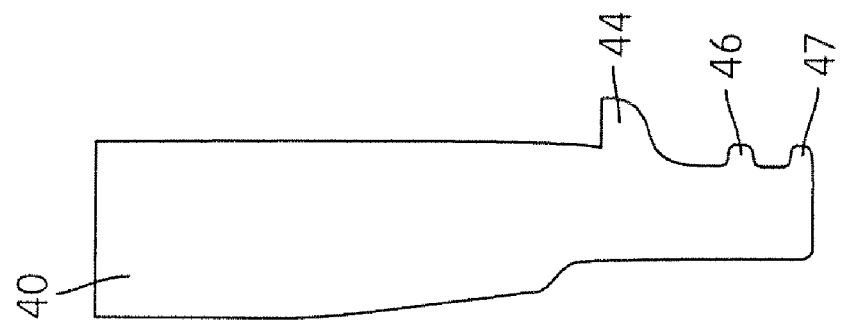
Figure 29C:
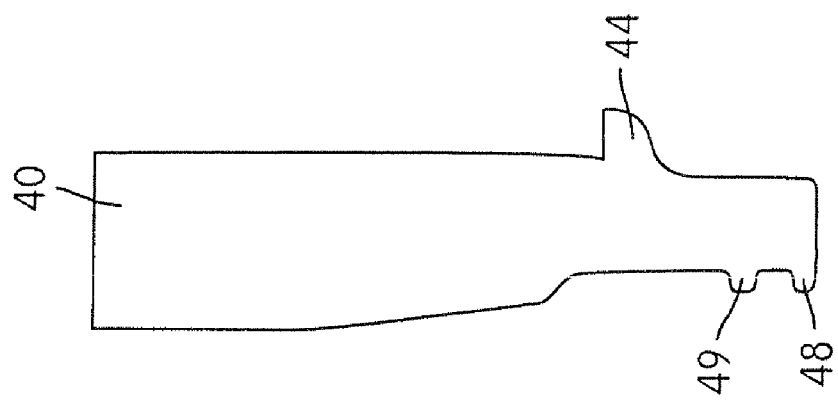

In one embodiment of the nasal mask assembly 10, an improved mechanism is used for engaging, i.e., retaining and sealing, the cushion 40 to the frame 20. See FIGS. 27a-29d. With the retaining and sealing mechanism, the cushion 40 can be fitted to the mask frame 20 in one movement that retains the cushion 40 and forms a secure seal with the frame 20. Outer wall 30 of channel 26 on frame 20 is provided with a plurality of undercuts 33 spaced around the outer wall 30. The undercuts 33 can pass partially or completely through the outer wall 30. A slight taper can be provided to the interior surfaces of inner wall 28 and outer wall 30 to ease assembly of the cushion 40 to the frame 20. The cushion 40 includes a side wall 215. As shown in FIG. 25d, the side wall 215 has a width b of about 5 mm. The side wall 215 includes a plurality of retention lips 44, spaced around the side wall 215 to align with the undercuts 33. Each retention lip 44 includes a leading edge 45, tapered to ease insertion of the cushion 40 into the channel 26, and a retention surface 431, shaped to catch the undercut 33 and prevent separation of the cushion 40 from the frame 20 until a predetermined separation force is applied between the cushion 40 and the frame 20. Preferably the predetermined separation force is designed to be greater than the force to insert the cushion 40 into the channel 26. Distally positioned on the side wall 215 are upper and lower sealing lips 46 and 47 extending outward from the side wall 215 and running around a periphery of the side wall 42. Opposite the sealing lips 46 and 47 are upper and lower sealing lips 49 and 48 extending inward from the side wall 215 and running around an inner periphery of the side wall 215. Opposite the retention lips 44, the inner surface of the side wall 215 has a relieved portion 50 thus creating a space between the wall of the cushion and the channel allowing the wall of the cushion 40 to distort into the relieved portion 50, as shown in FIGS. 27b and 27e, making insertion of the cushion 40 easier. The relieved portion 50 can be positioned just opposite each retention lip 44 or the relieved portion 50 can extend all the way around an inner periphery of the side wall 215.

Assembly of the cushion 40 to the frame 20 according to one embodiment of the invention will now be described. The cushion 40 is first generally aligned with the channel 26. See FIG. 27a. The inner wall 28 is slightly higher than the outer wall 30 to assist in aligning the cushion 40 with respect to the channel 26 before the cushion 40 enters the channel 26. The cushion 40 is then moved into the channel 26. See FIG. 27b. The leading edge 45 of each retention lip 44 will engage a top portion of the outer wall 30 and begin to deform. The relieved portion 50 of the side wall 215 allows this deformation to happen without greatly increasing the force necessary to insert the cushion 40 into the frame 20. The sealing lips 46-49 have contacted the respective surfaces of the inner and outer walls 28 and 30 of channel 26. The cushion 40 is further inserted into the channel 26 until it bottoms against the channel floor 32. See FIG. 27c. The sealing lips 46-49 are in full contact with the inner and outer walls 28 and 30. Each retention lip 44 has entered the respective undercut 33 but there is still deformation of the side wall 215, accommodated by the relieved portion 50. The cushion 40 is then slightly withdrawn as compression of the elastomer (Silastic™) relaxes from the channel 26, seating the retention surface 431 of each retention lip 44 against the respective undercut 33, with the sealing lips 46-49 in continuous sealing position around the inner and outer walls 28 and 30. See FIG. 27d. This withdrawal and seating provides a tactile signal to the user that the cushion 40 is properly seated in the channel 26. If the undercuts 33 are made visible to the user in this position, a visual indicator of seating is also provided. Deformation of the side wall 215 has generally been removed at this point and the relieved portion 50 returned to its relaxed configuration. Further withdrawal of the cushion 40 from the channel 26, to disassemble the cushion 40 from the frame 20 will deform the retention lip 44 downward. See FIG. 27e. This deformation of the side wall 215 will again be accommodated by the relieved portion 50. The shape of retention lip 44 results in the preferred more secure removal force compared to assembly force by the user.

Furthermore, where the cushion sealing lips or retention lip or both are made of a material that expands over time such as with some chemical cleaning exposure (i.e. increases in size in at least one dimension) such a material being silicone, the extra size or volume resulting from spread of material may be accommodated within the channel 26, say by the sealing lips or retention lip flexing. This aspect of the invention has advantages over the prior art in that the spread of cushion material ought not compromise the seal of the mask shell and cushion, thereby prolonging the useful life of the component made of the expandable material.

The prior art typically requires the cushion material to achieve a snug fit with the frame so as to prevent leakage of gas from the mask chamber via one or more paths between the frame and cushion. In addition some masks utilized an interior or exterior cushion clip to sandwich the cushion between the clip and the frame. Such cushion clips are found in Respironics' ComfortSelect mask, and in ResMed's Ultra Mirage™ mask, which is described in U.S. Pat. No. 6,412,487, incorporated herein by reference.

With the prior art, should the cushion be made of a material that spreads with time, there is a tendency for the material to increase in at least one plane to the extent that it becomes difficult to fit or disengage from the mask frame channel, or to otherwise make use of a cushion clip. Also, the seal to prevent gas escaping from the mask chamber is compromised due to gaps appearing between the cushion seal portion and the mask frame channel. The prior art limitations have been described with reference to a mask which has the sealing channel located in the frame and the sealing edge located on the cushion. However, similar limitations will apply where the location of these features are reversed, that is to say where the sealing channel is located on the cushion and the sealing edge is located on the mask shell as well as where the interface between the cushion and mask shell surface are in the form of flat surfaces.

As treatment pressure within the mask chamber is not being achieved during mask assembly, the selection of engagement pressure is not necessarily determined by reference to the force exerted during treatment. Rather, it is possible to fabricate the connection system of the present invention so as to achieve an engagement force that is less than the disengagement force—such a configuration, where the engagement force is less than the disengagement force is consistent with data that any given human population is typically capable of exerting a pulling force (i.e. where one or two hands move away from a starting point while gripping an object) than they are capable of exerting a pushing force (i.e. where one or two hands move towards a fixed point while gripping an object).

The embodiment described above can maintain the relationship of a disengagement force being greater than an engagement force notwithstanding that a dimension of a component may change over time—such as is the case where the cushion is made of a material that expands over time such as is the case with silicone.

The embodiments of the present invention also overcome the prior art limitation of loss of friction fit where at least one component such as the cushion is made of a material that tends to lose its frictional quality over time, such as with silicone which material tends to become 'greasy' due to chemical change and its own absorption of environmental pollutants, such as the patient's skin oil. Accordingly, the present invention addresses the prior art problem of a loss of engagement effect between the frame and cushion over time notwithstanding the loss of the friction between them.

While the present invention teaches away from the need for strap, clip or other additional retaining devices, such devices may be included in the fabrication so as to add further security of engagement between frame and cushion or to otherwise reduce the design tolerances required to achieve a disengagement force that is consistent with the upper limit considered appropriate for the target population while maintaining engagement during the maximum treatment pressure.

The cushion 40 includes at least one sealing lip which functions to prevent escape of gas from the mask chamber via the interface between frame and cushion. Preferably there are provided at least two seal lips each having relatively small contact points with the frame channel 26 as shall be described so as to minimize the friction occurring during assembly and disassembly of the cushion with the frame without compromising the seal.

If one seal lip were used, then its configuration to achieve adequate sealing may require it to assert greater friction once in position than would be the case where there were adopted two or more seal lips of the same material.

By control of this source of friction, it is possible to influence the engagement and disengagement forces, i.e., the forces required to engage and disengage the cushion and frame. The preferred aim being to have those forces remain with defined limits for the expected useful life of the cushion.

The relieved portion 50 of the side wall also accommodates deformation of the side wall 215 upon assembly and disassembly of the cushion 40 and frame 20, thereby reducing the force necessary for assembly/disassembly. This is especially important where the cushion 40 is made from a pliable but generally slightly compressible material, such as silicone. Alternatively, the inner wall 28 can be provided with an undercut 29 opposite each undercut 33 to accommodate deformation of the side wall 215. See FIG. 28. The undercut 29 (and/or relieved portion 50) can be sized and configured as desired to best accommodate the expected side wall deformation. Different combinations of the sealing lips 46-49 can alternatively be used. See, for example, FIG. 29a (sealing lips 47 and 48), FIG. 29b (sealing lips 46 and 49), FIG. 29c (sealing lips 48 and 49) and FIG. 29d (sealing lips 46 and 47). Other configurations of sealing lips and retention lips can also be used. This configuration separates the sealing function of cushion to frame from the functions of cushion and frame engagement and retention, so that each may be independently controlled and optimised in device configuration and fabrication.

Figures 2, 32B:
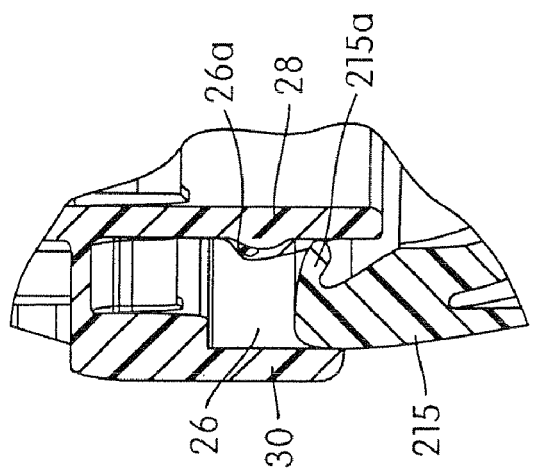
Figures 1, 32B:
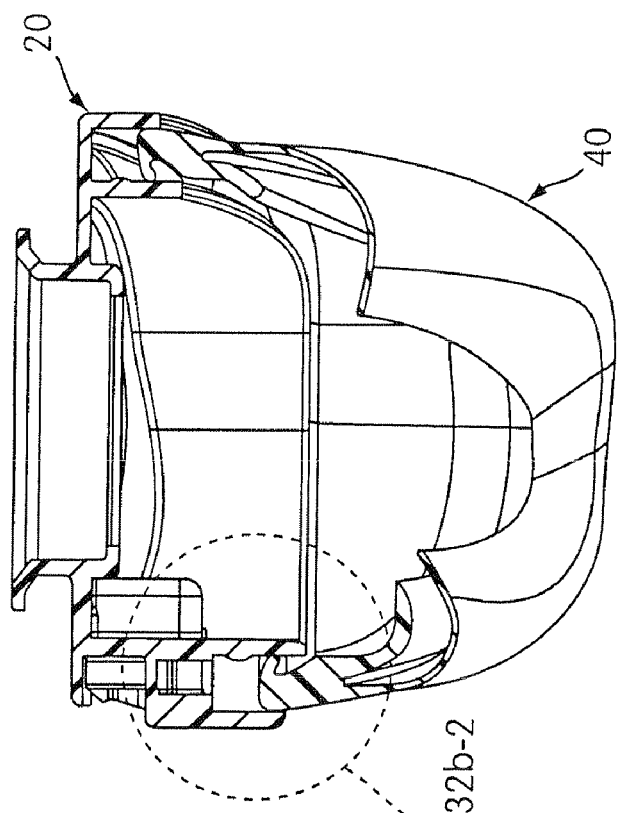
Figure 32D:
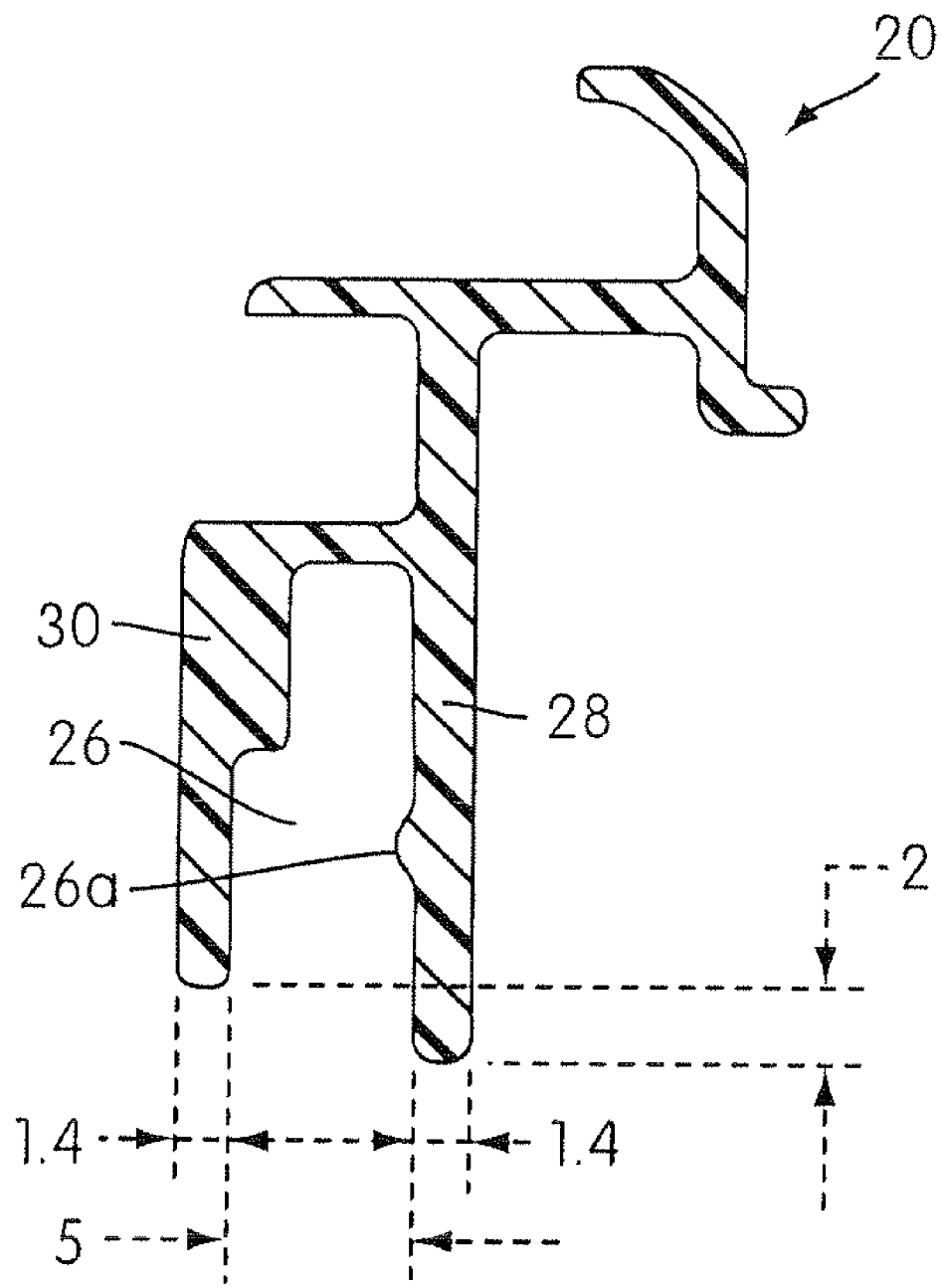
FIG. 32d is an enlarged cross-sectional view of the frame shown in FIGS. 32a-1-32c-2.

FIGS. 32a-1-32c-2 show sequential engagement between the frame 20 and the cushion, according to another embodiment of the present invention. In this embodiment, the side wall 215 has been changed, as well as the channel 26 which receives the side wall 215. FIGS. 32a-1-32a-2 show the frame and cushion before engagement, FIGS. 32b-1-32b-2 show the frame and cushion during engagement and FIGS. 32c-1-32c-2 show the frame and cushion in full engagement.

In this embodiment, the side wall 215 preferably includes an integral lug 215a at a distal end of the side wall 215. The side wall 215 includes an undercut 215b which allows the lug 215a to flex toward the side wall 215. During insertion (FIGS. 32b-1-32b-2), the lug 215a flexes into the undercut 215b until it is pushed beyond a protrusion 26a in the channel 26. After passing the protrusion 26a, the lug 215a flexes into a space of the channel 26 below the protrusion 26a. Therefore, the tip of the lug is positioned to be resiliently locked in place with the cushion 40 fully and securely connected to the frame 20. In the connected condition, the side wall 215 provides a secure seal with the frame 20 against escape of pressurized gas from the nasal cavity. Engagement between the tip of the lug 215a and the protrusion 26a provides a retaining force to maintain the cushion in engagement with the frame. To disengage, the patient pulls the side wall 215 out of the channel 26 with a force sufficient to cause the lug 215a to deform and overcome the protrusion 26a. Both engagement and disengagement require a force that is enough to overcome the frictional contact between the walls of the channel 26 and side wall 215. As the angle of protrusion 26a is substantially away from the insertion direction, it acts in much the same way as a "barb" allowing the preferred lower insertion force compared to disassembly force of the cushion to mask frame.

Figure 32E:
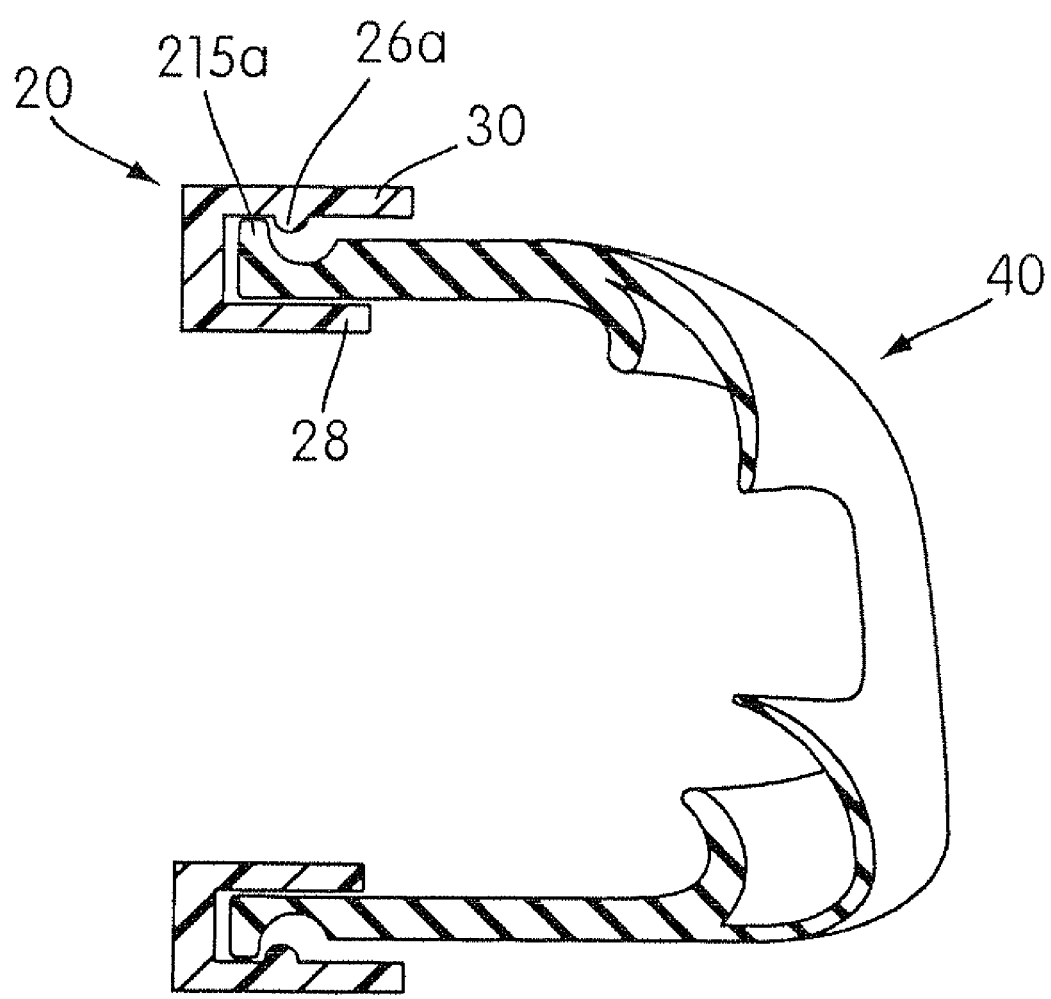
FIG. 32e illustrates an additional embodiment of the present invention for engagement between the frame and cushion.

In the illustrated embodiment, the lug 215a at the distal end of the side wall 215 extends generally inwardly towards the breathing cavity of the cushion. However, as shown in FIG. 32e, the lug 215a may extend generally outwardly from the breathing cavity of the cushion 40 and engage a protrusion 26a provided on the outer wall 30 of the frame 20.

Figure 40:
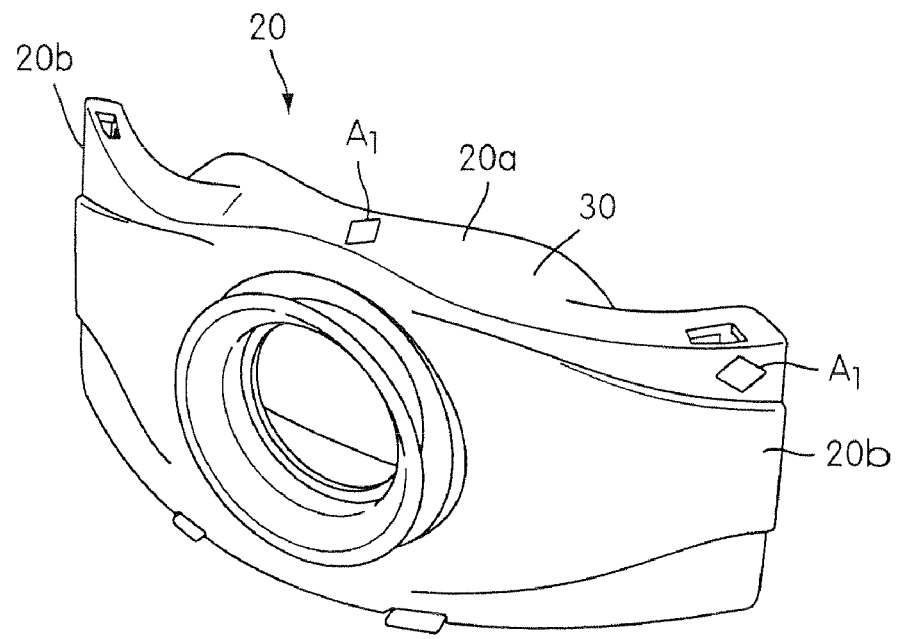
FIG. 40 is a perspective view of another embodiment of a frame of the nasal mask assembly.
Figure 41:
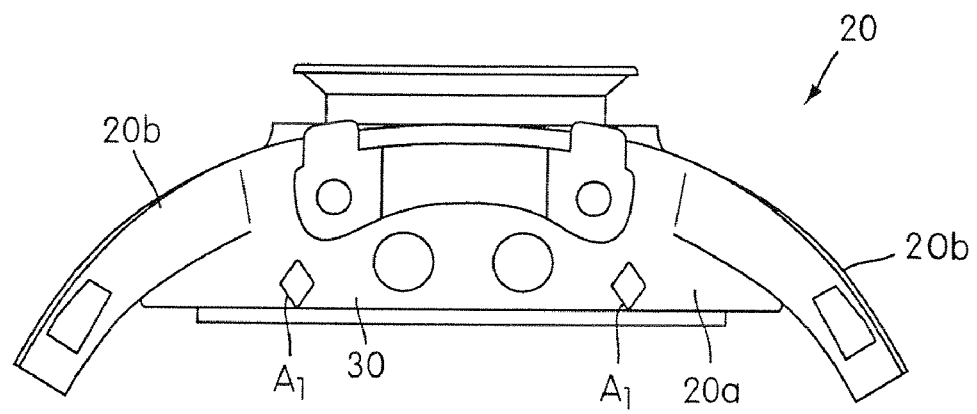
FIG. 41 is a bottom view of the frame shown in FIG. 40.

FIGS. 40-41 illustrate another embodiment of the frame 20 that is structured to facilitate the engagement between the frame 20 and the cushion 40. Specifically, the main body 20a of the frame includes alignment symbols $A_1$, e.g., diamonds, lines, colors, arrows, etc., on the outer surface of the outer wall 30 thereof. FIG. 40 illustrates a single alignment symbol $A_d$ provided on an upper portion of the outer wall 30 and FIG. 41 illustrates a pair of alignment symbols $A_1$ provided on a lower portion of the outer wall 30.

Figure 38A:
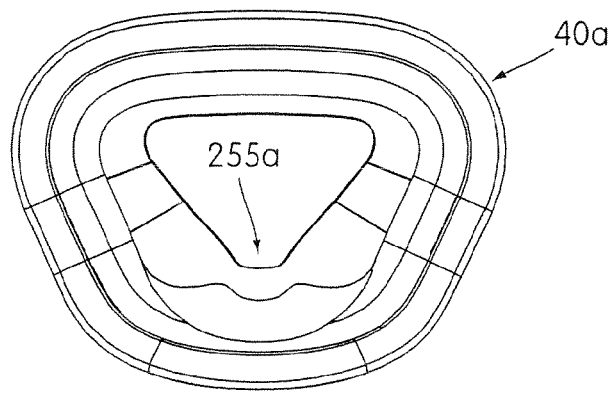
FIGS. 38A-38D show various perspectives of another embodiment of the cushion, the cushion showing CAD construction lines.
Figure 38B:
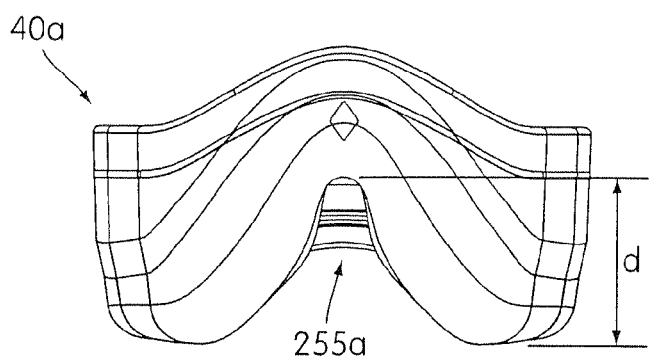
Figure 38C:
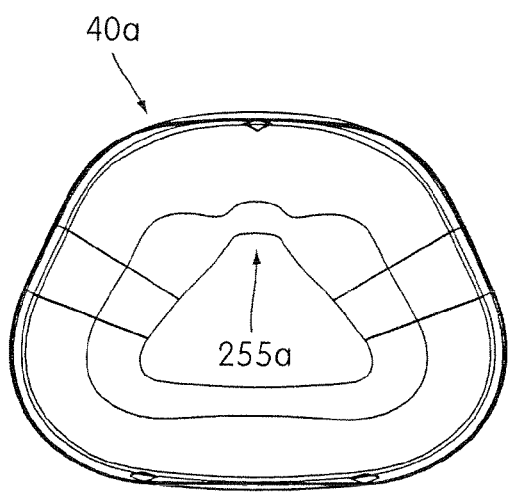
Figure 38D:
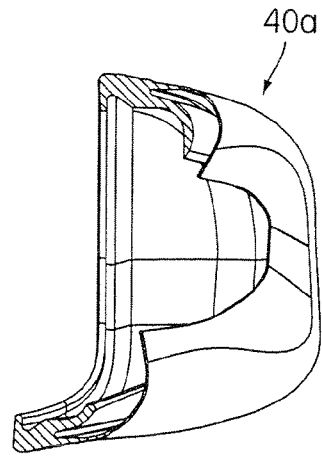
Figure 39A:
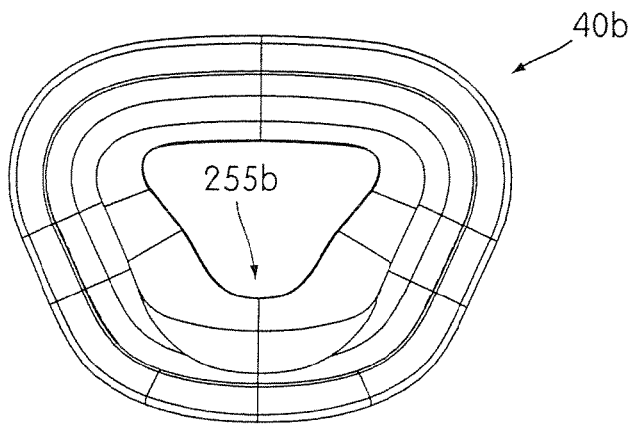
FIGS. 39A-39D show various perspectives of another embodiment of the cushion, the cushion showing CAD construction lines.
Figure 39B:
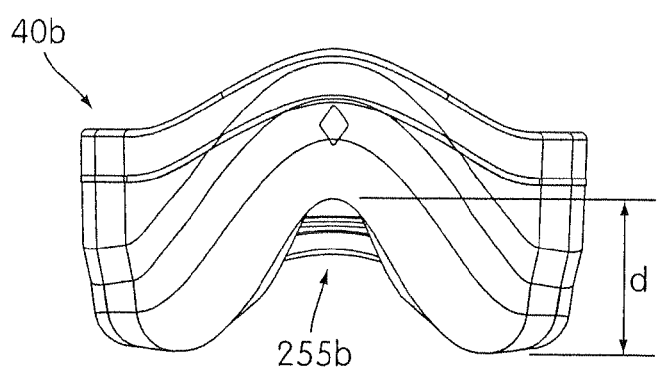
Figure 39C:
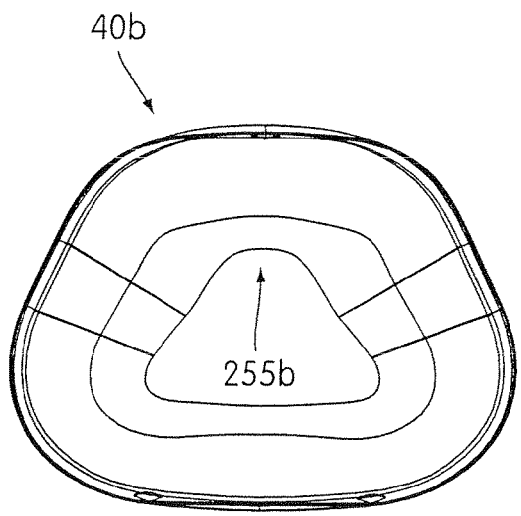
Figure 39D:
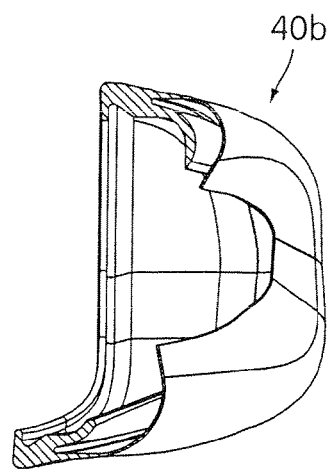
Figure 42:
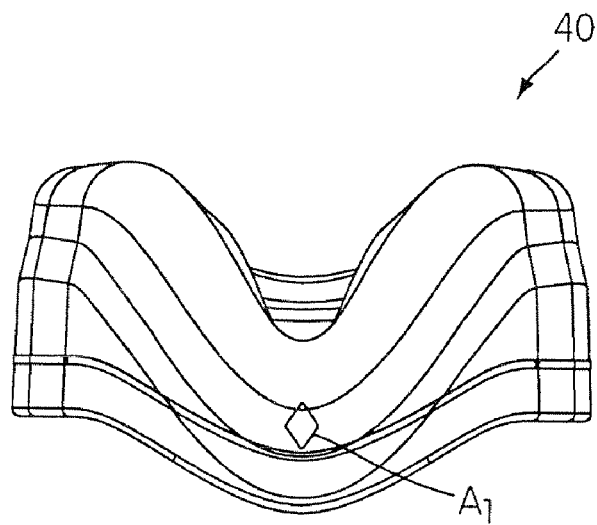
FIG. 42 is a top view of an embodiment of the cushion structured to be engaged with the frame shown in FIG. 40, the cushion showing CAD construction lines.
Figure 43:
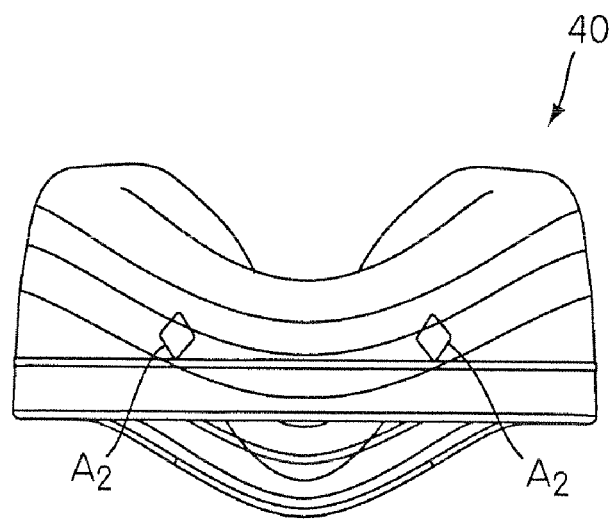
FIG. 43 is a rear view of the cushion shown in FIG. 42, the cushion showing CAD construction lines.

The cushion 40 includes alignment symbols $A_2$, e.g., diamonds, lines, colors, arrows, etc., on the outer surface thereof that are positioned to align with the alignment symbols $A_1$ provided on the frame 20 when the cushion 40 and frame 20 are engaged with one another. FIGS. 38B, 39B, and 42 illustrate a single alignment symbol $A_2$ provided on the outer surface of the cushion 40 in the nasal bridge region and FIG. 43 illustrates a pair of alignment symbols $A_2$ provided on the outer surface of the cushion 40 in the lip region. When the cushion 40 and frame 20 are engaged with one another, the alignment symbol $A_1$ on the upper portion of the frame 20 aligns with the alignment symbol $A_2$ in the nasal bridge region of the cushion 40. Similarly, the pair of alignment symbols $A_1$ provided on the lower portion of the frame 20 align with the pair of alignment symbols $A_2$ in the lip region of the cushion 40. The alignment of the alignment symbols $A_1$, $A_2$ on the frame 20 and cushion 40, respectively, ensures that the frame 20 and cushion 40 are correctly aligned and oriented with respect to one another. That is, the patient can correctly engage the frame 20 and cushion 40 by ensuring that the alignment symbols $A_1$, $A_2$ on the frame 20 and cushion 40 are correctly aligned with one another.

The alignment symbols $A_1$, $A_2$ may have any suitable configuration, e.g., diamonds, lines, colors, arrows, etc. Also, any corresponding number of alignment symbols $A_1$, $A_2$ may be provided on the frame 20 and cushion 40. In the illustrated embodiment, the upper portion of the frame 20 and the nasal bridge region of the cushion 40 have a different number of alignment symbols $A_1$, $A_2$ than the lower portion of the frame 20 and the lip region of the cushion 20. However, the upper and lower portions of the frame 20 and the respective nasal bridge and lip regions of the cushion 40 may have the same number of alignment symbols $A_1$, $A_2$ so long as the alignment symbols $A_1$, $A_2$ are positioned to facilitate correctly engaging the frame 20 and the cushion 40 in the correct orientation. Further, the alignment symbols $A_1$, $A_2$ may be positioned at any suitable location along the outer surfaces of the frame 20 and the cushion 40 to facilitate the engagement between the frame 20 and the cushion 40.

As shown in FIG. 40, the frame 20 may include alignment symbols $A_1$, e.g., diamonds, lines, colors, arrows, etc., on the side frame members 20b which are structured to facilitate the engagement between the frame 20 and the headgear assembly 80. Specifically, the locking clip 82 of the headgear assembly 80 may include alignment symbols, e.g., diamonds, lines, colors, arrows, etc., on the outer surface thereof that are positioned to align with the alignment symbols $A_1$ provided on the frame 20 when the locking clip 82 and frame 20 are engaged with one another.

Other Aspects

A nasal cushion was designed taking into account the shape and size of the nose of the patient, along with the size and shape of the surrounding facial features, such as the upper lip, the cheeks, etc. See FIGS. 30-31. While there is little statistical information regarding the sizes and shapes of those patients likely using or in need of some sort of NPPV treatment, Applicants have discovered that a select amount of criteria can be used to statistically model the cushion 40 to fit a vast majority of the patient population (e.g., 80% of the patient population). For example, the cushion 40 may be structured to accommodate 60-90% of patient population, regardless of age, sex, or race. However, the cushion 40 may be structured to accommodate up to 70% or up to 80% of patient population, for example. Using nasal width, nasal tip protrusion and nose height, Applicants have been able to design the cushion such that a large proportion of the population likely to be in need of nasal masks can be accommodated comfortably with the same sized cushions/masks. One or two additional cushions/masks can be designed to accommodate other parts of the population. Age, race and sex of the patient can be factors in computer modeling the cushion. Moreover, by designing a cushion in which contact with the upper portion of the nasal bridge portion is avoided, Applicants have been able to eliminate one of the factors which limits the designs of cushions in general.

Figure 30:
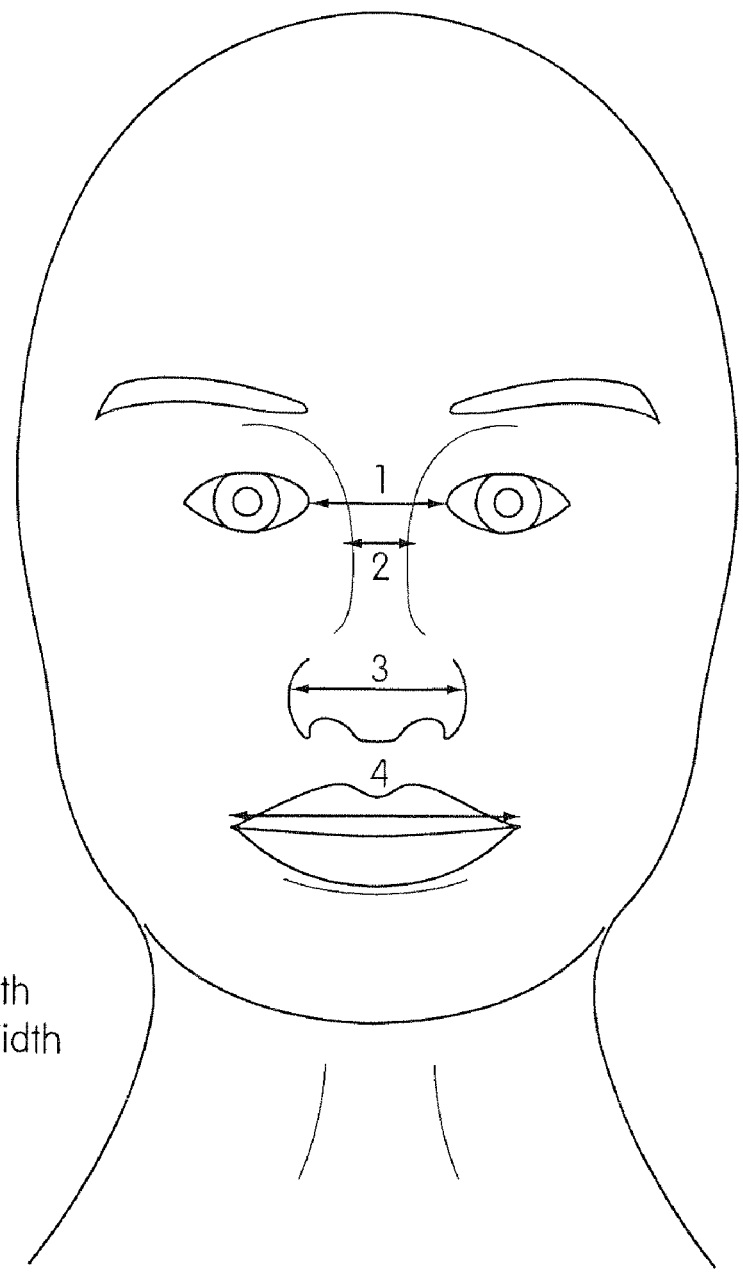
FIGS. 30 and 31 show various dimensions used to design a mask according to FIG. 1.
Figure 31:
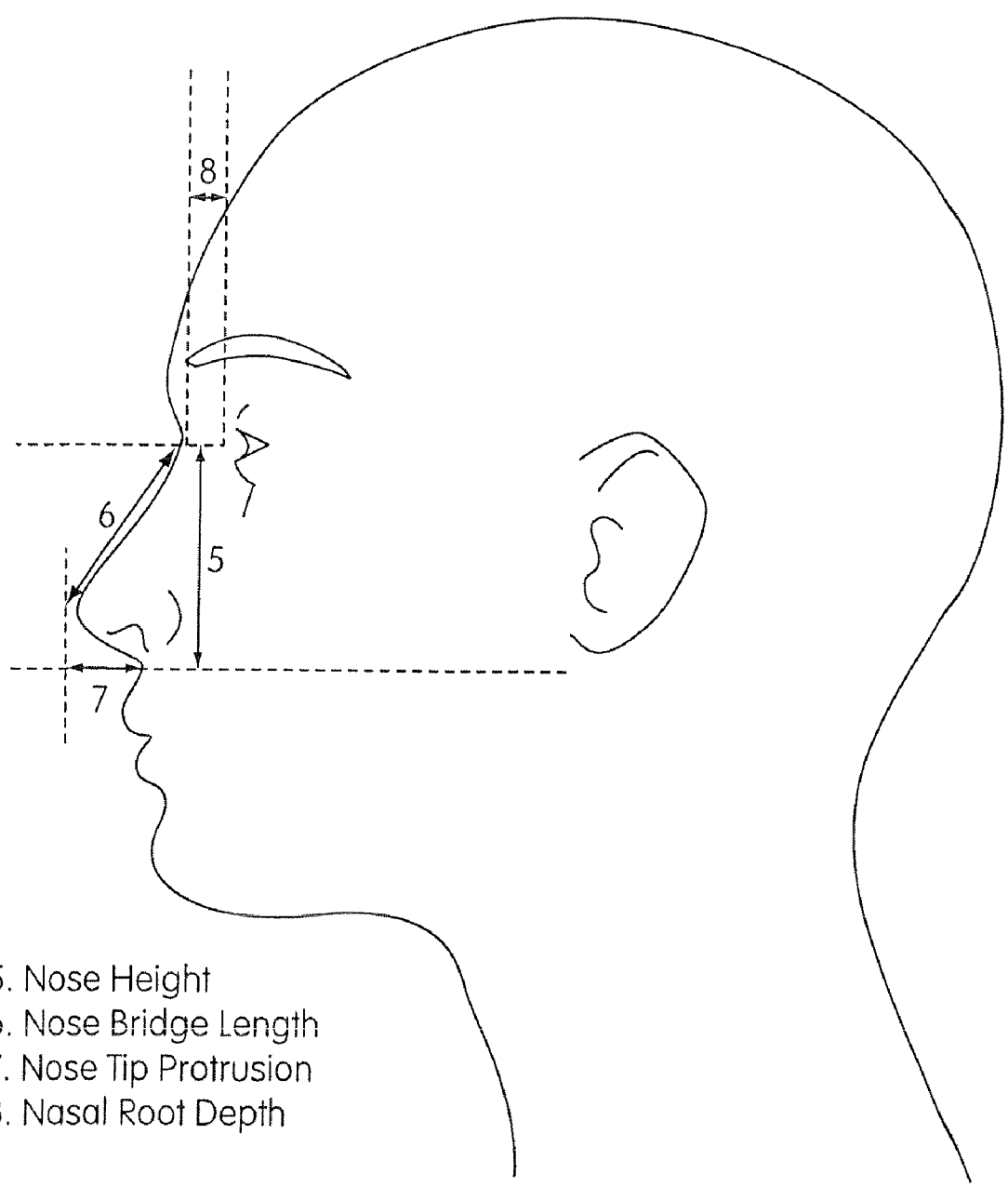

As shown in FIGS. 30 and 31, the nasal width determines the width of the opening in the cushion 40. Nasal tip protrusion describes minimum depth of cushion and mask frame combined. This is measured from the bottom of the septum. A mask with too much depth may result in excessive dead space within the nasal cavity that increases undesirable $CO_2$ re-breathing and movement of the center of gravity of the mask assembly further away from the face decreasing stability. Nose height reflects the distance between both sets of width/depth dimensions.

In general, cushions are sized to fit one or more maximum dimensions. However, user testing is important in verifying clearance at the nasal vent. If too large, the cushion may interfere with the eye area. The cushion is designed to sit low on the nasal bridge; possible interference in this area is minimized. If the cushion is too small, e.g., if the cushion applies pressure along the soft part of the nose that may collapse, the nasal vent may be partially or fully occluded, causing breathing restriction, as can occur with some prior art masks such as the Respironics Simplicity mask. Nose width, height and tip protrusion can be arrived at by reference to anthropometric data tables.

In one embodiment of the mask system, the mask system is designed to include a frame and a plurality of cushions that are each connectable with the frame. Each cushion would be configured to accommodate a percentage of the patient population such that the plurality of cushions, preferably 1-3 cushions, would together accommodate up to 95-100% of the patient population.

Thus, the plurality of cushions would each have a similar frame contacting side but a different face contacting side. Each cushion would have at least one parameter on the face contacting side that is different from the remaining plurality of cushions. In one embodiment, each cushion may differ in the nasal bridge region. For example, the cushion 40a shown in FIGS. 38A-38D has a deeper contoured notch 255a in the nasal bridge region than the contoured notch 255b in the nasal bridge region of the cushion 40b shown in FIGS. 39A-39D. Specifically, the contoured notch 255a has a depth d in the range of 22-27 mm, preferably 24 mm and the contoured notch 255b has a depth d in the range of 19-23 mm, preferably 21.5 mm. As illustrated, the notch 255a has a smaller radius of curvature than the radius of curvature of notch 255b. In another embodiment, each cushion may differ in the width of the aperture of the membrane. The plurality of cushions may be color coded to help distinguish the different cushions from one another.

Appendix A of incorporated U.S. Provisional Application of Moore et al., Ser. No. 60/402,509, includes various pictures of the mask system according to one preferred embodiment of the present invention. Appendix A also includes various pictures of the mask system according to other embodiments of the present invention. For example, an embodiment of the frame is provided that illustrates a frame having oxygen or pressure ports. See, e.g., FIG. 41. Further details of oxygen or pressure ports in a frame are included in U.S. Pat. No. 6,439,230, the entirety of which is hereby incorporated by reference. Appendix A also includes instructional information for the mask system. Appendix B of incorporated U.S. Provisional Application of Moore et al., Ser. No. 60/402,509, includes pictures of two prior art masks discussed in the present invention. Appendix C of incorporated U.S. Provisional Application of Moore et al., Ser. No. 60/402,509, includes pictures of two testing models (A+B) with widely varying nose and facial features, and the mask assembly of the present invention as well as one prior art mask connected to each model. Appendix C also includes a series of pictures comparing one embodiment of the present invention to a prior art cushion used for the MIRAGE® mask, See, e.g., U.S. Pat. No. 6,112,746 to Kwok et al., incorporated herein by reference. Generally speaking, the mask assembly of the present invention generally conformed to both nose models even though the sizes and shapes were vastly different. The mask cushion 40 also was able to successfully accommodate the deformity on model B. The mask assembly of the prior art tended not to fit the shape of the nose models, especially the shape of the smaller nose model where significant gaps are seen. One prior art model (see U.S. Pat. No. 5,724,965) was relatively unstable and tended to rock on the cheeks of the models, especially the smaller nose model.

It is intended that the components, elements and features of the various above-described embodiments can be used together in any desired combination or permutation to create new mask embodiments. For example, while the invention has been described in relation to a nasal mask, the teachings are also applicable to oro-nasal and full-face masks as well.

What is claimed is:

1. A frame for a respiratory mask assembly that delivers breathable gas to a patient, the frame comprising:
   a main body having a front surface and a rear surface adapted in use to face the patient, the main body having an aperture extending through the front surface for the introduction of breathable gas into a nasal breathing cavity defined by the frame; and
   an inner wall and an outer wall each extending rearwardly from the rear surface, the inner and outer walls being spaced to define a channel therebetween that is structured to receive a side wall of a cushion such that the cushion may be repeatedly attached to and detached from the frame, wherein the main body and the inner and outer walls are formed in one piece and the inner and outer walls are spaced in parallel, wherein a length of the inner wall is different than a length of the outer wall such that the inner wall protrudes away from the rear surface a distance that is different than a distance the outer wall protrudes away from the rear surface,
   wherein at least a portion of the channel is shaped and dimensioned to generally follow a contour of the patient's face, and wherein the channel has a generally triangular shape, and wherein the side wall of the cushion is adapted to be positioned between the inner and outer walls when attached to the frame.

2. A frame according to claim 1, further comprising a headgear assembly removably attachable to the frame, wherein the main body accommodates the cushion and a side frame member provided on each lateral side of the main body, each side frame member including an integrally formed first connector portion adapted to be removably coupled with a second connector portion provided on the headgear assembly.

3. A frame according to claim 1, wherein the channel includes a first surface to engage the cushion, to allow selective removal of the cushion from the frame.

4. A frame according to claim 3, wherein the first surface includes a protrusion on the inner wall.

5. A frame according to claim 4, wherein the channel further comprises a floor that extends between the inner and outer walls, each of the inner and outer walls includes a first end connected to the floor and a second end spaced from the first end, and the protrusion on the inner wall is spaced from the first end of the inner wall.

6. A frame according to claim 5, wherein the protrusion is configured to engage the side wall of the cushion so that a force required to attach the cushion to the frame is lower than a force required to detach the cushion from the frame.

7. A frame according to claim 5, wherein the floor of the channel is non-planar.

8. A frame according to claim 1, wherein the channel has a width in the range of about 2-10 mm.

9. A frame according to claim 8, wherein the width of the channel is 5 mm.

10. A frame according to claim 1, wherein the main body comprises an alignment feature on an outer surface configured to align with an alignment feature on the cushion.

11. A frame according to claim 10, wherein the channel includes an upper section dimensioned to be positioned over the patient's nasal bridge region, a generally horizontal lower section, and side sections to join the upper and lower sections.

12. A frame according to claim 11, wherein the length of the inner wall is greater than the length of the outer wall such that the inner wall protrudes further away from the rear surface.

13. A frame according to claim 1, wherein the channel is structured such that an engagement force for engagement of the cushion to the frame is less than the disengagement force.

14. A frame according to claim 13, wherein the channel is structured such that the disengagement force is greater than a force asserted upon the mask assembly at a maximum treatment pressure.

15. A frame according to claim 1, wherein a length of the side wall is at least equal to a depth of the channel such that the cushion may contact a bottom surface of the channel.

16. A frame according to claim 15, wherein the cushion is retained and sealed without an interior or exterior member.

17. A combination, comprising:
a frame according to claim 1; and
a plurality of cushions, each cushion being configured to be removably attachable to the frame, wherein the cushions are different sizes.

18. A combination according to claim 17, wherein each cushion is configured to accommodate a percentage of a patient population such that the plurality of cushions together accommodate up to 95-100% of the patient population.

19. A frame for a respiratory mask assembly that delivers breathable gas to a patient, the frame comprising:

a base having a front side, a rear side, and an aperture therethrough for the introduction of breathable gas into a nasal breathing cavity;
an elbow assembly movably supported on the front side of the base; and
an inner wall and an outer wall having a generally triangular or trapezoidal channel therebetween that is structured to receive a side wall of a cushion so as to allow repeated attaching and detaching of the cushion and the base, at least a portion of the channel being shaped and dimensioned to generally follow a contour of the patient's face, wherein
the inner wall includes a protrusion configured to contact the side wall of the cushion so as to removably attach the cushion to the base;
the channel has a width in the range of about 2-10 mm;
the base comprises an alignment feature configured to align with an alignment feature on the cushion;
the cushion can be attached to the frame to substantially simultaneously retain the cushion to the frame and form a seal with the frame; and
a depth of the channel is selected such that at least a portion of an end of the side wall of the cushion may contact a bottom surface of the channel; and
wherein each of the inner and outer walls extends from the rear side, and the inner wall extends a different distance than the outer wall, and wherein the side wall of the cushion is adapted to be positioned between the inner and outer walls when attached to the frame.

20. A frame according to claim 19, wherein each of the inner wall and outer wall has a thickness of about 1-2 mm.

21. A frame according to claim 19, wherein the width of the channel is 5 mm.

22. A frame according to claim 19, wherein the channel is structured such that an engagement force for engagement of the cushion to the frame is less than the disengagement force.

23. A frame according to claim 19, wherein the channel is structured such that a disengagement force is greater than a force asserted upon the mask assembly at a maximum treatment pressure.

24. A frame according to claim 19, wherein the cushion is retained and sealed without an interior or exterior member.

25. A frame according to claim 19, wherein the channel includes an upper section dimensioned to be positioned over the patient's nasal bridge region, a generally horizontal lower section, and side sections to join the upper and lower sections.

26. A combination, comprising:
a frame according to claim 19; and
a plurality of cushions, each cushion being configured to be repeatedly and removably attachable to and detachable from the frame, wherein the cushions are different sizes.

27. A combination according to claim 26, wherein each cushion is configured to accommodate a percentage of a patient population such that the plurality of cushions together accommodate up to 95-100% of the patient population.

28. A frame according to claim 19, wherein the inner wall and the outer wall each extend rearwardly from the rear side, the inner and outer walls being spaced in parallel to define the channel therebetween.

29. A frame according to claim 19, wherein the inner and outer walls each extend rearwardly from the rear side in a direction of engagement and disengagement of the cushion side wall with the channel.

30. A frame according to claim 29, wherein the direction of engagement and disengagement of the cushion side wall with the channel is parallel to a longitudinal axis of the aperture.

31. A frame according to claim 19, wherein the channel has a symmetrical shape.

32. A frame according to claim 19, wherein the channel has an asymmetrical shape.

33. A frame according to claim 19, wherein the channel has a trapezoidal shape.

34. A frame according to claim 19, wherein the width of the channel is constant.

35. A frame according to claim 19, further comprising at least one receptacle provided to the frame that is configured to receive a locking clip of a headgear.

36. A frame according to claim 19, wherein the outer wall defines a perimeter of the base.

37. A frame according to claim 19, wherein the elbow assembly includes at least one vent opening.

38. A frame according to claim 19, wherein the nasal breathing cavity is configured to encompass at least the patient's nose.

39. A frame for a respiratory mask assembly that delivers breathable gas to a patient, the frame comprising:
- a substantially rigid main body, the main body comprising:
  - a front surface and a rear surface adapted in use to face the patient, and
  - an aperture provided therethrough for the introduction of breathable gas into a nasal breathing cavity defined by the frame;
- a generally triangular or trapezoidal channel extending from the rear surface of the main body, the channel being structured to receive a side wall of a cushion so to removably attach the cushion to the frame, the channel comprising:
  - an inner wall and an outer wall spaced from and extending parallel to each other, and
  - a channel floor extending between the inner and outer walls, wherein the outer wall defines at least a portion of the outer perimeter of the main body, the channel having a generally horizontal upper section dimensioned to be positioned over the patient's nasal bridge region, a generally horizontal lower section that is generally parallel to the upper section, and side section to join the upper and lower sections; and
- wherein each of the inner and outer walls extends from the rear surface, and the inner wall extends a different distance than the outer wall, and wherein the side wall of the cushion is adapted to be positioned between the inner and outer walls when attached to the frame.

40. A frame according to claim 39, wherein the channel includes a first surface to frictionally engage a second surface of the side wall of the cushion to allow selective removal of the cushion from the frame.

41. A frame according to claim 40, wherein a depth of the channel is such that the side wall of the cushion may contact the channel floor when the first surface frictionally engages the second surface.

42. A frame according to claim 41, wherein the channel is structured to retain the cushion and form a seal without an interior or exterior member.

43. A frame according to claim 39, wherein the channel has a width in the range of about 2-10 mm.

44. A frame according to claim 43, wherein the inner wall has a thickness of about 1-2 mm.

45. A frame according to claim 44, wherein the outer wall has a thickness of about 1-2 mm.

46. A frame according to claim 39, wherein the channel is structured such that the disengagement force greater than a force asserted upon the mask assembly at a maximum treatment pressure.

47. A frame according to claim 45, wherein the channel is structured such that an engagement force for engagement of the cushion to the frame is less than the disengagement force.

48. A frame according to claim 39, wherein the inner and outer walls each extend in a direction of engagement and disengagement of the cushion side wall with the channel.

49. A frame according to claim 48, wherein the direction of engagement and disengagement of the cushion side wall with the channel is parallel to a longitudinal axis of the aperture.

50. A frame according to claim 49, wherein the width of the channel is constant.

51. A frame according to 39, wherein the inner and outer walls are parallel to a longitudinal axis of the aperture.

52. A frame according to claim 39, further comprising a swivel elbow coupled to the front surface of the main body.

53. A frame according to claim 52, wherein the swivel elbow comprises at least one vent.

54. A frame according to claim 39, further comprising a headgear connector provided at each of a first end of the frame and a second end of the frame opposite the first end.

55. A combination, comprising:
- a frame according to claim 39; and
- a plurality of cushions, each cushion being configured to be repeatedly and removably attached to and detachable from the frame, wherein the cushions are different sizes.

56. A frame according to claim 39, wherein interior surfaces of the inner and outer walls are tapered.

57. A respiratory mask assembly for delivering breathable gas to a patient, comprising:
- a rigid frame having a front surface and a rear surface, opposite the front surface, and adapted in use to face the patient, the frame defining an outer wall and an inner wall with at least the inner wall extending from the rear surface, the inner and outer walls being rigid and spaced to define a generally triangular or trapezoidal channel therebetween, the channel including a bottom surface defined by the frame and having a shape including a top region adapted to face the patient's nasal bridge, a bottom region, and two cheek regions that connect the top region and the bottom region, the inner wall having at least a first protruding portion that protrudes into the channel, wherein the frame, the inner wall, the outer wall, the channel bottom and the first protruding portion are formed in one piece; and
- a cushion being removably attachable to the frame such that the cushion and frame are repeatably engagable with and disengagable from one another, the cushion including a flexible and generally triangular or trapezoidal side wall to be inserted into the channel of the frame and is positioned between the rigid inner and outer walls of the frame, thereby forming a sealed connection therewith, the side wall having a shape that matches the shape of the channel, the side wall having an interior surface that engages the first protruding portion provided on the inner wall of the channel when the cushion and frame are engaged with one another, wherein, during assembly of the cushion and the frame, the interior surface and the first protruding portion engage one another to deform or compress the side wall in the vicinity of the interior surface and provide a retaining force to help maintain the sealed connection between the cushion and the frame such that the cushion is sealed and retained relative to the frame without an additional retaining member, and wherein each of the inner and outer walls include an end, and the inner wall end projects a different distance than the outer wall end.

58. A respiratory mask assembly according to claim 57, wherein the frame and cushion are configured to cover the patient's nose and mouth.

59. A respiratory mask assembly according to claim 58, wherein a width of the channel is between about 2-10 mm.

60. A respiratory mask assembly according to claim 59, wherein a length of the outer wall of the channel is different from a length of the inner wall of the channel.

61. A respiratory mask assembly according to claim 60, further comprising:
an elbow connected to the frame.

62. A respiratory mask assembly according to claim 61, further comprising:
a headgear connected to the frame.

63. A respiratory mask assembly according to claim 57, wherein the channel includes a shoulder or ledge that defines the maximum insertion depth of the cushion within the channel.

64. A respiratory mask assembly according to claim 63, further comprising an empty space positioned below the shoulder or ledge.

65. A respiratory mask assembly according to claim 57, further comprising a sealing lip extending outward from an exterior surface of the side wall to sealingly engage the outer wall of the frame.

66. A respiratory mask assembly according to claim 57, wherein the cushion comprises a frame contacting side and a patient contacting side, the frame contacting side comprises the side wall which has a first aperture, the patient contacting side comprises a second aperture, and the first aperture is larger than the second aperture.

67. A respiratory mask assembly according to claim 57, wherein the bottom region is configured to engage the patient's upper lip.

68. A respiratory mask assembly according to claim 57, wherein the bottom region is configured to engage the patient's bottom lip.

69. A frame for a respiratory mask assembly that delivers breathable gas to a patient, the frame comprising:
a substantially rigid main body having a generally triangular or trapezoidal shape and having a curvature adapted to generally follow at least a part of the facial contour of the patient's face, the main body comprising a front surface and a rear surface adapted in use to face the patient, and an aperture provided therethrough for the introduction of breathable gas into a nasal breathing cavity defined by the frame;
a channel structured to receive a side wall of a cushion so to removably attach the cushion to the frame, the channel comprising an inner wall and an outer wall spaced from and extending generally parallel to each other, and a channel floor extending between the inner and outer walls, wherein the outer wall defines at least a portion of the outer perimeter of the main body and the inner wall extends from the rear surface and is formed in one piece with the outer wall, the main body and the channel floor, at least a portion of the channel having a curvature adapted to generally follow at least a portion of the facial contour of the patient's face and a generally triangular or generally trapezoidal shape; and
wherein the inner wall extends a different distance than the outer wall, and
wherein the channel is structured to retain the cushion and form a seal without an interior or exterior member, and wherein the side wall of the cushion is adapted to be positioned between the inner and outer walls when attached to the frame.

70. A frame according to claim 69, wherein the channel includes a first surface to frictionally engage a second surface of the side wall of the cushion to allow selective removal of the cushion from the frame.

71. A frame according to claim 70, wherein a depth of the channel is such that at least a portion of the side wall of the cushion may contact the channel floor when the first surface frictionally engages the second surface.

72. A frame according to claim 69, wherein the channel has a width in the range of about 2-10 mm.

73. A frame according to claim 72, wherein the inner wall has a thickness of about 1-2 mm.

74. A frame according to claim 73, wherein the outer wall has a thickness of about 1-2 mm.

75. A frame according to claim 74, wherein the inner and outer walls each extend in a direction of engagement and disengagement of the cushion side wall with the channel.

76. A frame according to claim 75, wherein the direction of engagement and disengagement of the cushion side wall with the channel is parallel to a longitudinal axis of the aperture.

77. A frame according to claim 76, wherein the width of the channel is generally constant.

78. A frame according to claim 69, further comprising a swivel elbow coupled to the front surface of the main body, wherein the swivel elbow comprises a plurality of vent holes.

79. A combination, comprising:
a frame according to claim 69; and
a plurality of cushions, each cushion being configured to be repeatedly and removably attached to and detachable from the frame, wherein the cushions are different sizes.

80. A respiratory mask assembly for delivering breathable gas to a patient, comprising:
a frame having a main body, an outer wall, and an inner wall extending from the main body, the inner and outer walls having different extended lengths so as to establish a relative distance, said inner and outer walls being spaced to define a channel therebetween, the channel having a generally triangular or trapezoidal shape, wherein the inner wall includes a retaining element that protrudes into the channel, and wherein the main body, the inner wall, outer wall and retaining element are formed in one piece; and
at least one silicone cushion being removably attachable to the frame such that the cushion and frame are repeatably engagable with and disengagable from one another, the cushion including a deformable side wall to be inserted into the channel of the frame and being retained between the inner and outer walls of the frame, wherein the side wall frictionally contacts the inner and outer walls,
the side wall including at least one sealing lip positioned at or adjacent an end of the side wall, the sealing lip extending outward from an exterior surface of the side wall and running around the periphery of the side wall, thereby forming a sealed connection with the outer wall of the frame, the side wall having a shape that matches the shape of the channel,
wherein, during assembly, the relative distance between said extended lengths of the inner and outer walls of the frame assists in initial alignment of the side wall and the channel,
wherein the retaining element provided on the inner wall of the channel is positioned below a top edge of the inner wall such that during initial engagement between the cushion and the frame, the side wall begins to frictionally contact the inner and outer walls, before an interior surface of the side wall engages the retaining element provided on the inner wall of the channel, wherein, after the cushion and frame are initially engaged with one another, and upon further insertion of the cushion into the channel, the interior surface and the retaining element engage one another to deform or compress the side wall in the vicinity of the interior surface to at least partially provide a retaining force to help maintain the sealed connection between the cushion and the frame, and wherein the cushion is both sealed and retained relative to the frame without the need for a strap, an interior or exterior clip, or an additional retaining device.

81. A respiratory mask assembly according to claim 80, wherein the frame and cushion are configured to cover the patient's nose and mouth.

82. A respiratory mask assembly according to claim 81, wherein a width of the channel is between about 2-10 mm.

83. A respiratory mask assembly according to claim 80, wherein the end of the side wall is generally linearly aligned with the side wall so as to project away from the main body at a substantially right angle when assembled, and a sealing membrane curls inwardly from a top end of the side wall.

84. A respiratory mask assembly according to claim 83, wherein the end and the side wall have a thickness that is able to withstand buckling forces applied when the cushion and frame are engaged with one another.

85. A respiratory mask assembly according to claim 83, wherein the membrane has a thickness of 0.1 to 2 mm, and the sidewall has a thickness of 2-10 mm.

86. A respiratory mask assembly according to claim 85, wherein the membrane thickness is 0.35 mm.

87. A respiratory mask assembly according to claim 80, wherein the channel includes a shoulder or ledge that defines the maximum insertion depth of the cushion within the channel.

88. A respiratory mask assembly according to claim 80, wherein only one said sealing lip is provided, and said sealing lip is only provided to the exterior surface of the side wall of the cushion, and the retaining element is provided only to the inner wall of the channel of the frame.

89. A respiratory mask assembly according to claim 80, wherein the cushion and frame include matching alignment indicators that align only when the cushion and frame are properly positioned for initial engagement.

90. A respiratory mask assembly according to claim 80, wherein the relative distance is between 0.5-10 mm.

91. A respiratory mask assembly according to claim 80, wherein the inner and/or outer walls have a taper to ease assembly of the cushion and the frame.

92. A respiratory mask assembly according to claim 80, further comprising:
an elbow connected to the frame.

93. A respiratory mask assembly according to claim 92, wherein the elbow defines an intake port and an exhaust port separated by a baffle having a generally planar configuration, the exhaust port being in communication with a plurality of gas washout ports.

94. A respiratory mask assembly according to claim 93, wherein the elbow is releasably detachable from the frame without accessing an interior portion of a breathing cavity defined between the cushion and frame.

95. A respiratory mask assembly according to claim 94, further comprising:
a headgear connected to the frame.

96. A respiratory mask assembly according to claim 80, wherein the cushion comprises a frame contacting side and a patient contacting side, the frame contacting side comprises the side wall which has a first aperture, the patient contacting side comprises a second aperture, and the first aperture is larger than the second aperture.

97. A respiratory mask assembly according to claim 80, wherein the at least one cushion comprises a plurality of cushions, each cushion being configured to be repeatedly and removably attached to and detachable from the frame, wherein the cushions are different sizes.

* * * * *